(12) United States Patent
Parks et al.

(10) Patent No.: US 7,476,204 B2
(45) Date of Patent: Jan. 13, 2009

(54) VISUALIZATION OF VALUES OF A PHYSICAL PROPERTY DETECTED IN AN ORGANISM OVER TIME

(75) Inventors: Thomas R. Parks, Hermosa Beach, CA (US); Jae S. Son, Rancho Palos Verdes, CA (US)

(73) Assignee: Pressure Profile Systems, Inc., Los Angeles, CA (US)

( * ) Notice: Subject to any disclaimer, the term of this patent is extended or adjusted under 35 U.S.C. 154(b) by 567 days.

(21) Appl. No.: 10/281,068

(22) Filed: Oct. 24, 2002

(65) Prior Publication Data

US 2003/0135120 A1 Jul. 17, 2003

Related U.S. Application Data

(60) Provisional application No. 60/343,714, filed on Oct. 24, 2001, provisional application No. 60/347,599, filed on Oct. 24, 2001.

(51) Int. Cl.
*A61B 5/103* (2006.01)
*A61B 5/117* (2006.01)
*A61B 5/04* (2006.01)
*A61B 5/02* (2006.01)

(52) U.S. Cl. .............. 600/593; 600/587; 600/372; 600/373; 600/482; 600/485; 600/500; 600/501

(58) Field of Classification Search .......... 600/593, 600/587, 372, 373, 482, 485, 500, 501
See application file for complete search history.

(56) References Cited

U.S. PATENT DOCUMENTS 5,533,515 A * 7/1996 Coller et al. ............. 600/593

OTHER PUBLICATIONS

Abstract for "Changes in Upper Esophageal Motor Function in Reflux Esophagitis by High Resolution Manometry (HRM)," Supplement to Gastroenterology, Digestive Disease Week and the 102nd Annual Meeting of the Amer. Gastroenterological Assoc., vol. 120, No. 5, Supp 1, Apr. 2001, #1151 on p. A-219.

(Continued)

*Primary Examiner*—Max Hindenburg
*Assistant Examiner*—Jeffrey G Hoekstra
(74) *Attorney, Agent, or Firm*—Wolf, Greenfield & Sacks, P.C.

(57) ABSTRACT

A system for visually indicating, in real time or post hoc, values of a physical property detected over a period of time along a dimension of an organism to a user on a temporal plot and a profile plot, either individually or concurrently. The detected values may be visually indicated on the temporal plot using any of a variety of techniques, including, but not limited to, a contour technique, a line trace technique or a mesh plot technique. Further, the detected values may be visually indicated on the profile plot using any of a variety of techniques, including, but not limited to a contour technique, a line trace technique or a histogram technique. To provide a finer spatial resolution, values may be interpolated for locations between the locations at which values were detected, and these values may be displayed on the temporal plot and the profile plot.

77 Claims, 29 Drawing Sheets

OTHER PUBLICATIONS

Abstract for "Pressure-Geometry Relationships in the Stomach Analyzed Through Computer Simulation," Gastroenterology, Digestive Disease Week and the 100th Annual Meeting of the Amer. Gastroenterological Assoc., May 16-19, 1999, Orlando, FL, vol. 116, No. 4, Part 2, #G4594.

Abstract for "Technical Aspects of high resolution perfusion manometry—An underwater zero improves accuracy of measurement of catheter offset and transducer drift," Supplement to Gastroenterology, Digestive Disease Week and the 97th Annual Meeting of the Amer. Gastroenterological Assoc., May 11-14, 1997, Washington, DC, vol. 112, No. 4, p. A745.

Abstract for "Insights into stomach mechanics from concurrent gastric ultrasound and manometry," Gastroenterology, Official Journal of the Amer. Gastroenterological Assoc., Oct. 1994, vol. 107, No. 4, p. 1236.

Abstract for "Does high resolution manometry detect esophageal motility disorders more reliable than conventional manometry?" Dysophagia, An International Multidisciplinary Journal Devoted to Swallowing and its Disorders, Official Journal of the Dysphgia Research Society, vol. 16, No. 1, Winter 2001.

Ray E. Clouse, M.D., et al., Application of Topographical Methods to Clinical Esophageal Manometry, The Am. J. of Gastroenterology, (Nov. 2000), vol. 95, pp. 2720-2730.

Ray E. Clouse and Annamaria Staiano, Topography of the Esophageal Peristaltic Pressure Wave, The Am. Physiological Society. (1991), pp. G677-G684.

G.S. Hebbard, Trace! 1.1, User Manual, Advanced Manometry Systems, Adelaide, Aug. 2001.

Ray E. Clouse, M.D., et al., Topographic Esophageal Manometric: an Emerging Clinical and Investigative Approach, *Digestive Diseases* 200;18:67-74.

P. J. Kahrilas et al., Effect of Peristaltic Dysfunction on Esophageal Volume Clearance, *American Gastroenterological Assoc.* 1988;94:73-80.

Geoff Hebbard, Computerised Mapping Provides New Insights into Oesophaegeal Motility Disorders, *Repatriation General Hospital, Daw Park*, 14 IMS Slides.

Geoff Hebbard, Current Investigations-a Wast of Time?, *Repatriation General Hospital, Daw Park*, 14 IMS Slides.

Geoff Hebbard, Spatiotemporal Pressure Maps in Vivo, *Repatriation General Hospital, Adelaide*, Australia, 14 IMS Slides.

\* cited by examiner

VISUALIZATION OF VALUES OF A PHYSICAL PROPERTY DETECTED IN AN ORGANISM OVER TIME

RELATED APPLICATIONS

This application claims the benefit under 35 U.S.C. §119(e) to commonly-owned U.S. provisional patent application ser. No. 60/343,714, entitled TIME SPATIAL VISUALIZATION OF LINEAR ARRAY DATA, filed on Oct. 24, 2001 and commonly-owned U.S. provisional patent application ser. No. 60/347,599, entitled CAPACITIVE ARRAY SENSOR ELECTRONICS, filed on Oct. 24, 2001.

Commonly-owned Patent Cooperation Treaty patent application titled ARRAY SENSOR ELECTRONICS, filed on even date herewith under Ser. No. 10/493,459, is incorporated herein by reference in its entirety.

GOVERNMENT RIGHTS

The U.S. Government has a paid-up license in this invention and the right in limited circumstances to require the patent owner to license others on reasonable terms as provided for by the terms of Contract/Grant No. 1 R43 DK5639-01 awarded by National Institutes of Health.

BACKGROUND

The esophagus is a tubular organ that carries food and liquid from the throat to the stomach. The interior surface of the esophagus contains muscles that rhythmatically contract whenever a person swallows. This contraction generally occurs as a sweeping wave carrying food down the esophagus to the stomach. This sweeping wave of contraction is typically referred to as peristalsis. An upper esophageal sphincter (UES) is located at an upper end of the esophagus. The UES is a muscle that serves as a valve between the esophagus and the pharynx from which the esophagus receives food and liquid when swallowing.

The lower esophageal sphincter (LES) is located at a lower end of the esophagus. The LES is a muscle that serves as a valve between the esophagus and the stomach. The LES protects the lower esophagus from stomach acid and bile, which cause the discomfort of heartburn and in time can damage or scar the esophagus.

The diaphragm is a muscular membrane that assists is respiration and intersects the upper Gastrointestinal (GI) tract at an approximate right angle, typically within the length of the LES, creating a pressure inversion point (PIP), which is often referred to as the respiratory inversion point (RIP). As used herein, an "upper GI tract" includes at least the UES, esophagus, LES and at least portions of the pharynx and stomach. The PIP is named as such because it is a point along the length of the upper GI tract (typically within, but sometimes proximate to, the LES) where the muscular pressure in response to respiration inverts. Above the PIP, pressure increases during inhalation and decreases during exhalation. In contrast, below the PIP, the pressure decreases during inhalation and increases during exhalation. A hiatal hernia occurs if the PIP (i.e., the intersection of the diaphragm and the LES) is not within the LES, but is located below the LES within the upper regions of the stomach Manometry is the recording of muscle pressures within an organ. Esophageal manometry measures the muscular pressure exerted along the upper GI tract, for example, during peristalsis. Esophageal manometry is used to evaluate the contraction function of the upper GI tract in many situations (e.g., breathing, swallowing food, swallowing liquid, drinking, coughing, etc.) and can be useful for diagnosing symptoms that originate in the esophagus, for example, difficulty in swallowing food or liquid, heartburn, and chest pain to determine the cause of the symptoms, for example, dysphasia or echolalia.

A variety of esophageal manometry systems have been used to study pressure along the upper GI tract. Such systems typically include a probe that is inserted into the upper GI tract and one or more pressure sensors that detect pressure from different locations within the upper GI tract. One type of a probe is a catheter. An esophageal manometry system that has a catheter as a probe is a referred to herein as a catheter-based esophageal manometry system. Types of catheter-based esophageal manometry systems include solid state systems and water perfuse systems. In water perfuse systems, pressure sensors are located external to the catheter. Each pressure sensor has a corresponding tube that extends into the catheter and pumps fluid (e.g., water) at some longitudinal location of the catheter against the interior surfaces of the GI tract. The pressure resulting from the impact of the fluid against the interior surface is transmitted via the fluid through the tube to the pressure sensor, where it is detected. In contrast, solid state systems do not use fluids, and each sensing element is attached to or embedded within the catheter and detects pressure locally at the point of impact with the interior surface of the upper GI tract. Each sensor transmits its detected values out of the catheter using an electronic or optical signal.

Existing solid state, catheter-based, esophageal manometry systems typically include only four to eight sensors that detect pressure values during a given temporal interval. Such sensors typically are located several centimeters (i.e., more than three centimeters) apart from one another. Such systems may include an application that displays the detected values as line trace plots to a user. The low spatial resolution of the sensors in such systems results in a low spatial resolution of information being detected and displayed to the user for any given temporal interval. To increase the spatial resolution of detected values in such systems, the catheter may be moved such that the sensors detect values at other locations, for example, locations between the previous locations of the sensors. These latter detected values, however, are detected during different temporal intervals than previous values, so the user still is not provided spatially dense information during a single temporal interval.

Water perfuse catheter-based systems are described in "Topography of the esophageal peristaltic pressure wave," by R. Clouse, American Journal of Physiology, 1991; 261 (Gastrointest Liver Physio 24): G677-G684, and in "Topographic Imaging of Esophageal Manometric Signals," R. Clouse, (Motility 1999; 48: 11-13), and have been made available from Medical Measurement Systems, b.v. of Sweden). Water perfuse catheter-based system may include a catheter and up to twenty one tubes where each tube has an opening on its side at a different longitudinal location along the catheter from which it releases water. The resulting pressure from tissue contact at each release site is then transmitted through the water in the tube to a corresponding sensor. Each tube opening is spaced approximately one centimeter apart from a nearest other tube along the longitudinal axis of the catheter. Thus, a water perfuse catheter-based system may have a higher spatial resolution than existing solid state, catheter-based esophageal manometry systems.

An esophageal manometry system may include or be accompanied with an application that visually indicates the values detected by the sensors to a user, and may be capable of visually indicating the values detected by the sensor on a temporal plot in real time using a line trace technique. As used herein, a "temporal plot" is a plot having a temporal axis, where, for each of a plurality of temporal intervals, values detected during the temporal interval are visually indicated at a temporal position relative to the temporal axis that corresponds to the temporal interval. The values detected during different temporal intervals are visually indicated concurrently. A temporal plot is useful to concurrently illustrate values of a physical property detected at one or more locations over time.

As used herein, a value detected for a physical property is visually indicated "in real time" if the duration of time between the time at which the value was detected and the time at which the value is initially visually indicated is short enough relative to the rate at which the physical property changes such that the visually indicated value may be considered the current value of the physical property at the time of its initial visual indication. Such visually indicated value may be considered the current value because, even if the physical property has changed during the time between its detection and its initial visual indication, the rate of change is slow enough such that the amount of change is tolerable in the context in which the value is being used.

Thus, in the context of esophageal manometry, a detected pressure value at a location in the esophagus is visually indicated "in real time" if the duration of time between the time at which the pressure value was detected and the time at which the value is initially visually indicated is short enough relative to the rate at which the pressure changes in the esophagus such that the visually indicated pressure value at the time of its initial visual indication is considered the current value of pressure at the location.

As used herein, a "line tracing technique" of visually indicating values detected at different locations over time on a temporal plot means, for each location, visually indicating a baseline for the location, the baseline running parallel to the temporal axis. The value detected at the location during each temporal interval is represented as an offset from the baseline at a temporal position relative to the temporal axis that corresponds to the temporal interval. The amount of the offset corresponds to the detected value. Each visually indicated value detected at the location is connected by a continuous line, which, depending on the detected values, may be a straight line or a curved line.

Some such software applications also concurrently visually indicate detected values on a temporal plot and a profile plot, but not in real time (i.e., post hoc). As used herein, visually indicating detected values "post hoc" means not visually indicating the detected values in real time. Typically, the detected values are first recorded and then the recorded values are extracted by a program that visually indicates the values on the temporal plot and the profile plot, concurrently. As used herein, a "profile plot" is a plot that has a spatial axis, where, for each of a plurality of temporal intervals, for each value detected. At a different location along a dimension (i.e., a spatial dimension) from a reference point during the temporal interval, the value is visually indicated at a spatial position relative to the spatial axis. The spatial position corresponds to the location at which the value was detected. At any given time, only values detected during a single temporal interval are visually indicated on the profile plot.

The temporal plot on known systems that visually indicate values post hoc may use a line tracing technique or a contour technique. As used herein, displaying values of a physical property detected by sensors located at different locations along a dimension of an organism over time on a temporal plot using a contour technique means the following. For each of a plurality of temporal intervals of the period, for each of a plurality of the sensors, a value of the physical property detected by the sensor during the temporal interval is visually indicated at a coordinate of the temporal plot. The temporal plot has a temporal axis representing time and a spatial axis, oriented orthogonally to the temporal axis, representing the dimension. The value is visually indicated at the coordinate using a tone (i.e., a color or grayscale value) corresponding to the value, and the coordinate has a spatial position relative to the spatial axis that corresponds to the location of the sensor and has a temporal position relative to the temporal axis that corresponds to the temporal interval.

The contour technique employed by known systems for visually indicating detected values on a temporal plot is static in that the positions of the detected values displayed on the temporal plot do not change and the temporal intervals displayed on the temporal plot remain fixed as the user views the temporal plot.

Accordingly, for such a static temporal plot visually indicated post hoc along with a profile plot, even if the profile plot changes with time to display values from different temporal intervals, there is no correlation to the values being visually indicated on the profile plot and the visual indication of detected values on the temporal plot.

Further, in such known systems when values are visually indicated on a temporal plot and a profile plot, concurrently, post hoc, the temporal axis of the temporal plot is oriented vertically on the image presented to the user and the spatial axis of the temporal plot and the profile plot are oriented horizontally on the image presented to the user.

Further, although known esophageal manometry systems visually indicate detected values on a profile plot post hoc, such systems do not visually indicate detected values on a profile plot in real time.

SUMMARY

One problem with known manometry systems is that, for real time visual indication of values detected over a period of time to a user on a temporal plot, such systems are limited to visually indicating the values using a line-trace technique. A drawback to visually indicating values on a temporal plot using a line trace technique (e.g., see FIG. 11, Item 1002) is that as the number of locations for which values are visually indicated grows, the more confusing the plot becomes to a user. Typically, to limit this confusion, values detected from only a limited number of locations over time are visually indicated. This limited number of locations limits the density of the spatial resolution of the visually indicated values along the spatial axis. Unfortunately, when limiting the number of locations for which values are visually indicated, the number of locations for which values are not visually indicated grows as well as the number of locations grow. As a result, a user may be provided with relatively sparse information about the values of a physical property detected along a dimension within the GI tract over time although more information is available. For example, if the user is a doctor examining the upper GI tract of a patient, the doctor may be limited in his/her ability to determine the condition of the patient's upper GI tract over time while the values are being detected within the GI tract because not all of the available information is made available to the doctor.

Thus, an improved technique is needed for visually indicating to a user, on a temporal plot in real time, values detected over a period of time along a dimension of an organism, where the visual indication of such values has a higher spatial resolution than that produced using a line tracing technique.

Accordingly, in an aspect of the invention, a system for, and method of, visually indicating, in real time, values of a physical property detected over a period of time along a dimension of an organism (e.g., along the length of an upper GI tract) to a user on a temporal plot using a contour technique are provided. To provide a finer spatial resolution, values may be interpolated for locations between the locations at which values were detected, and these values may be displayed on the temporal plot as well.

Another problem with know manometry systems is that, although some of such systems visually indicate values detected over time to a user concurrently on a temporal plot and profile plot, post hoc, no such systems visually indicate the values to the user concurrently on a temporal plot and profile plot in real time. Thus, a user (e.g., a physician) must wait until after the values have been persisted to view the detected values on a temporal plot and a profile plot concurrently. Not being able to view the detected values in real time prevents a user from being able to analyze the detected values and possibly diagnose the condition of an upper GI tract from which the values were detected. Further, not being able to view the detected values in real time may prevent the user from making adjustments in the position of the sensors detecting the values as the values are being detected.

Accordingly, in another aspect of the invention, a system for, and method of, visually indicating, in real time, values of a physical property detected over a period of time along a dimension of an organism (e.g., along the length of an upper GI tract) to a user on a temporal plot and a profile plot, concurrently are provided. In this aspect, the detected values may be visually indicated on the temporal plot using any of a variety of techniques, including, but not limited to, a contour technique, a line trace technique or a mesh plot technique. Further, in this aspect, the detected values may be visually indicated on the profile plot using any of a variety of techniques, including, but not limited to a contour technique, a line trace technique or a histogram technique.

Another problem with known manometry systems is that, although some of such systems can visually indicate values detected over a period of time to a user, post hoc, on a temporal plot using a contour technique and on a profile plot, concurrently, the temporal axis of the contour plot is vertical and the spatial axes of both plots is horizontal. This orientation of axes is counter-intuitive to a user, as typically the temporal of a temporal plot is horizontal.

Accordingly, in another aspect of the invention, a system for, and method of, visually indicating, in real time or post hoc, values of a physical property detected over a period of time along a dimension of an organism (e.g., along the length of an upper GI tract) to a user on a profile plot and on a temporal plot having a horizontally-aligned temporal axis (with respect to the user) using a contour technique, concurrently, are provided. In a feature of this aspect, the spatial axes of both plots may be vertically aligned. In this aspect, the detected values may be visually indicated on the profile plot using any of a variety of techniques, including any of those techniques described herein.

Another drawback with known esophageal manometry systems is that none of such systems have the ability to visually indicate, in real time, values detected over a period of time on a profile plot.

Accordingly, in another aspect of the invention, a system for, and method of, visually indicating, in real time or post hoc, values of a physical property detected over a period time along a dimension of an organism (e.g., along the length of an upper GI tract) to a user on a profile plot are provided.

Another problem with known esophageal manometry systems is that none of such systems have the ability to visually indicate values detected over a period of time on a profile plot using a contour technique, as known systems are typically limited to displaying detected values on a profile plot using a line tracing technique.

Accordingly, in yet another aspect of the invention, a system for, and method of, visually indicating, in real time or post hoc, values of a physical property detected over a period of time along a dimension of an organism (e.g., an upper GI tract) to a user on a profile plot using a contour technique are provided.

Another drawback to known esophageal manometry systems is that, although such systems may be capable of visually indicating values detected over a period of tine on a plot, no such systems are capable of toggling between a first technique for visually indicating the detected values on the plot and a second technique for visually indicating the values on the plot. Such plot may be a temporal plot or a profile plot, and for either type of plot, the toggle techniques may be any of a variety of techniques for visually indicating values detected over a period of time, including any of those techniques described herein. Accordingly, after the visual indication of the values detected over a period of time has begun, the user does not have the ability to change the technique being used to display the detected values.

Accordingly, in another aspect of the invention, a system for, and method of, toggling between a plurality of techniques for visually indicating, in real time or post hoc, values of a physical property detected over a period of time along a dimension of an organism (e.g., along the length of an upper GI tract) to a user on a plot (e.g., a temporal plot or profile plot) are provided.

Another drawback to known esophageal manometry systems is that, although some of such systems visually indicate values detected over a period or time to a user, such systems do not indicate to the user the location at which the values were detected with respect to an anatomical landmark, for example, a UES, LES, upper margin of an LES, lower margin of an LES or a PIP. Not knowing the location of anatomical landmarks with respect to the locations of detected values may limit a user's ability to determine conditions along the upper GI tract, and to diagnose any symptoms relating to the upper GI tract.

Accordingly, in another aspect of the invention, a system for, and method of, determining the locations of one or more anatomical landmark identifiers along a dimension of an organism (e.g., along the length of an upper GI tract) based on values of a physical property detected along the dimension over time are provided.

In another aspect, a system for, and method of, visually indicating the location of one or more landmark identifiers on a temporal plot and/or a temporal plot are provided.

In yet another aspect of the invention, a system for, and method of, visually indicating an anatomical image on a profile plot concurrently to visually indicating values detected over a period of time along a dimension of an organism are provided. In a feature of this aspect, the anatomical image is configured based on the locations of one or more landmark identifiers.

In another aspect of the invention, if values detected from only a subset of the sensors are being visually indicated, a system for, and method of, determining for which sensors values are to be visually indicated based on one or more distances specified relative to one or more anatomical landmarks are provided.

Another drawback with known esophageal manometry systems is that no such systems visually indicate values detected over a period of time on both a first temporal plot and a second temporal plot, concurrently. For example, such systems do not visually indicate detected values on a first plot using a first technique concurrently to visually indicating the detected values on a second plot using a second technique. Accordingly, if each technique provides different information that is useful to a user, the user is deprived of having all of the available information concurrently.

In yet another aspect of the invention, a system for, and method of, visually indicating values of a physical property detected over a period of time along a dimension of an organism (e.g., along the length of an upper GI tract) on a first temporal plot and a second temporal plot, concurrently, are provided. In a feature of this aspect, the first temporal plot may use a different technique for visually indicating the detected values than the second temporal plot. Either plot may use any of a variety of techniques, for example, any of the techniques disclosed herein. Further, such concurrent visual indication may be in real time or post hoc. In another feature of this embodiment, one of the temporal plots may be scaled down and superimposed on the other plot. In yet another feature of this aspect, a user may be provided the ability to toggle between visually indicating the values on only one temporal plot and visually indicating the values on two temporal plots, concurrently. In another feature of this aspect, values detected over a period of time are visually indicated to a user on a first temporal plot, a second temporal plot and a profile plot, concurrently.

In another aspect of the invention, to accommodate for sensors that fail to detect values during one or more spatial intervals, a system for, and method of, interpolating a value for a channel based on other values detected during the temporal interval are provided. Such interpolation may be a linear interpolation or a non-linear interpolation, for example, cubic spline interpolation. These interpolated values for sensors that fail to detect values may be treated as detected values by other elements of a system in which the detected values are used.

In yet another embodiment, to provide a higher spatial resolution of the visual indications or values on a temporal plot and/or profile plot, a system for, or method of, interpolating values for locations along a first dimension between locations at which values were detected are provided. These interpolated values then may be visually indicated along with detected values on a temporal plot and/or profile plot.

In yet another embodiment of the invention, when values from only a subset of the sensors are being visually indicated on a plot, for example, on a temporal plot using a line tracing technique, a system for, and method of, visually indicating the identity of the sensors for which values are being displayed are provided. For example, such visual indications may be included on the temporal plot and/or a profile plot. Further, such indications may indicate a temporal plot and/or a profile plot. Further, such indications may indicate a location along a dimension (e.g., of an organism) at which the sensors for which values are being visually indicated are located.

In yet another aspect of the invention, a system for, and method of, visually indicating annotations on a profile plot and/or a temporal plot are provided.

In another aspect, a system for, and method of, normalizing visually indicated values detected along a dimension of an organism based on the values detected from one of the sensors within the organism are provided. In a feature of this aspect, a user may be unable to select a sensor, and values detected by the sensor over time may be used to determine a normalizing value by which to normalize the values detected by a plurality of sensors.

A drawback of systems that include a plurality of solid state sensors that detect values of a physical property detected along a dimension of an organism (e.g., along the length of an upper GI tract) is that the sensors are spaced apart at such a distance that spatial resolution of the detected data is low. Accordingly, a user's ability to determine the condition of the upper GI tract is compromised.

Accordingly, in another aspect, a system for detecting and visually indicating values of a physical property having a high spatial resolution along a dimension of an organism (e.g., along a length of an upper GI tract) is provided. For example, the system may include a plurality of sensors spaced in a close proximity to one or more nearest sensors, for example, less then three centimeters, such as less than two centimeters, for example, one centimeter or less. The values detected by these sensors over a period of time are transmitted to a visualization component that visually indicates the detected values over time using a temporal plot, a profile plot, or a combination thereof. The spatial resolution along the first dimension of the visually indicated values may be made even higher by interpolating values for locations between the locations of one or more of the sensors from which values are detected.

In an embodiment of the invention, values of a physical property detected over a period of time are visually indicated to a user. The values are detected by sensors located at different predefined distances from a reference point along a spatial dimension of an organism, and the period of time includes a plurality of temporal intervals. For a first of the plurality of temporal intervals, for each of a plurality of the sensors, a value of the physical property detected by the sensor during the temporal interval is visually indicated in real time at a coordinate of a temporal plot, which has a temporal axis representing time and a spatial axis, oriented orthogonally to the temporal axis, representing the spatial dimension. The value is visually indicated using a tone corresponding to the value. The coordinate has a spatial position relative to the spatial axis that corresponds to the location of the sensor and has a temporal position relative to the temporal axis that corresponds to the temporal interval. This act of visually indicating values may be repeated for a next one ore more temporal intervals, where the values detected by the plurality of sensors during the one or more next temporal intervals and the values detected by the plurality of sensors during the first temporal interval are concurrently visually indicating to the user on the temporal plot.

This embodiment and/or aspects thereof may be implemented as a computer program product that includes a computer-readable medium and computer-readable signals stored on the computer-readable medium, which signals define appropriate instructions. These instructions, as a result of being executed by a computer, instruct the computer to perform the acts described above for this embodiment.

In another embodiment, values of a physical property detected over a period of time by sensors located at different predefined distances from a reference point along a spatial dimension of an organism are visually indicated to a user. The period of time includes a plurality of temporal intervals. For a first of the plurality of temporal intervals, for each sensor of at least a subset of a plurality of the sensors, a respective value of the physical property detected by the sensor during the temporal interval is visually indicated in real time on a coordinate of a temporal plot, which has a temporal axis representing time. The coordinate has a temporal position relative to the temporal axis that corresponds to the temporal interval. Concurrently to visually indicating the values on the temporal plot, for each sensor of the plurality of sensors, the value of the physical property detected by the sensor during the temporal interval is visually indicated to the user in real time at a coordinate of a profile plot, which has a spatial axis representing the spatial dimension. The coordinate has a spatial position relative to the spatial axis that corresponds to the location of the sensor. Visually indicating detected values on the temporal plot is repeated for a next one or more of the plurality of temporal intervals in sequence. The values detected by the at least subset of the plurality of sensors during the one or more next temporal intervals and the values detected by the at least subset of the plurality of the plurality of sensors during the first temporal interval are concurrently visually indicated to the user on the temporal plot. Concurrently to repeating the visual indication of detected values on the temporal plot for a next one or more intervals, the values detected by the next one or more intervals are visually indicated on the profile plot, where the visual indication of the value detected by each of the plurality of sensors for a temporal interval is replaced with the visual indication of the value detected by the sensor during a next temporal interval.

This embodiment and/or aspects thereof may be implemented as a computer program product that includes a computer-readable medium and computer-readable signals stored on the computer-readable medium, which signals define appropriate instructions. These instructions, as a result of being executed by a computer, instruct the computer to perform the acts described above for this embodiment.

In yet another embodiment, provided is a method of visually indicating to a user values of a physical property detected over a period of time by sensors located at different predefined distances from a reference point along a spatial dimension of an organism, wherein the period of time includes a plurality of temporal intervals, the method comprising acts of: (A) for a first of the plurality of temporal intervals, for each sensor of at least a subset of a plurality of the sensors, visually indicating a respective value of the physical property detected by the sensor during the temporal interval on a coordinate of a temporal plot having a temporal axis representing time, the coordinate having a temporal position relative to the temporal axis that corresponds to the temporal interval; (B) concurrently to performing act (A), for each sensor of the plurality of sensors, visually indicating the value of the physical property detected by the sensor during the temporal interval to the user at a coordinate of a profile plot having a spatial axis representing the spatial dimension, the coordinate having a spatial position relative to the spatial axis that corresponds to the location of the sensor; and (C) repeating act (A) for a next one or more of the plurality of temporal intervals in sequence, including concurrently visually indicating to the user on the temporal plot the values detected by the at least subset of the plurality of the sensors during the one or more next temporal intervals and the values detected by the at least subset of the plurality of the sensors during the first temporal interval, and (D) concurrently to performing act (C), repeating act (B) for the next one or more temporal intervals, including, for each performance of act (D), replacing the visual indication of the value detected by each of the plurality of the sensors for a temporal interval with the visual indication of the value detected by the sensor during a next temporal interval, wherein the spatial axis of the temporal plot and the spatial axis of the profile plot are laterally aligned.

This embodiment and/or aspects thereof may be implemented as a computer program product that includes a computer-readable medium and computer-readable signals stored on the computer-readable medium, which signals define appropriate instructions. These instructions, as a result of being executed by a computer, instruct the computer to perform the acts described above for this embodiment.

In another embodiment, provided is a method of visually indicating to a user values of a physical property detected over a period of time by sensors located at different predefined distances from a reference point along a spatial dimension of an organism, wherein the period of time includes a plurality of temporal intervals, the method comprising acts of: (A) using a first process to visually indicate values of physical properties detected by at least a subset of a plurality of the sensors during different temporal intervals on a temporal plot having a temporal axis representing time and a spatial axis, oriented orthogonally to the spatial axis, representing the spatial dimension; (B) receiving a user input indicating to use a second process different than the first process to visually indicate the values; and (C) in response to the user input, switching from the first process to a second process to visually indicate the values on the plot, wherein, for each of the plurality of temporal intervals, for each of the at least subset of the plurality of the sensors, the first process visually indicates the value detected by the sensor during the temporal interval by performing one of the following acts: (1) visually indicating the value at a coordinate of the plot using a tone corresponding to the value, the coordinate having a spatial position relative to the spatial axis that corresponds to the location of the sensor; or (2) visually indicating the value detected by each sensor during the temporal interval as a displacement from a coordinate of the temporal plot, the coordinate from which the visual indication of each value is displaced having a spatial position relative to the spatial axis that corresponds to the predefined distance along the spatial dimension to the predefined distance along the spatial dimension at which the sensor from which the value was detected is located, and wherein, the second process visually indicates the values detected by the sensors by performing whichever of acts (1) and (2) are not performed by the first process.

This embodiment and/or aspects thereof may be implemented as a computer program product that includes a computer-readable medium and computer-readable signals stored on the computer-readable medium, which signals define appropriate instructions. These instructions, as a result of being executed by a computer, instruct the computer to perform the acts described above for this embodiment.

In yet another embodiment, provided is a method of visually indicating to a user values of a physical property detected over a period of time by sensors located at different predefined distances from a reference point along a spatial dimension of an organism, wherein the period of time includes a plurality of temporal intervals, the method comprising acts of: (A) for a first of the plurality of temporal intervals, for each of a plurality of the sensors, visually indicating a value of the physical property detected by the sensor during the first temporal interval to the user at a coordinate of a profile plot having a spatial axis representing the spatial dimension, the coordinate having a spatial position relative to the spatial axis that corresponds to the location of the sensor; (B) repeating act (A) for a next one or more temporal intervals, including, for each performance of act (B), replacing the visual indication of the value detected by each sensor for a temporal interval with the visual indication of the value detected by the sensor during a next temporal interval; and (C) for each performance of act (A), visually indicating an anatomical landmark of the organism at a coordinate of the plot, the coordinate at which the landmark is visually indicated having a spatial position relative to the spatial axis corresponding to a distance from the reference along the dimension within the organism at which the landmark is located.

This embodiment and/or aspects thereof may be implemented as a computer program product that includes a computer-readable medium and computer-readable signals stored on the computer-readable medium, which signals define appropriate instructions. These instructions, as a result of being executed by a computer, instruct the computer to perform the acts described above for this embodiment.

In another embodiment, provided is a method of visually indicating to a user values of a physical property detected over a period of time by sensors located at different predefined distances from a reference point along a spatial dimension of an organism, wherein the period of time includes a plurality of temporal intervals, the method comprising acts of: (A) for a first of the plurality of temporal intervals, for each of a plurality of the sensors, visually indicating a value of the physical property detected by the sensor during the first temporal interval to the user at a coordinate of a profile plot having a spatial axis representing the spatial dimension, the coordinate having a spatial position relative to the spatial axis that corresponds to the location of the sensor; and (B) repeating act (A) for a next one or more temporal intervals, including, for each performance of act (B), replacing the visual indication of the value detected by each sensor for a temporal interval with the visual indication of the value detected by the sensor during a next temporal interval; and (C) for each performance of act (A), visually indicating an image of at least a portion of the organism on the plot concurrently to visually indicating the values.

This embodiment and/or aspects thereof may be implemented as a computer program product that includes a computer-readable medium and computer-readable signals stored on the computer-readable medium, which signals define appropriate instructions. These instructions, as a result of being executed by a computer, instruct the computer to perform the acts described above for this embodiment.

In another embodiment, provided is a method of visually indicating to a user values of a physical property detected over a period of time by sensors located at different predefined distances from a reference point along a spatial dimension of an organism, wherein the period of time includes a plurality of temporal intervals, the method comprising acts of: (A) for a first of the plurality of temporal intervals, for each of a plurality of the sensors, visually indicating a value of the physical property detected by the sensor during the temporal interval at a coordinate of a temporal plot having a temporal axis representing time and a spatial axis, oriented orthogonally to the temporal axis, representing the spatial dimension, including visually indicating the value using a tone corresponding to the value, the coordinate having a spatial position relative to the spatial axis that corresponds to the location of the sensor and having a temporal position relative to the temporal axis that corresponds to the temporal interval; (B) concurrently to act (A), for the first of the plurality of temporal intervals, for each of at least a subset of the plurality of sensors, visually indicating a value of the physical property detected by the sensor during the temporal interval on a second temporal plot having a temporal axis representing time, wherein, for each of the at least subset of the plurality of sensors, the second temporal plot includes a baseline for the sensor, the baseline running parallel to the temporal axis, and wherein the value detected by the sensor is represented as an offset from the baseline at a temporal position relative to the temporal axis that corresponds to the first temporal interval, the amount of the offset corresponding to the value; and (C) repeating act (A) for a next one or more of the plurality of temporal intervals in sequence, including concurrently visually indicating to the user on the second temporal plot the values detected by the sensors during the one or more next temporal intervals and the values detected by the sensors during the first temporal interval; and (D) concurrently to performing act (C), repeating act (B) for a next one or more of the plurality of temporal intervals in sequence, including concurrently visually indicating to the user on the second temporal plot the values detected by the at least subset of the plurality of sensors during the one or more next temporal intervals and the values detected by the at least subset of the plurality of sensors during the first temporal interval.

This embodiment and/or aspects thereof may be implemented as a computer program product that includes a computer-readable medium and computer-readable signals stored on the computer-readable medium, which signals define appropriate instructions. These instructions, as a result of being executed by a computer, instruct the computer to perform the acts described above for this embodiment.

In yet another embodiment, provided is a method of visually indicating to a user values of a physical property detected over a period of time by sensors located at different predefined distances from a reference point along a spatial dimension of an organism, wherein the period of time includes a plurality of temporal intervals, the method comprising acts of: (A) for a first of the plurality of temporal intervals, for each sensor of at least a subset of the sensors, visually indicating a respective value of the physical property detected by the sensor during the temporal interval on a coordinate of a temporal plot having a temporal axis representing time, the coordinate having a temporal position relative to the temporal axis that corresponds to the temporal interval; (B) repeating act (A) for a next one or more of the plurality of temporal intervals in sequence, including concurrently visually indicating to the user on the temporal plot the values detected by the sensors during the one or more next temporal intervals and the values detected by the sensors during the first temporal interval, and (C) for each performance of act (A), visually indicating sensor identifiers to the user along the spatial axis of the temporal plot, each sensor identifier identifying a position along the spatial axis of the sensor of a respective one of the sensors of the subset.

This embodiment and/or aspects thereof may be implemented as a computer program product that includes a computer-readable medium and computer-readable signals stored on the computer-readable medium, which signals define appropriate instructions. These instructions, as a result of being executed by a computer, instruct the computer to perform the acts described above for this embodiment.

In another embodiment, provided is a method of visually indicating to a user values of a physical property detected over a period of time by sensors located at different predefined distances from a reference point along a spatial dimension of an organism, wherein the period of time includes a plurality of temporal intervals, the method comprising acts of: (A) for a first of the plurality of temporal intervals, subtracting a first value detected by one of the sensors during one of the plurality of temporal intervals from a respective value of the physical property detected by each of a plurality of the sensors during the temporal interval to produce a reduced value for each of the plurality of the sensors; (B) visually indicating each reduced value on a plot having a spatial axis representing the spatial dimension, including visually indicating each reduced value at a coordinate of the temporal plot having a spatial position relative to the spatial axis that corresponds to the predefined distance along the spatial dimension at which the sensor corresponding to the reduced value is located; and (C) repeating acts (A) and (B) for a next one or more of the plurality of temporal intervals in sequence.

This embodiment and/or aspects thereof may be implemented as a computer program product that includes a computer-readable medium and computer-readable signals stored on the computer-readable medium, which signals define appropriate instructions. These instructions, as a result of being executed by a computer, instruct the computer to perform the acts described above for this embodiment.

In another embodiment, provided is a method of visually indicating to a user values of a physical property detected over a period of time by sensors located at different predefined distances from a reference point along a spatial dimension of an organism, wherein the period of time includes a plurality of temporal intervals, and wherein each of the sensors are separated by a predefined distance from one or more nearest other sensors, the method comprising acts of: (A) for a first of the plurality of temporal intervals, for a pair of adjacent sensors of a plurality of the sensors, interpolating a value of the physical property at a distance from the reference point between the pair of sensors based at least on the values of the physical property detected by the pair of sensors during the temporal interval; (B) for the first temporal interval, visually indicating the interpolated value and a respective value of the physical property detected from each of the plurality of the sensors during the first temporal interval to the user on a plot having a spatial axis representing the spatial dimension, including visually indicating each value at a coordinate of the profile plot having a spatial position relative to the spatial axis that corresponds to the predefined distance along the spatial dimension at which the sensor from which the value was detected is located and visually indicating the interpolated value at a spatial position relative to the spatial axis that corresponds to the distance from the reference point between the pair of sensors; and (C) repeating acts (A) and (B) for a next one or more temporal intervals, including, for each performance of act (C), replacing the visual indication of the interpolated value and the value detected by each sensor for a temporal interval with the visual indication of the interpolated value and the value detected by the sensor, respectively, during a next temporal interval.

This embodiment and/or aspects thereof may be implemented as a computer program product that includes a computer-readable medium and computer-readable signals stored on the computer-readable medium, which signals define appropriate instructions. These instructions, as a result of being executed by a computer, instruct the computer to perform the acts described above for this embodiment.

In yet another embodiment, provided is a method of visually indicating to a user values of a physical property detected over a period of time by sensors located at different predefined distances from a reference point along a spatial dimension of an organism, wherein the period of time includes a plurality of temporal intervals, the method comprising acts of: (A) for a first of the plurality of temporal intervals, receiving a respective value of the physical property detected from each of a plurality of the sensors during the first temporal interval and not receiving a value for one of the sensors located between two of the plurality of the sensors; (B) interpolating a value for the one sensor based at least on the values of the physical property detected by the two sensors during the temporal interval; (C) for the first temporal interval, visually indicating the interpolated value and a respective value of the physical property detected from each of the plurality of the sensors during the first temporal interval to the user on a plot having a spatial axis representing the spatial dimension, including visually indicating each value at a coordinate of the profile plot having a spatial position relative to the spatial axis that corresponds to the predefined distance along the spatial dimension at which the sensor from which the value was detected is located and visually indicating the interpolated value at a spatial position relative to the spatial axis that corresponds to the predefined distance along the spatial dimension at which the one sensor is located; and (D) repeating acts (A), (B) and (C) for a next one or more temporal intervals.

In yet another embodiment, provided is a system for visually indicating to a user values of a physical property detected over a period of time of an organism, the period of time including a plurality of temporal intervals. The system comprises a detection component including a plurality of solid state sensors, where each solid state sensor is located at a different predefined distance from a reference point along a spatial dimension within the organism. Each solid state sensor is operable to detect a value of the physical property at the location of the solid state sensor during each of the plurality of temporal intervals, and each solid state sensor is separated from a nearest of the other solid state sensors by approximately 1.0 centimeters. The system also includes a visualization component to receive, for each of the plurality of temporal intervals, the values detected by the solid state sensors, and to control visual indications of the detected values on a plot having a spatial axis representing the spatial dimension, the visual indication including visually indicating each value at a coordinate of the profile plot having a spatial position relative to the spatial axis that corresponds to the predefined distance along the spatial dimension at which the solid state sensor from which the value was detected is located.

In yet another embodiment, provided is a method of determining a distance from a reference point along a spatial dimension within the organism at which an anatomical landmark is located based on values of a physical property detected over a period of time by sensors located at different predefined distances from the reference point along the spatial dimension within the organism, the period of time including a plurality of temporal intervals, wherein each sensor has an associated temporal set of values of the physical property detected at the predefined distance at which the sensor is located, each value of the temporal set representing a value of the physical property detected during a different one of the temporal intervals, the method comprising acts of:(A) for each temporal set, determining an average value of the values of the temporal set; (B) based on the determined averages, generating a spatial function defining values of the physical property as a function of distance along the spatial dimension; and (C) determining a local maximum of the spatial function, wherein the anatomical landmark is located at the determined local maximum.

This embodiment and/or aspects thereof may be implemented as a computer program product that includes a computer-readable medium and computer-readable signals stored on the computer-readable medium, which signals define appropriate instructions. These instructions, as a result of being executed by a computer, instruct the computer to perform the acts described above for this embodiment.

Other advantages, novel features, and objects of the invention, and aspects and embodiments thereof, will become apparent from the following detailed description of the invention, including aspects and embodiments thereof, when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment or aspect of the invention shown where illustration is not necessary to allow those of ordinary skill in the art to understand the invention.

BRIEF DESCRIPTION OF THE DRAWINGS

FIG. 30 is a block diagram illustrating an example of a computer system; and.

DETAILED DESCRIPTION OF THE INVENTION

Although aspects of the invention described below are described primarily in relation to visually indicating values of physical properties (e.g., pressure, pH level, temperature, voltage, tissue impedance) detected from an organism (e.g., a human), or values derived therefrom, over time, such aspects are not limited thereto, but apply to visually indicating any types of values over time. Further, although aspects of the invention described below are described primarily in relation to visually indicating values of physical properties detected within the upper GI tract, such aspects are not limited thereto, but apply to visually indicating physical properties detected within other organs or combinations of organs, including tubular organs, located within an organism, for example, the duodenum, small bowel, bile duct, colon, Sphincter of Oddi, anus or rectum. Further, such values may be detected along a spatial dimension external to an organism, for example, on an exterior surface of an organism.

The function and advantage of these and other embodiments of the present invention will be more fully understood from the examples described below. The following examples are intended to facilitate an understanding of aspects of the present invention and their benefits, but do not exemplify the full scope of the invention.

Figure 1:
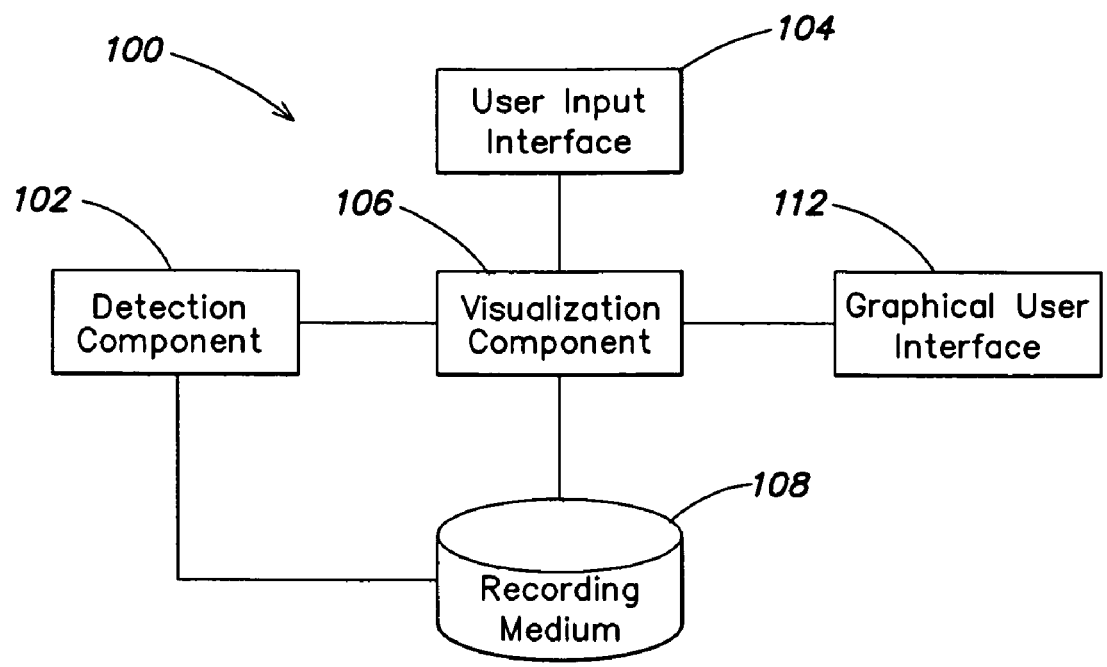
FIG. 1 is a block diagram illustrating an example of a system for visually indicating values detected over a period of time to a user.

FIG. 1 is a block diagram illustrating an example of a system 100 for visually indicating values detected over a period of time to a user. System 100 may include any of a detection component 102, a user input interface 104, a visual component 106, a recording medium 108 and a graphical user interface (GUI) 112. As used herein, a GUI is a user interface on which information is displayed graphically. The detection component 102 may detect values of an organism (e.g., from within an organism) over a period of time and provide such values to a visualization component 106 and/or a recording medium 108. For example, as will be described in more detail below, if the values are to be visually indicated in real time, then the detected values are provided to at least the visualization component 106 and also may be persisted in a recording medium 108. If the detected values are not to be visually indicated in real time, but are to be visually indicated post hoc at a later point in time, then the detection component 102 may provide the detected values to the recording medium 108 but not to the visualization component 106.

Visualization component 106 may be operable to receive detected values from detection component 102 (e.g., for real time visual indication) and from recording medium 108 (e.g., for post hoc visual indication). Further, the visualization component may be operable to send information to be persisted to the recording medium during or after visually indicating values to a user. Such information may include the values themselves, display information such as values for display parameters, locations of anatomical landmarks, locations of a probe (e.g., catheter) with respect to an organism, interpolated values, etc. The visualization component 106 also may be operable to receive user input from user input interface 104. The user input interface 104 may include any of a variety of interfaces to user input devices, for example, a mouse, a keyboard, a microphone (e.g., in combination with a voice recognition system), or a touch screen. The visualization component 106 may include a variety of logic for generating information to send to the graphical user interface 112 from the received detected values and received user input.

Figure 2:
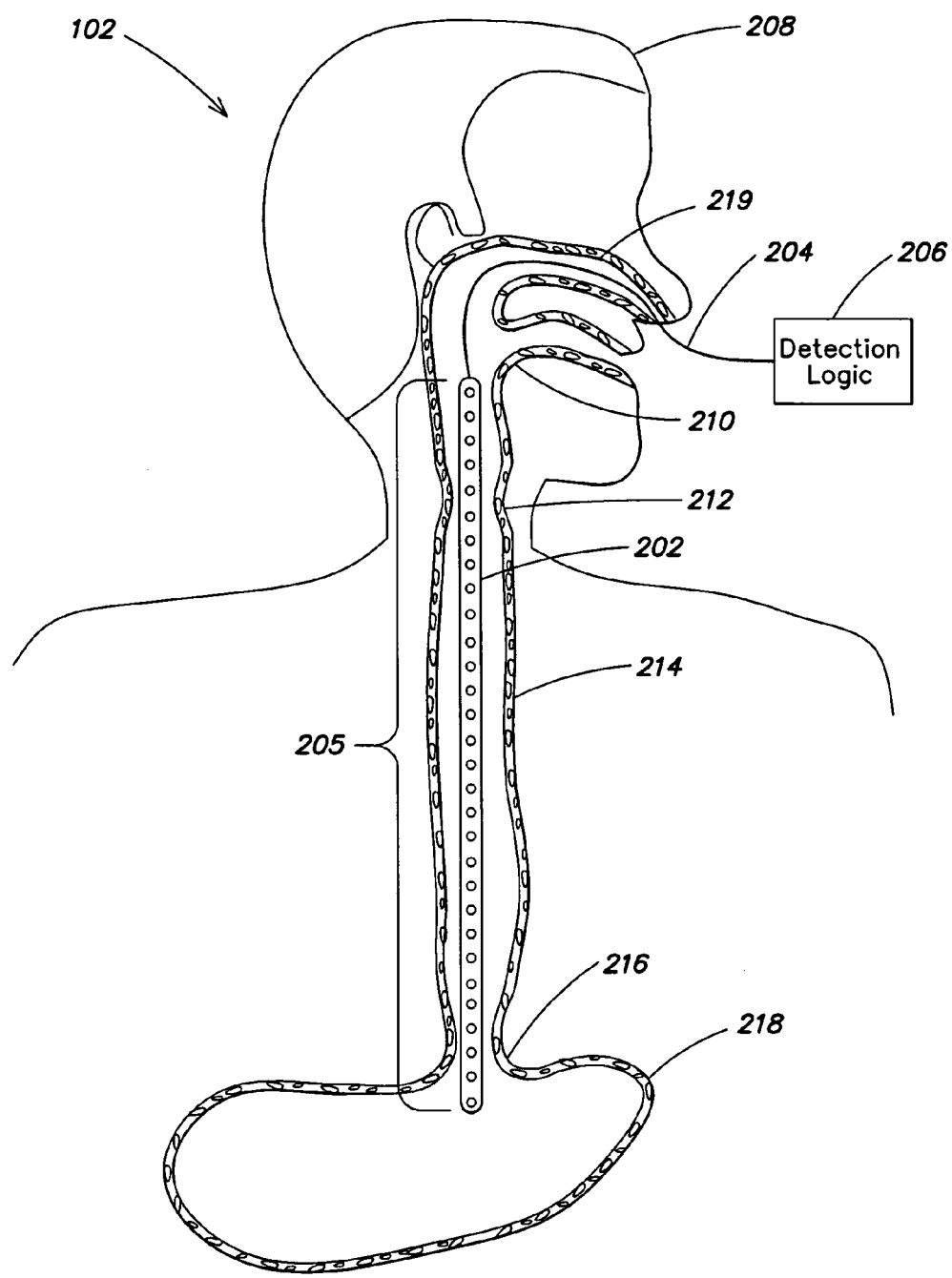
FIG. 2 is a block diagram illustrating an example of a detection component of a system for visually indicating detected values to a user.

FIG. 2 is a block diagram illustrating an example of a detection component 102. The detection component 102 may include any of detection logic 206, transmission medium 204, a plurality of sensors 205 and a probe (e.g., catheter) 202 to which the sensors 205 may be attached or in which the sensors 205 may be embedded. The sensors 205 may be any of a variety of types of sensors, for example, pressure sensors such as a capacitive pressure sensors, for example, sensors 205 may be an array of sensors as described in commonly-owned co-pending Patent Cooperation Treaty application entitled "Array Sensor Electronics" by Son et al., filed on even date herewith bearing Ser. No. 10/493,459 (hereinafter the Son application). Such pressure sensors may be capable of detecting pressure in response to contact with tissue of an organism.

The transmission medium 204 may be any of a plurality of types of transmission mediums, such as a group of wires (e.g., a bus), a wire, a cable, an optical fiber, a group of optical fibers or a wireless transmission medium (e.g., air). The transmission medium 204 may carry control and addressing signals from the detection logic to the sensors 205 and may carry detected values from the sensors 205 to the detection logic 206.

In an embodiment, the plurality of sensors 205 are a linear array of nine or more sensors, for example, twenty-two or more sensors such as thirty-six sensors or even more. If there are thirty-six sensors, the transmission medium 205 may include six input wires and six output wires, and the detection logic 206 may be configured to control the multiplexing of detected values along the output wires. For example, a detection cycle may be divided into six sub-cycles, where, for each sub-cycle, six detected values are received on six respective output lines. Thus, after six sub-cycles the values detected by all 36 sensors have been read. For each sub-cycle, the detection logic may use one of the six input lines to select six of the thirty-six sensors. In an aspect of the invention, a detection cycle has a frequency greater than fifteen hertz, for example, forty hertz or greater such as two hundred hertz or even more. Accordingly, in such aspects where signals detected by thirty-six sensors are being multiplexed during six sub-cycles, the frequency of the sub-cycles may be greater than ninety hertz, for example, two hundred forty hertz or greater such as 1.2 kilohertz or even greater.

The detection logic 206 also may include signal processing logic to process the signals carrying the values received over transmission medium 204. For example, the signal process logic may include noise filtering logic, analog-to-digital conversion logic and other logic to convert the raw detected values into suitable form to be input to visualization component 106. Detection logic 206 may include any of the logic described in the Son application.

As is shown in FIG. 2, the probe 202 and sensors 205 of the detection component 102 may be inserted within a human 208 or another organism. For example, the probe may be inserted through the nasal cavity 219 into the upper GI tract such that at least a portion of the probe 202 resides in the pharynx 210, the UES 212, the esophagus 214, the LES 216 and the stomach 218. Although FIG. 2 illustrates the probe inserted within the upper GI tract, the probe may be inserted in any of a variety of combination of organs, including tubular organs. For example, the probe 202 may be inserted in the duodenum, the small bowel, the bile duct, the colon, the Sphincter of Oddi, the anus or the rectum.

Each sensor may be arranged to be spaced a predefined distance from a nearest one or more other sensors. Optionally, the spacing between each pair of sensors may be configured to be approximately the same. In an aspect of the invention, this same spacing may be three centimeters or less, for example, two centimeters or less such as one centimeter, or even less than one centimeter.

The sensors 205 may be configured to sense any of a variety of physical properties, for example, pressure, pH, temperature, voltage, tissue impedance, another physical property or any combination thereof.

Figure 3:
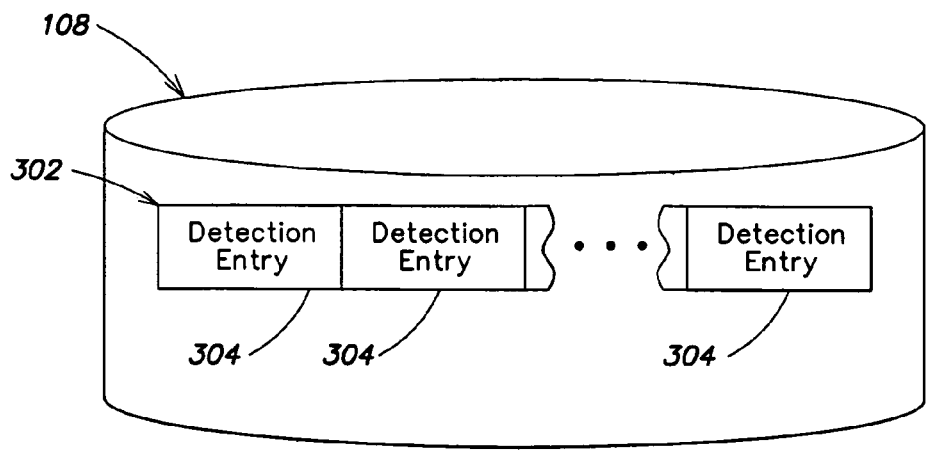
FIG. 3 is a block diagram illustrating a collection of detection entries stored on a recording medium.

FIG. 3 is a block diagram illustrating an example of a collection of detection entries 302 stored in a storage medium 108. Each detection entry 304 may include values of a physical property detected from an organism over a period of time. The collection 302 may be any of a plurality of types of databases, for example, an object-oriented database, a relational database, a flat file database, a combination thereof, or any of a variety of other types of databases.

Figure 4:
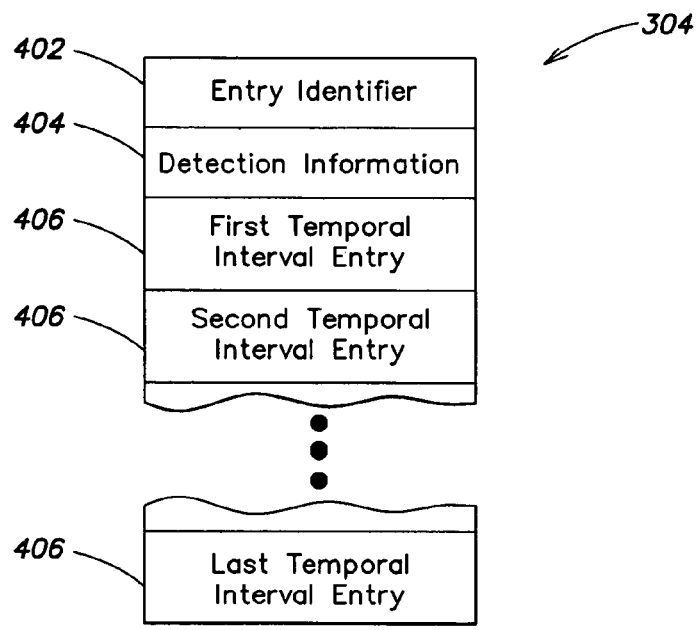
FIG. 4 is a block diagram illustrating an example of a detection entry.

FIG. 4 is a block diagram illustrating an example of a data structure of a detection entry 304. Each detection entry 304 may include an entry identifier 402, detection information 404 and a plurality of temporal interval entries 406. The entry identifier 402 may identify the detection entry and the detection information 404 may include information about the detection entry. For example, detection information 404 may include a name of a patient from which the values of the physical property were detected, a date on which the information was detected, the duration of the detection, the part of the body from which values were detected, the physician that detected the values from the patient, or any of a variety of other information.

Figure 5:
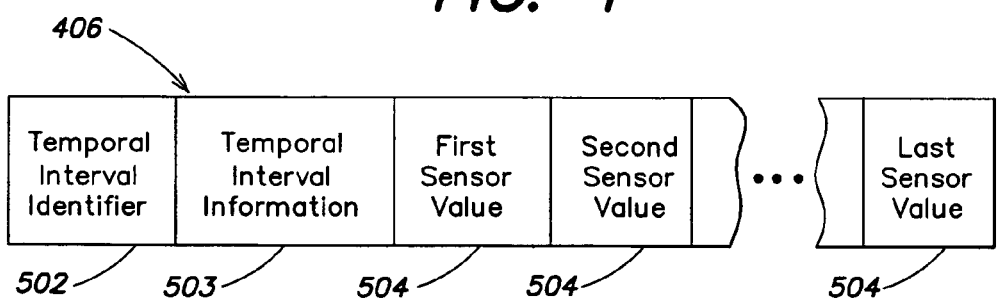
FIG. 5 is a block diagram illustrating an example of a temporal interval entry of a detection entry.

FIG. 5 illustrates an example of a temporal interval entry 406. Each temporal interval entry 406 may include a temporal interval identifier 502 that uniquely identifies the temporal interval in the context of the detection entry 304 to which the interval information belongs. For example, the temporal interval identifier may be a time at which the temporal interval was detected.

The temporal interval entry 406 further may include temporal interval information 503. Information 503 may include any information pertaining to the temporal interval, for example, any of the information described herein, including, but not limited to, a probe (e.g., catheter) position within an organism during the temporal interval, annotations made for the temporal interval, locations of anatomical landmarks during the temporal interval, identifications of the technique used to display the values on the temporal plot and/or profile plot during the temporal interval, values interpolated during the temporal interval, etc.

The temporal interval entry 406 may further include sensor values 504 that each represent a value of a physical property detected during the temporal interval identified by temporal interval identifier 502. Although the arrangement of information illustrated in FIGS. 4 and 5 for a detection entry 304 has been described in the context of storage medium 108, it should be understood that the same arrangement of information may be employed by other aspects of the system 100, for example, the visualization component 106, which may be operable to store such information locally, for example, on a non-volatile recording medium (e.g., random access memory (RAM)).

Figure 6:
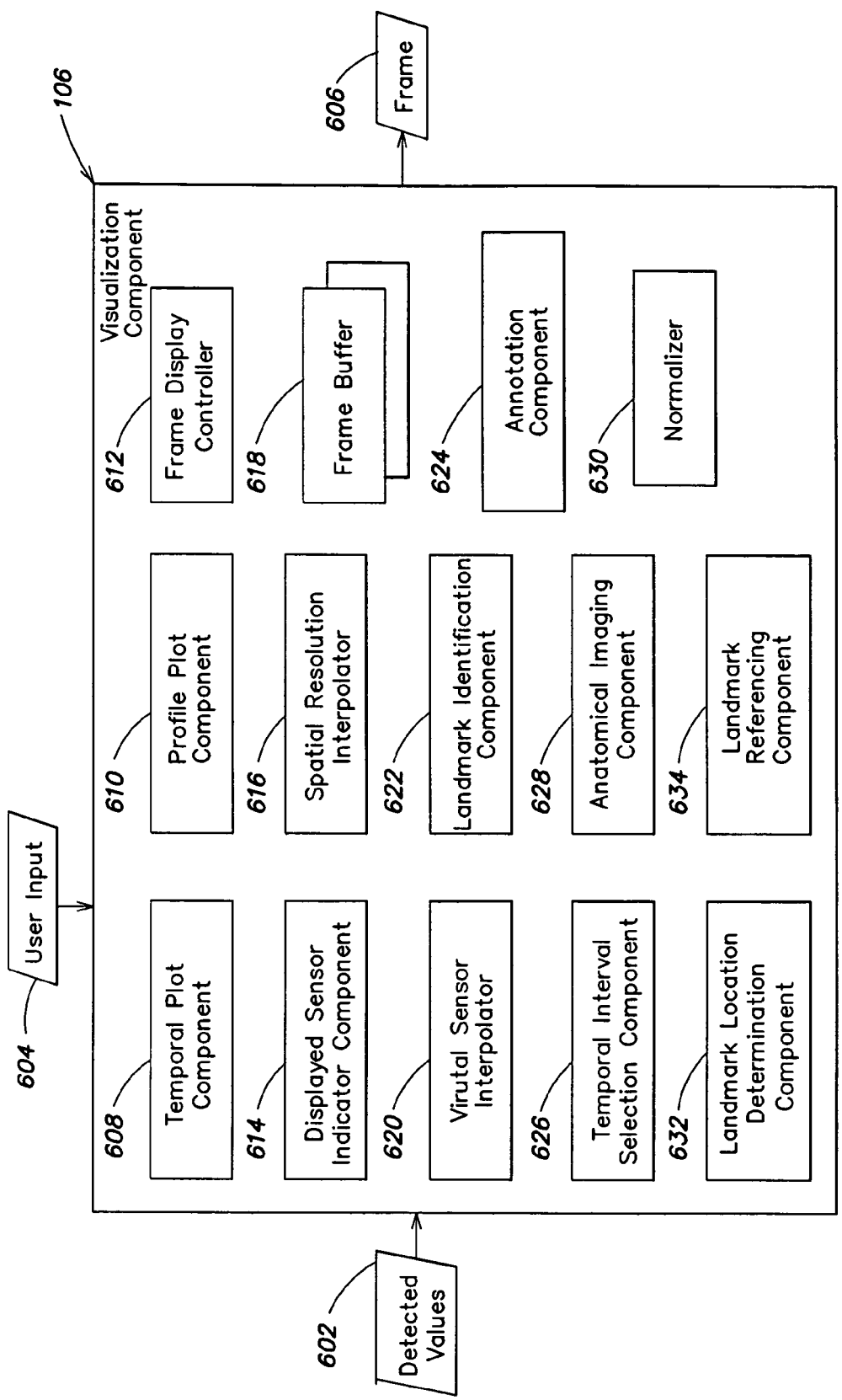
FIG. 6 is a block diagram illustrating an example of a visualization component of a system for visually illustrating values detected over a period of time to a user.

FIG. 6 is a block diagram illustrating an example of the visualization component 106. The visualization component 106 may be configured to receive detected values 602 and user input 604 and output a frame 606 of information to be displayed by a display mechanism, for example, a graphical user interface (GUI) 112 displayed on a display screen connected to a computer. Visualization component 106 may include any of a variety of logical components, including any of temporal plot component 608, profile plot component 610, frame display controller 612, displayed sensor identifier component 614, spatial resolution interpolator 616, frame buffer 618, virtual sensor interpolator 620, landmark identification component 622, annotation component 624, temporal interval selection component 626, anatomical imaging component 628, normalizer 630, landmark location identifier component 632, landmark referencing component 634 and any of a variety of other components.

Frame display controller 612 receives information output from one or more of the other components of visualization component 106, composes a frame of display information and outputs frames 606. As will be described in more detail below, several of the operations performed by the components included within visualization component 106 may be performed in real time. The frame display controller 62 assists in this real time implementation.

The detected values 602 may be received at a faster rate than the rate at which a GUI is redrawn or refreshed (e.g., ten to fifteen frames per second). The detection component 102 may be configured to sample a set of values (e.g., corresponding to a temporal interval) from sensors 205 at any of a variety of rates, for example, any of the variety of rates at which the sensors described above detect values, for example, a rate ranging from approximately twenty to two hundred sets of values per second. A timer may control the rate at which one or more of the components of the visualization component 106 receive the detected values to perform calculations. User inputs 604 may be received asynchronously and may be input to one or more of the components within the visualization component 106. For each set of values, operations may be performed on the sets of values by one or more of the components of visualization component 106 (one or more of which may be configured according to a user input 604), and the results of these operation may be sent to frame display controller 612. Frame display controller 612 may generate a complete display frame based on these results and store the display frame in frame buffer 618 while operations are performed on a next set of values. Frame buffer 618 may be any of a plurality of types of memory buffers, for example, a circular buffer. When the GUI is to be refreshed (e.g., once every ten to fifteen seconds), the frame display controller may access the most recently stored frame in the frame buffer 618 and control a transfer of the frame from frame buffer 618 to the GUI.

Visualization component 106, and logical components thereof, may be implemented using software (e.g., C, C#, C++, Java, or a combination thereof), hardware (e.g., one or more application-specific integrated circuits), firmware (e.g., electrically-programmed memory) or any combination thereof.

One or more of the components of system 100, including visualization component 106, may reside on a single system, or one or more components may reside on separate, discrete systems. Further, each component may be distributed across multiple systems, and one or more of the systems may be interconnected.

Further, on each of the one or more systems that include one or more components of system 100 and/or visualization component 106, each of the components may reside in one or more locations on the system. For example, different portions of the components may reside in different areas of memory (e.g., RAM, ROM, disk, etc.) on the system. Each of such one or more systems may include, among other components, a plurality of known components such as one or more processors, a memory system, a disk storage system, one or more network interfaces, and one or more busses or other internal communication links interconnecting the various components.

System 100 and visualization component 106 may be implemented on a computer system described below in relation to FIGS. 30 and 31.

System 100, including visualization component 106, is merely an illustrative embodiment of a system for detecting and visually indicating values detected over a period of time along a first dimension of an organism. Such an illustrative embodiment is not intended to limit the scope of the invention, as any of numerous other implementations of a system for visually indicating values detected over a period of time along a first dimension of an organism, for example, variations of a system 100 and visualization component 106, are possible and are intended to fall within the scope of the invention. None of the claims set forth below are intended to be limited to any particular implementation of a system for visually indicating values detected over a period of time along a first dimension of an organism unless such claim includes a limitation explicitly reciting a particular implementation.

Several of the visualization component 106 are described in more detail below. Methods that may be performed by these logical components will now be described.

Figure 7:
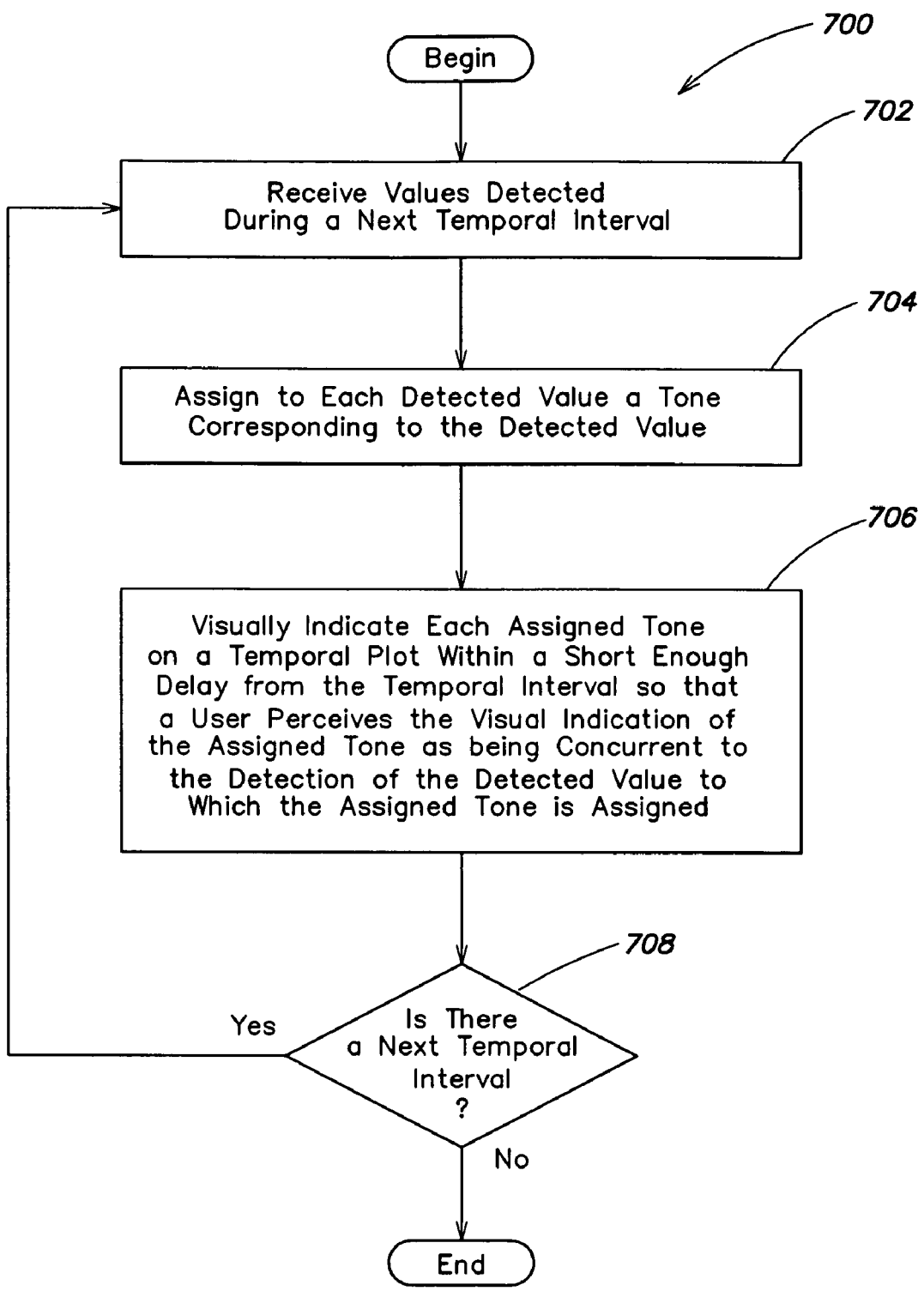
FIG. 7 is a flow chart illustrating an example of a method of visually indicating values detected over a period of time to a user in real time on a temporal plot using a contour technique.

FIG. 7 is a flow chart illustrating an example of a method of visually indicating values detected over a period of time along a dimension to a user in real time on a temporal plot using a contour technique. In Act 702, values detected during a next temporal interval may be received. For a first pass through acts 702-708, the next temporal interval may be a first temporal interval.

Next, in Act 704, for each detected value, a tone corresponding to the detected value may be assigned to the detected value. As used herein, a "tone" may be a color or grayscale value. For example, the range of possible values of a detected value may be divided into a plurality of sub-ranges, and a different tone may be delegated to each sub-range. The number of sub-ranges and, consequently, the number of tones to be delegated, may be configured based on the desired granularity of the tones visually indicated to a user. For example, if the detected physical property is pressure, the range of detected values may be from negative fifty millimeters mercury (mmHg) to two hundred mmHg. This range of values may be divided into any of a number of sub-ranges, for example, one thousand twenty-four, five hundred twelve, two hundred fifty-six, etc., with a tone delegated to each sub-range.

As will be described in more detail below, method 700 also may include additional acts, performed prior to Act 704, of interpolating values for one or more sensors for which values were not detected during a temporal interval (e.g., due to sensor failure), and interpolating values for locations between locations of sensors to increase the spatial resolution of values to be displayed. As part of Act 704, tones may be assigned to these interpolated values.

In a following Act 706, each assigned value may be visually indicated on a temporal plot in real time. For example, as described above with respect to FIG. 6, a new frame may be displayed to the user at a rate of ten frames per second or greater such that each detected value is visually indicated to the user within 0.1 seconds or less, for example, within 0.66 seconds or even less.

In Act 708, it may be determined whether there is a next temporal interval. If there is not a next temporal interval, then method 700 may end. If there is a next temporal interval, then method 700 may return to Act 702. Thus Acts 702-708 may be repeated until the values detected during each temporal interval have been visually indicated to the user. Alternatively, an instruction may be received to stop method 700, for example, from a user.

The detected values may be values of a physical property detected over a period of time by sensors located at different predefined distances from a reference point along a dimension of an organism, for example, a human. The sensors may be located at different locations within one or more organs of the organism, for example, within the upper GI tract, duodenum, small bowel, bile duct, colon, Sphincter of Oddi, anus, rectum, or any of the variety of other organs. The detected physical property may be any of a variety of physical properties, including, but not limited to, pressure, pH, tissue impedance, temperature, voltage, another physical property or any combination thereof.

The temporal plot on which the assigned values are displayed may have a temporal axis representing time and may have a spatial axis, oriented or orthogonally to the temporal axis, representing the dimension. If a contour technique is used, each assigned value may be indicated as a tone at a spatial position of the temporal plot corresponding to the location of the sensor within the organism from which the detected value corresponding to the tone was detected.

For each temporal interval, the assigned values for the temporal interval may be visually indicated on the temporal plot concurrently to assigned values of previous temporal intervals so that a user can observe a history of values detected by the sensors over time.

In an embodiment of method 700, prior to each performance of Act 706 for a temporal interval, the temporal position of the coordinate at which each tone from previous temporal intervals is visually indicated may be shifted in a first direction by an amount corresponding to a duration of each temporal interval. This shifting of temporal positions results in the user perceiving the visual indications of the values as moving in the first direction along the temporal axis of the temporal plot (e.g., right to left). This technique of shifting the temporal position of a tone to be indicated to a user so that the user perceives the assigned tones as moving in a first direction along the temporal plot is referred to herein as a moving contour technique. A temporal plot on which a moving contour technique is being employed is referred to herein as a moving contour plot.

Acts 702-706 may be performed at a predefined rate (e.g., ten hertz or more, for example, fifteen hertz, or even greater) such that a user perceives the repeated performances of Acts 702-706 as being temporally continuous, as opposed to being temporally discrete. In other words, a user will observe a smooth transition between temporal intervals as opposed to observing a choppy transition between temporal intervals.

Further, for consecutive temporal intervals, the values detected during one of the consecutive temporal intervals may be visually indicated at a predefined proximity to the values detected during the other of the consecutive temporal intervals such that a user perceives the visual indications of the values of the consecutive sets as being spatially continuous along the temporal axis.

It should be appreciated that although method 700 is described above primarily in relation to visually indicating values in real time, the method 700 may be applied analogously to visually indicating detected values post hoc.

Further, many of the aspects of the invention described with respect to visually indicating values detected over a period of tine on a temporal plot using a contour technique also apply to visually indicating the detected values on a profile plot using a contour technique, or on either the temporal plot or the profile plot using any of a variety of the techniques described herein.

Figure 8:
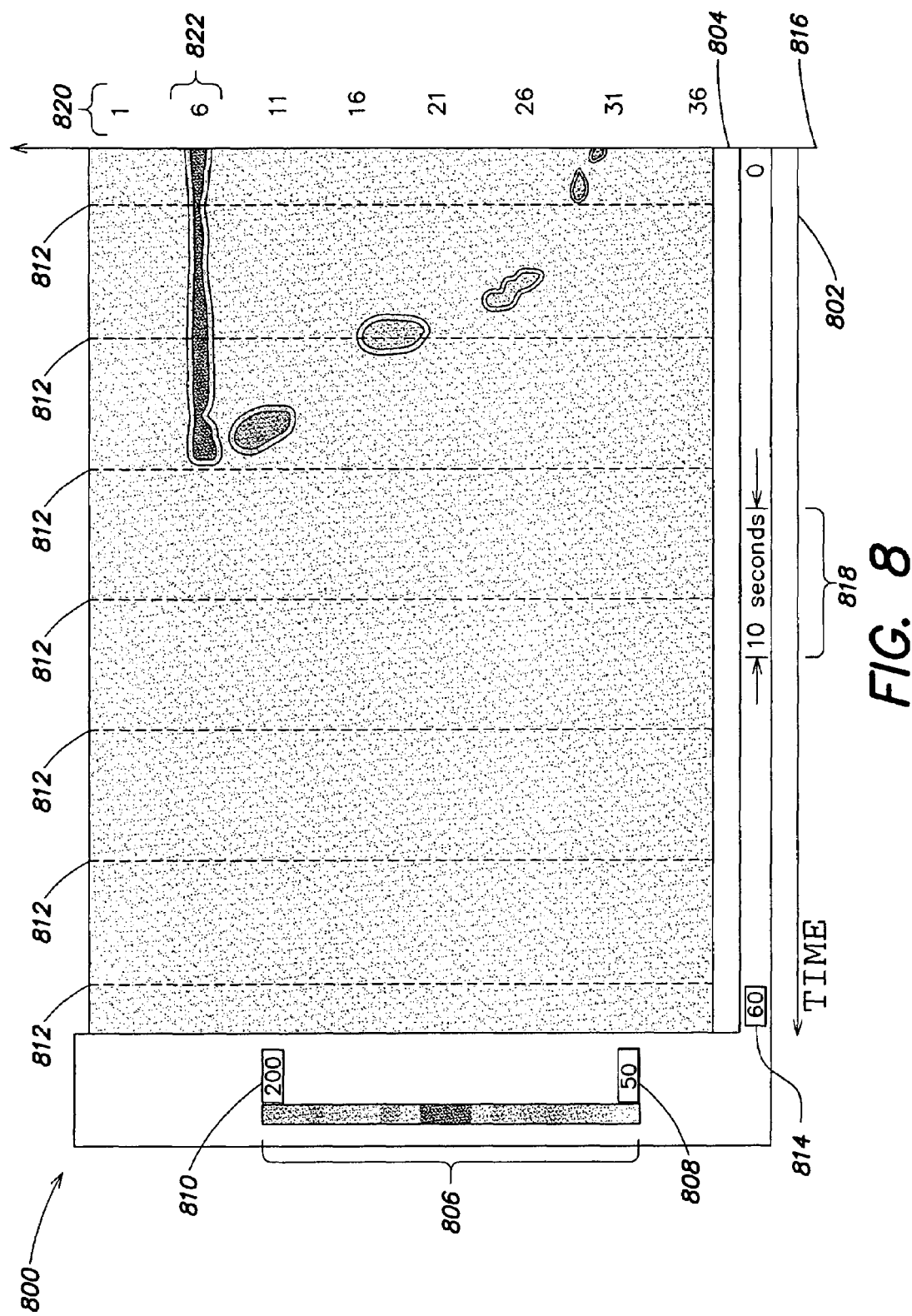
FIG. 8. is an example of a temporal plot visually indicating values detected over a period of time using a contour technique.

FIG. 8 is an example of a temporal plot 800 visually indicating values detected over a period of time using a contour technique in real time or post hoc. Plot 800 may be a moving contour plot. Such plot may be generated by one or more logical components of visualization component 106, including temporal plot component 608.

Moving contour plot 800 may include a temporal axis 802 representing time and a spatial axis 804 representing a distance along a dimension of an organism. These axes may not actually be displayed on temporal plot 800, but are used herein for illustrative purposes. The plot 800 may include a tone key 806 indicating the tones delegated to sub-ranges between a low threshold 808 and a high threshold 810. The plot 800 also may include a sub-period indicator 818 indicating to a user the duration of time delimited by sub-period delimiters 112.

Plot 800 also may include temporal duration indicator 814, which indicates the duration of time being displayed on plot 800. Indicator 814 may be configured as a control of a GUI that enables a user to change the displayed duration of time, which changes the temporal density of the information visually indicated along temporal axis 802. In response to changing the value of the temporal duration using temporal duration indicator 814, sub-period delimiters 812 and sub-period indicator 818 may be changed accordingly.

Plot 800 may include spatial indicators 820, where each spatial indicator indicates a location along a dimension in the organism from a reference point (e.g., an end of a probe, e.g., catheter) with respect to the spatial axis 804.

The values detected during a plurality of temporal intervals may be visually indicated as tones on plot 800. For example, spatial range 822 illustrates a range along the dimension within the organism for which the detected values vary consistently over a period of approximately twenty-five seconds. In an aspect of plot 800, values detected during a temporal interval may be controlled to move from right to left along temporal axis 816. In this aspect, the values detected during a temporal interval may be first visually indicated on plot 800 at a temporal position along the temporal axis 802 nearest to temporal origin 816 (e.g., a column of pixels of a display screen closest to the origin 816). The location along the dimension at which a visually indicated value was detected can be determined with reference to the sensor location 820 along the spatial axis 804, for example, if the sensors are spaced a predefined distance apart from one another, for example, one cm as described above with respect to FIG. 2. In the aspect illustrated by plot 800, sensor location indicators 820 indicate that there are at least thirty-six sensors from which values may be detected.

FIG. 8 may be a temporal plot of pressure values detected along an upper GI tract (e.g., pressure resulting from contact with the tissue of the upper GI tract) of a human while a human is swallowing water or another fluid. As can be seen in plot 800, there is a relatively continuous high pressure in a location of the upper GI tract approximate to sensor "6". This location may be the location of the UES. Further, relatively high pressure indications descend down the upper GI tract over a period time. This pressure may correspond to muscle contractions along the upper GI tract that occur as the liquid is swallowed.

Temporal plot 800 may include additional features such as those described below in relation to FIG. 11.

Although method 700 is described above with respect to visually indicating values on a temporal plot, a similar method may be applied to visually indicate detected values on a profile plot. For example, each detected value may be visually indicated using an assigned tone on a profile plot having a spatial axis, at a spatial position relative to the spatial axis that corresponds to the location of a sensor from which the detected value was detected. Thus, values detected by sensors along a dimension of an organism over time may be visually indicated on a profile plot using a contour technique. In contrast to displaying values on a temporal plot using a contour technique, on a profile plot, only values detected during a single temporal interval may be visually indicated at any given time. In other words, values detected during different temporal intervals may not be displayed concurrently.

Figure 9:
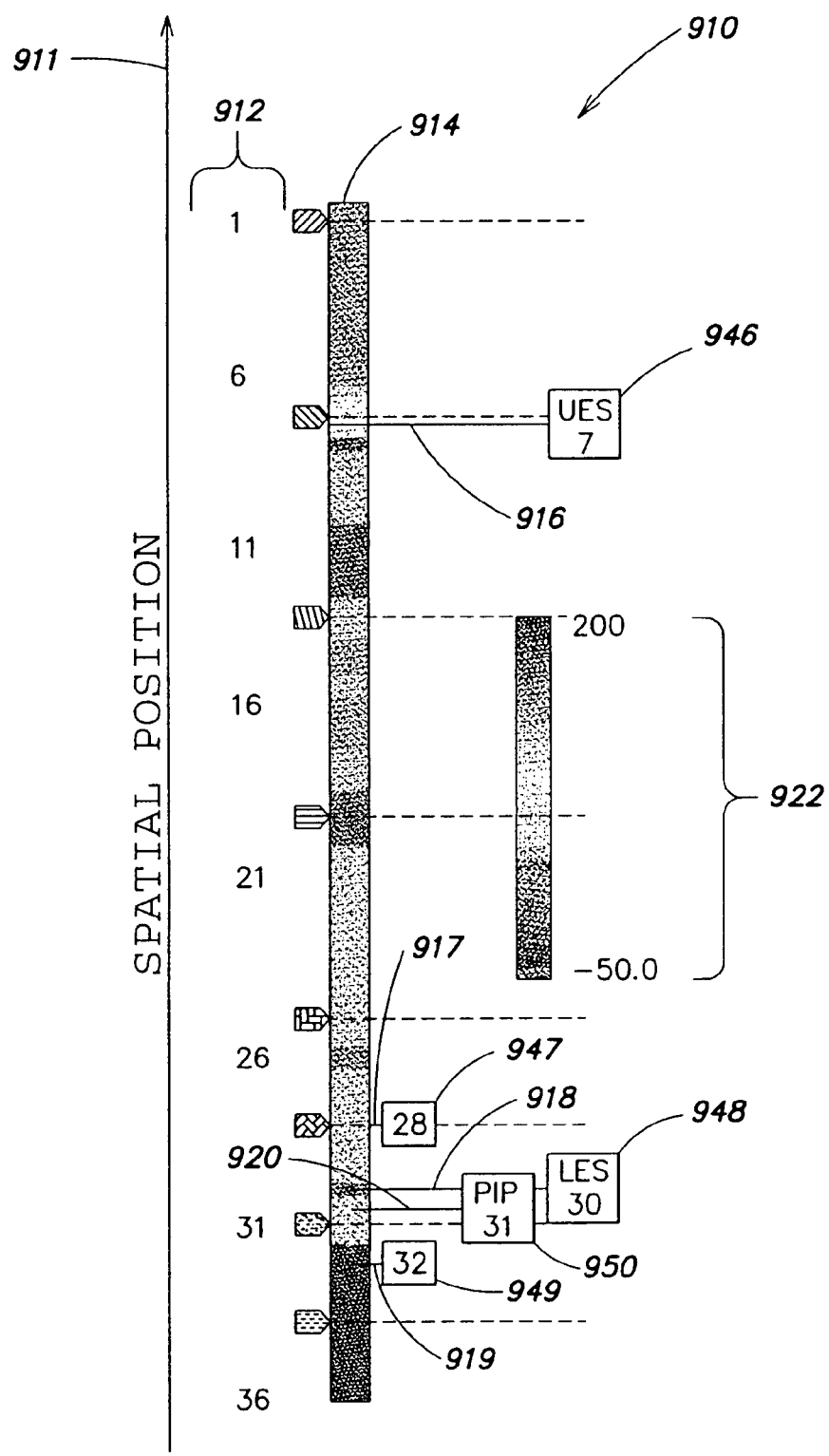
FIG. 9 is an example of a profile plot visually indicating values detected over a period of time using a contour technique.

FIG. 9 is an example of a profile plot 910 visually indicating values detected over a period of time using a contour technique. Profile plot 910 may include any of spatial axis 911, tone bar 914, tone key 922, and one or more anatomical landmark location indicators, including any of UES indicator 916, LES indicator 918, LES upper margin indicator 917, LES lower margin indicator 919 and PIP indicator 920. Although used herein to illustrate profile plot 910, spatial axis 911 may not actually be visually indicated as part of profile plot 910.

Similar to as described above with respect to temporal plot 800, spatial indicators 912 may indicate a location along a first dimension of an organism relative to spatial axis 911. Tone bar 914 includes the visual indications of the values detected by the sensors using a tone corresponding to the detected value. The spatial position relative to the spatial axis 911 of each tone indicated along tone bar 914 corresponds to the location at which the value corresponding to the tone was detected or the location corresponding to an interpolated value corresponding to the tone.

The thickness of tone bar 914 may not correspond to any physical property, but may be configured as desired to provide visual clarity. The values visually indicated along tone bar 914 may be updated each time a frame is transmitted to the graphical interface that displays profiled plot 910.

It should be appreciated that not every temporal interval may have its values visually indicated on a profile plot such as profile plot 910. As described above, the rate at which values are detected by the sensors may be higher than the rate at which the GUI is refreshed, and the GUI may be refreshed with the most current information. Accordingly, in one aspect, only values detected during temporal intervals that are most recent temporal intervals before a GUI refresh may be visually indicated on a profile plot, and values detected during other temporal intervals may not be visually indicated on the profile plot. Alternatively, the rate of detection and rate of display refresh may be approximately the same, such that the values detected during all temporal intervals may be visually indicated on a profile plot.

Each of the anatomical landmark identifiers (i.e., landmark identifiers) 916-920 may visually indicate a spatial position along spatial axis 911 that corresponds to a location along a first dimension within an organism (e.g., along an upper GI tract) at which an anatomical landmark is located. Each landmark location identifier 916-920 may include a landmark identifier 946-950, respectively. Each location identifier may indicate an identifier of the landmark and also may indicate a numerical value representing either a nearest sensor to the determined location of the landmark or the location itself of the anatomical landmark. For example, UES location identifier 916 has a landmark identifier 946 that identifies the UES and indicates that the location of the UES is closest to sensor "7." Alternatively, the landmark identifier 946 may indicate the location itself of the UES, with a value such as "7.1," which may mean 7.1 centimeters along the dimension of the organism from a reference point.

In an aspect of displaying landmark identifiers on a profile plot, the type of numerical value (e.g., the closest sensor or the location itself) may be selectable, for example, by a user. Accordingly, profile plot 910 may include a control that enables a user to select which type of numerical value will be indicated. In the profile plot 910 illustrated in FIG. 9, each landmark identifier displays a numerical value representing the closest sensor.

Thus, LES location identifier 918, including LES identifier 948, indicates that the LES is located at a location within the upper GI tract for which the closest sensor is sensor "30." LES upper margin location identifier 917, including LES upper margin identifier 947, indicate that, for the location of the LES upper margin, the closest sensor is sensor "28." LES lower margin location identifier 919, including LES lower margin identifier 949, indicate that, for the location of the lower margin identifier, the closest sensor is sensor "32." PIP location identifier 920, including PIP identifier 950, indicate that, for the location of the PIP within the upper GI tract, the closest sensor is sensor "31."

As will be described in more detail below in relation to FIG. 15, for a display including a profile plot and a temporal plot using a contour technique, one or more landmark identifiers may extend from a spatial position along the spatial axis of the profile plot across the temporal plot at a corresponding spatial position along the spatial axis of the temporal plot. Further, a user may be provided the ability to move the spatial position of a landmark location identifier and landmark identifier, for example, by clicking and dragging using a mouse, as will be described in more detail below.

Figure 10:
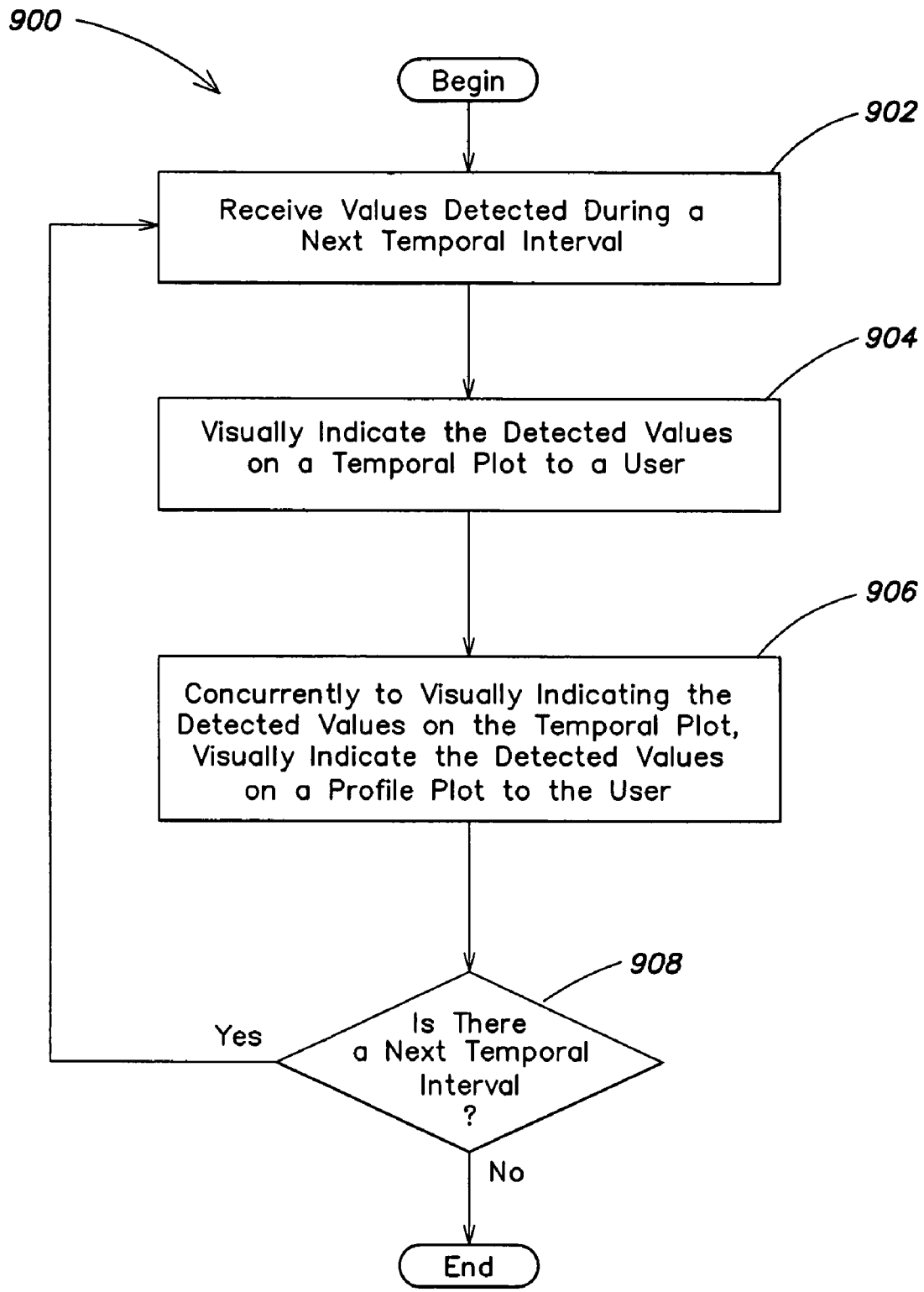
FIG. 10 is a flow chart illustrating an example of a method of visually indicating values detected over a period of time on a temporal plot and a profile plot concurrently.

FIG. 10 is a flow chart illustrating an example of a method 900 of visually indicating values detected over a period of time along a dimension on a temporal plot and a profile plot concurrently, in real time or post hoc. In Act 902, values detected during a next temporal interval (e.g., a first temporal interval) may be received, for example, by a visualization component, from a detection component or a recording medium.

Next, in Act 904, the detected values may be visually indicted on a temporal plot using any of a variety of techniques, for example, any of the techniques described herein.

In Act 906, the detected values may be visually indicated on a profile plot using any of a variety of techniques including any of those described herein, concurrently to visually indicate that the detected values on a temporal plot. Acts 904 and 906 may be performed in real time.

Next, in Act 908, it is determined whether there is a next temporal interval. If there is not a next temporal interval, then method 900 ends, else, method 900 returns to Act 902.

In an aspect of method 900, the temporal plot and the profile plot may be horizontally (i.e., laterally) aligned with respect to one another (i.e., side-by-side) and the spatial axes of the temporal plot and profile plot may be parallel. The spatial axes of the temporal plot and the profile plot both may be oriented vertically on a GUI presented to a user, whether visually indicated in real time or post hoc. Further, the temporal axis of the temporal plot may be oriented horizontally.

Figure 11:
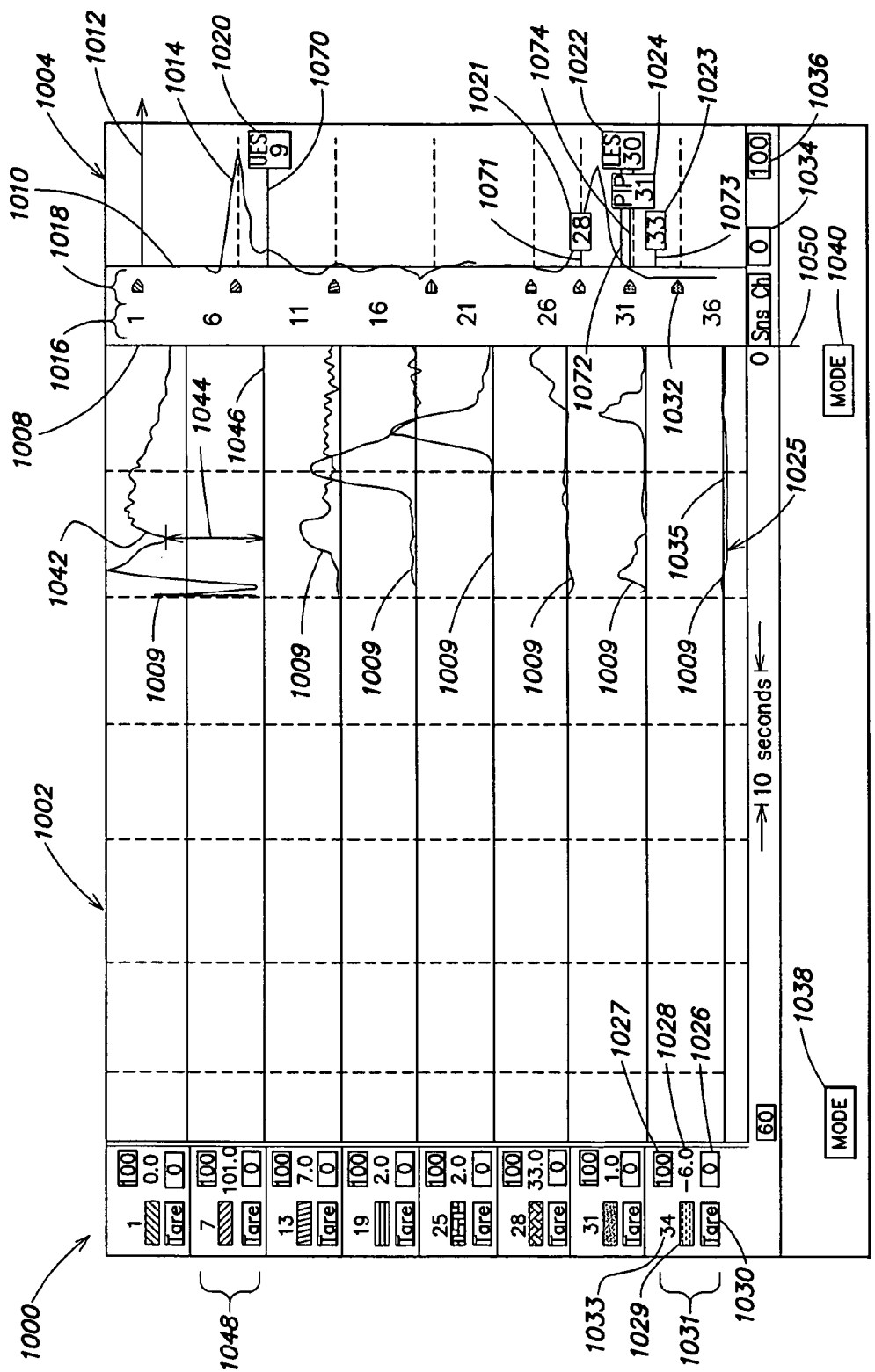
FIG. 11 is an example of a display including a temporal plot and a profile plot visually indicating values detected over a period time concurrently.

FIG. 11 is an example of a display 1000 including a temporal plot 1002 and a profile plot 1004 on which values detected over a period of time along a dimension are visually indicated, concurrently, in real time or post hoc. Display 1000 may be generated by a plurality of the logical components of visualization component 106, as is described in more detail below.

Although FIG. 11 illustrates visually indicating the values on the temporal plot using a line trace technique and visually indicating the values on the profile plot using a line trace technique, this aspect of the invention is not limited to such combination, as either of the temporal plot and profile plot may visually indicate the detected values using any of a variety of techniques, for example, any of the variety of techniques described herein. It should be appreciated that, in an embodiment, display 1000 may include only temporal plot 1002 or may include only profile plot 1004.

As illustrated in FIG. 11, when visually indicating detected values on a temporal plot 1002 using a line tracing technique, it may be desirable to display line traces 1009 of values detected from only a subset of the sensors located within the organism. Visually indicating values detected from only a subset may be desirable because, as the number of sensors for which values are displayed using a line tracing technique increases, the lack of visual clarity to a user also increases. For example, on temporal plot 1002, only eight line traces are displayed.

When values are visually indicated from only a subset of sensors, it may be desirable to provide a user with information regarding each sensor of the subset for which values are being visually indicated.

Accordingly, a display panel may be associated with each sensor of the subset for which values are being visually indicated on temporal plot 1002. For example, a display panel 1031 may be provided for line trace 1025. Panel display 1031 may include a sensor identifier 1033, a sensor swatch 1029, a normalizing toggle button 1030, a high threshold indicator 1027, a baseline value indicator 1026, and a value indicator 1028.

Sensor identifier 1033 indicates that line trace 1025 corresponds to sensor 34. Sensor swatch 1029 indicates atone used to visually indicate line trace 1025. Thus, the sensor swatch 1029 assists a user in associating a sensor display panel with its corresponding line trace. Further, profile plot may include sensor location indicators 1018, which may include a displayed sensor location indicator 1032 corresponding to sensor "34" for which values are visually indicated by line trace 1025. Accordingly, sensor location indicator 1032 may comprise a tone that is the same as the tone of sensor swatch 1029 and line trace 1025.

Normalizing toggle button 1030 may enable a user to toggle between visually indicating values on line trace 1025 using absolute values or visually indicating values on line trace 1025 using values normalized with respect to all of the line traces 1009. Normalizing the values may be beneficial for a clearer visual indication of the line traces 1009 to a user, whereas visually indicating absolute values may be beneficial to the user because the actual value detected by a sensor over a period of time is conveyed to a user.

Baseline value indicator 1026 indicates a value represented by base line 1035 for line trace 1025. As described above, if visually indicating detected values on a temporal plot using a line trace technique, the values are indicated as an offset from a baseline corresponding to the sensor at which the values were detected. For example, line trace 1042 is represented as an offset 1044 from baseline 1046, where the information corresponding to this line trace 1042 is visually indicated on sensor display panel 1048.

High threshold indicator 1027 indicates a high threshold for values visually represented by line trace 1025. In other words, although detected values may exceed the high threshold indicated by high threshold indicator 1027, line trace 1025 will only display values up to the high threshold.

Value indicator 1028 indicates the value currently being visually indicated by line trace 1025 at a particular temporal position along the temporal axis of temporal plot 1002. This particular temporal position may be the temporal axis origin 1050 or another temporal position specified by a user, for example, as described below in relation to FIG. 25.

Profile plot 1002 may include spatial position indicators 1016, displayed channel location indicators 1018, line trace 1014, landmark location identifiers 170-174 and corresponding landmark identifiers 1020-1024, respectively, baseline value indicator 1034, high threshold indicator 1036 and value control.

Spatial position indicators 1016 indicate a distance along the spatial dimension from a reference point. Displayed sensor indicators 1018 visually indicate to a user the spatial location of a sensor for which values are being visually indicated on temporal plot 1002 relative to a spatial position along the spatial axis of profile plot 1004. As described above in relation to displayed sensor indicator 1032, each displayed sensor indicator 1018 may be displayed as a tone corresponding to a tone used to visually indicate one of line traces 1009 to indicate to a user the line trace 1009 to which each displayed sensor indicator 1018 corresponds.

On a profile plot, for example, profile plot 1004, on which visually indicated values are being displayed using a line trace technique, each value detected during the temporal interval being displayed on the profile plot 1004 may be displayed as an offset along a value axis 1012 from a baseline 1010. It should be appreciated that value axis 1012 may not actually be visually indicated as profile plot 1004, but is used herein for illustrative purposes. As will be described in more detail below, values may be interpolated for locations between locations of sensors, and these values may be displayed as an offset from baseline 1010 along value axis 1012. Further, each value, whether detected or interpolated, displayed on line trace 1014 may be displayed at such a proximity to a nearest other visual indication that line trace 1014 is perceived by a user as a continuous line.

In an aspect of visually indicating values detected along a spatial dimension on a temporal plot using a line tracing technique and on a profile plot, a user may be enabled to select the sensors for which values will be visually indicated in temporal plot 1002, for example, by selecting one of the displayed sensor indicators 1018 and dragging it to a new spatial position along the spatial axis of profile plot 1004. Alternatively, the user may be enabled to select the sensors by other means, for example, a keyboard. Accordingly, if a user clicks on and drags a displayed channel indicator 1018 to a new spatial position along the spatial axis of profile plot 1004, the corresponding line trace 1009 will change to visually indicate the values detected by the sensor at the location corresponding to the spatial position to which the user drags the displayed sensor indicator. Consequently, all of the information of the sensor display panel (e.g., 1031 or 1048) may be updated accordingly.

Value control 1032 may provide a user the ability to selectably control the value (e.g., numerical value) visually indicated by landmark identifiers of landmark location identifiers. For example, the value control 1032 may enable a user to select that this value be the actual determined location of the anatomical landmark or the location of a sensor nearest to the determined location of the anatomical landmark.

In an aspect of the invention, landmark identification component 622 of visualization component 106 may be configured to generate one or more landmark location identifiers. For example, the landmark identification component 622 may receive input from landmark location determination component 632, described below in more detail, and user input, for example, user input 604. Based on these received inputs, the landmark identification component may generate information for displaying a landmark location identifier (including a landmark identifier) and output such information to one or more other components of visualization component 106, for example, profile plot component 610 and/or frame display controller 612. Further, the landmark identification component 622 may be configured to output information to the temporal plot component 608, for example, so that the temporal plot may visually indicate a spatial location identifier for an anatomical landmark, for example, as described below in more detail in relation to FIG. 15.

Returning to FIG. 11, baseline value indicator 1034 indicates the value represented by baseline 1010. High threshold indicator 1036 indicates a threshold value that will be indicated by profile plot 1004. Accordingly, if a value detected during a temporal interval exceeds the high threshold, such value will not be displayed on profile plot 1004. For example, line trace 1014 may be clipped at the one or more spatial locations corresponding to values that exceed the high threshold.

It should be appreciated that the several aspects of the invention described above in relation to visually indicating detected values on temporal plot 1002 and profile plot 1004 concurrently may apply to temporal plots and profile plots that visually indicate values using any of a variety of techniques, for example, those techniques described above. Further, aspects described with respect to plots 1002 and 1004 being displayed concurrently, may apply to a contour plot or a profile plot being visually indicated alone, without the other type of plot. Further, the aspects described above with respect to plots 1002 and 1004 may be combined with various other aspects described herein.

Figure 12:
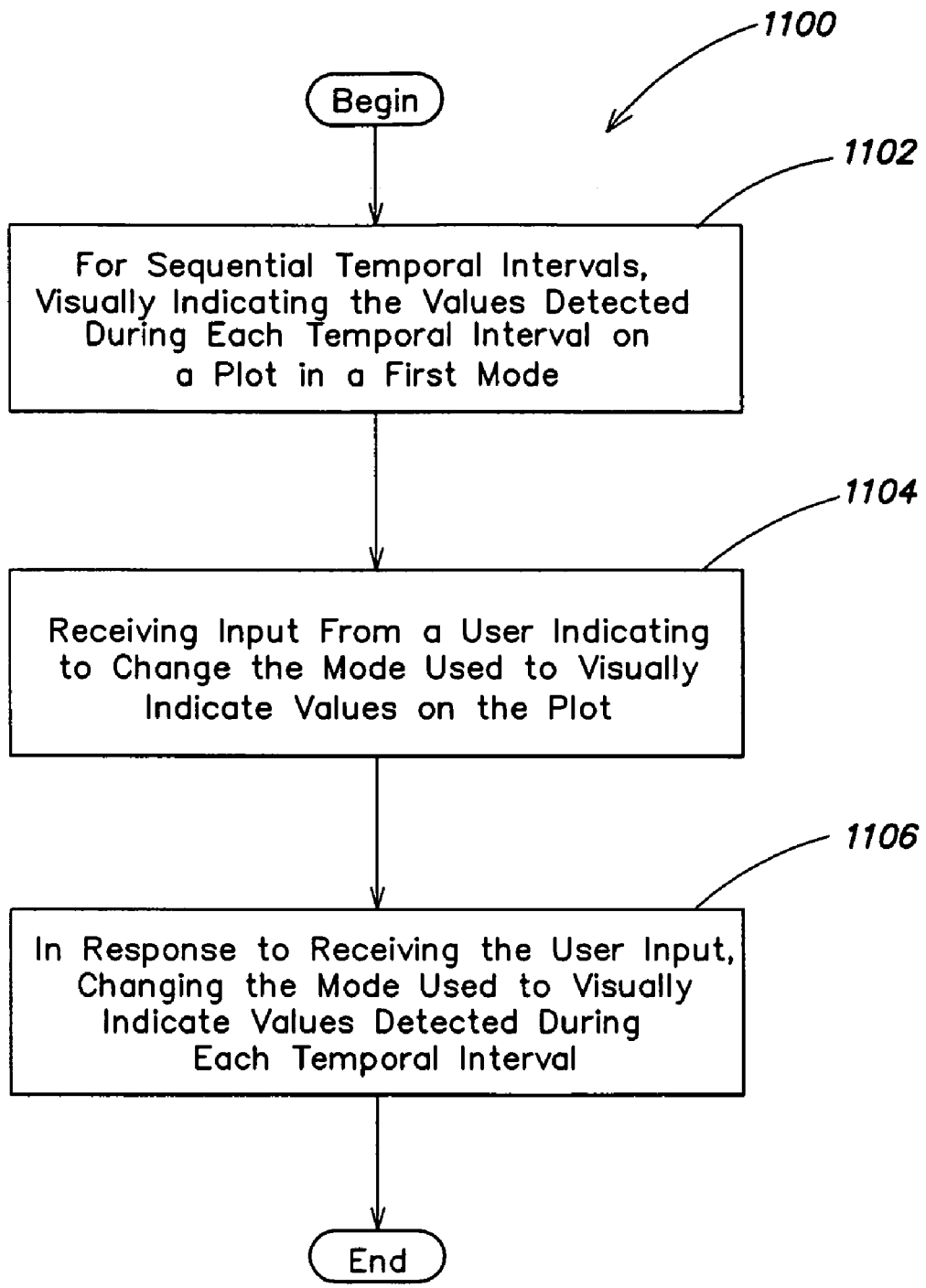
FIG. 12 is a flow chart illustrating an example of a method of toggling between visually indicating values detected over a period time on a plot in a first mode and visually indicating the values on the plot in a second mode.

FIG. 12 is a flow chart illustrating an example of a method 1100 of toggling between visually indicating values detected over a period of tine on a plot in a first mode (e.g., contour mode or line trace mode) and visually indicating the values on the plot in a second mode (e.g., line trace mode or contour mode).

In Act 1102, for sequential temporal intervals, the values detected during each temporal interval may be visually indicated on a plot in a first mode, for example, a contour mode or a line trace mode. In Act 1104, input may be received from a user indicating to change the mode used to visually indicate values on the plot. For example, display 1000 may include a mode button 1034 and/or a mode button 1023 which allow a user to indicate to change the mode being used to visually indicate values on temporal plot 1002 and profile plot 1004, respectively.

In Act 1106, in response to receiving the user input, the mode used to visually indicate values detected during each temporal interval may be changed, for example, from contour mode to line trace mode or vice versa.

Figure 13:
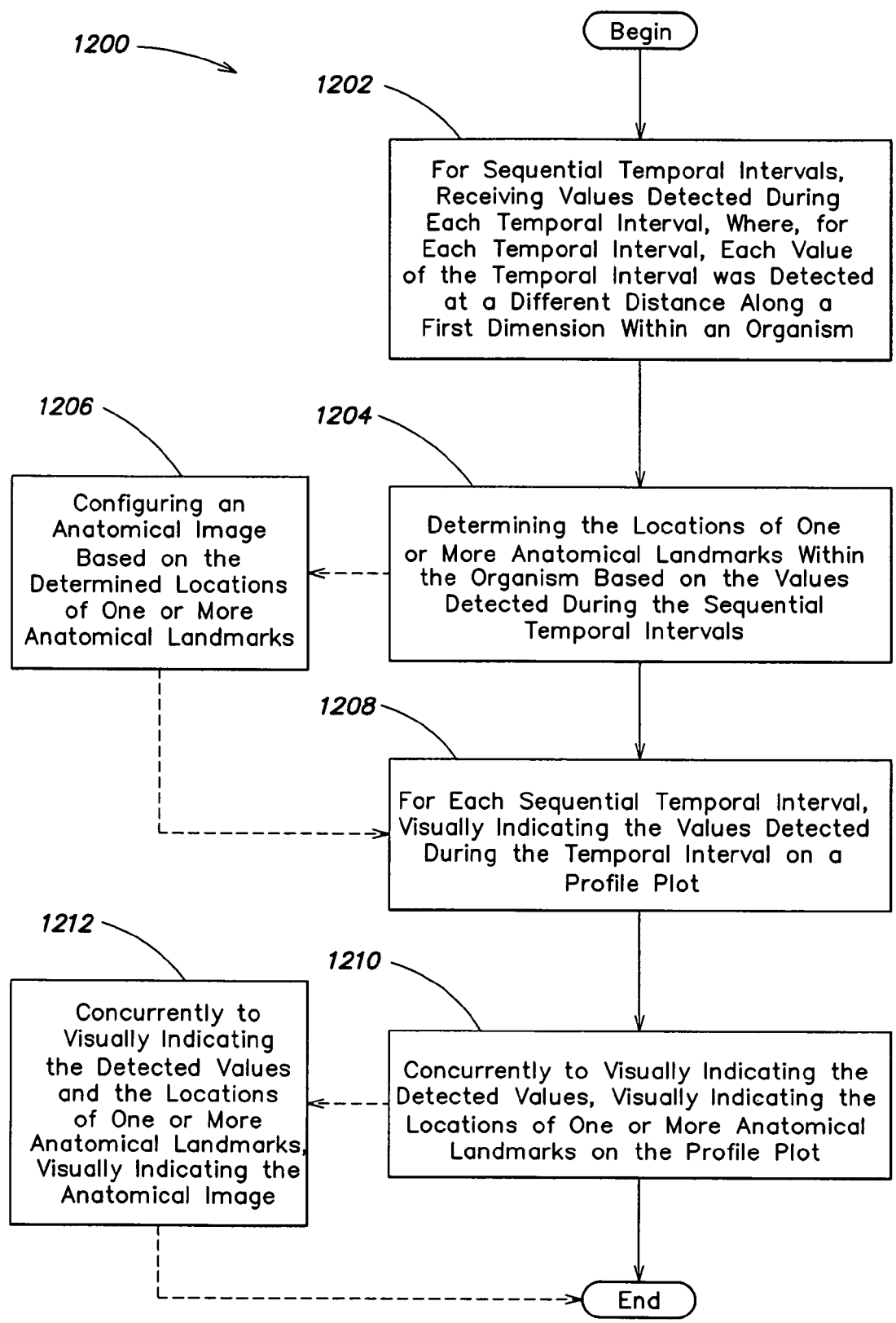
FIG. 13 is a flow chart illustrating an example of a method of concurrently visually indicating detected values, locations of anatomical landmarks and an anatomical image on a plot.

FIG. 13 is a flow chart illustrating an example of a method 1200 of concurrently visually indicating detected values, anatomical landmarks and an anatomical image on a plot, for example, a profile plot. The anatomical image may include at least portions of one or more organs, for example, a pharynx, UES, esophagus, LES, stomach, duodenum, colon, small bowel, sphincter of Oddi, anus or rectum.

In Act 1202, for sequential temporal intervals, values detected during each temporal interval are received, where, for each temporal interval, each value of the temporal interval was detected at a different distance along a dimension of an organism.

In Act 1204, the locations of one or more anatomical landmarks within the organism are determined based on the value detected during the sequential temporal intervals. As used herein, an anatomical landmark is a physically significant location within an anatomy. For example, in the upper GI tract, anatomical landmarks may include the LES, the upper and lower margins of the LES, the UES and the PIP. Determining the locations of one or more anatomical landmarks is described below in more detail in relation to FIGS. 16-21.

Optionally, in Act 1206, an anatomical image may be configured based on the determined locations of one or more anatomical landmarks. For example, the anatomical image may have a basic default structure that can be altered based on determined locations of one or more anatomical landmarks. For example, if the anatomical image is an image of an upper GI tract, the anatomical image may include a pharynx, UES, esophagus, LES and stomach. The width of the pharynx, UES, LES and stomach in the anatomical image may remain fixed. Further, the length of the stomach and the UES may remain fixed in the anatomical image. The position of the pharynx, the UES and the stomach and the length of the esophagus and the LES may be configured, however, based on the determined locations of one or more anatomical landmarks, for example, the UES, the LES, the upper margin of the LES and the lower margin of the LES.

In Act 1208, for each sequential temporal interval, the values detected during the temporal interval may be visually indicated on a profile plot, for example, using a contour technique or line tracing technique.

In Act 1210, concurrently to visually indicating the detected values on the profile plot, the locations of one or more anatomical landmarks may be visually indicated on the profile plot.

Optionally, in Act 1212, concurrently to visually indicating the detected values and the locations of one or more anatomical landmarks, the anatomical image may be visually indicated on the profile plot. For example, the detected values and the locations of the anatomical landmarks may be superimposed on the anatomical image. Alternatively, or additionally, the anatomical image could be visually indicated elsewhere, for example, on a temporal plot or proximate to the profile plot.

In an aspect of method 1200, the anatomical image may be displayed concurrently with the detected values on a profile plot, but no locations of anatomical landmarks may be visually indicated. Further, alternatively, the anatomical image may be displayed concurrently with one or more anatomical landmarks on a profile plot, but no detected values may be visually indicated, for example, during a temporal interval for which no values have been detected.

Figure 14:
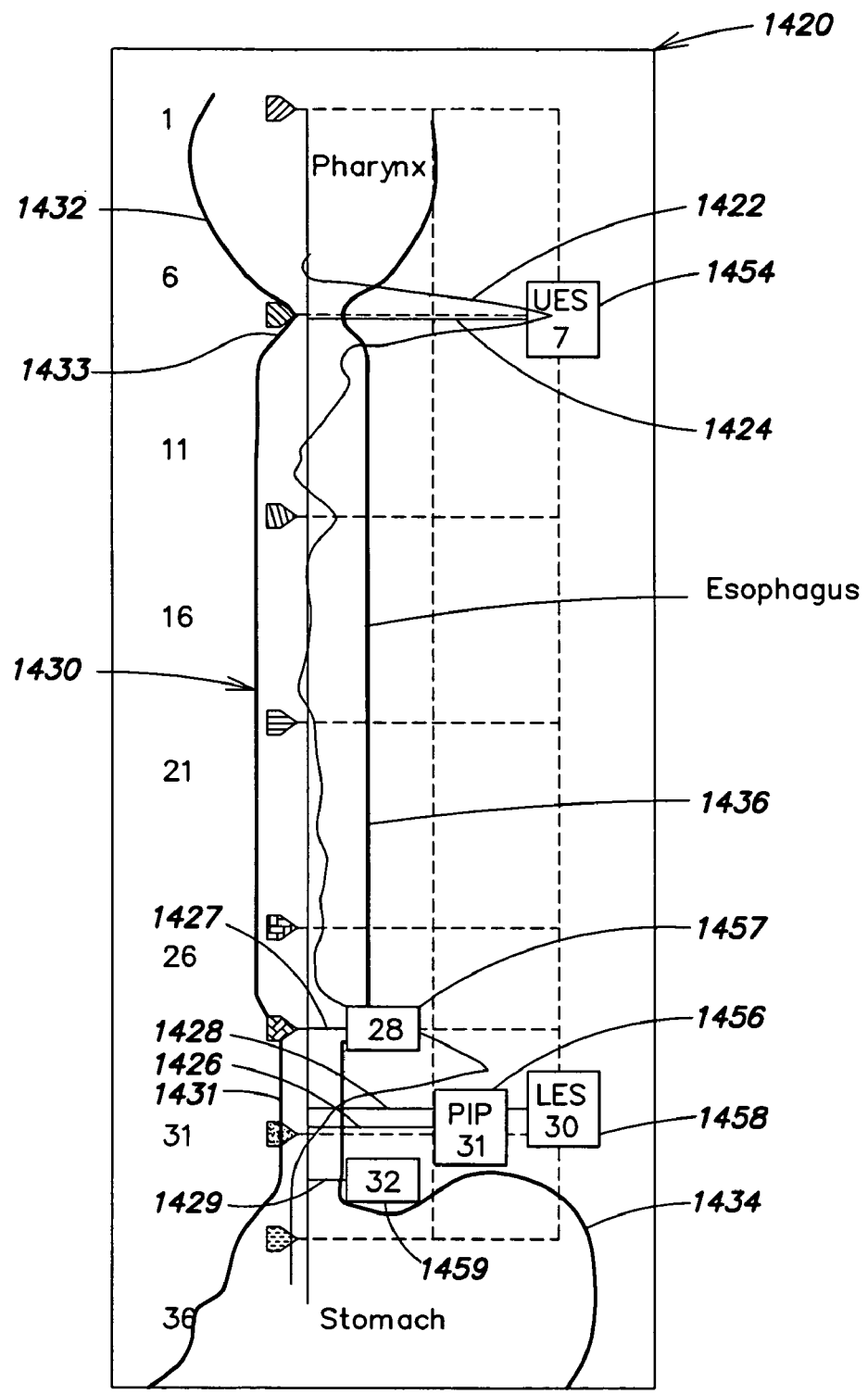
FIG. 14 is an example of a profile plot on which detected values, landmark location identifiers and an anatomical image are concurrently visually indicated.

FIG. 14 is an example of a profile plot 1420 on which a line trace 1422 of detected values, landmark location identifiers 1424, 1426, 1427, 1428 and 1429 including corresponding landmark identifiers 1454, 1456, 1457, 1458 and 1459, and an anatomical image 1430 are concurrently visually indicated. Profile plot 1420 may be generated by a plurality of logical components of visual component 106, as will be described in more detail below.

Although the detected values 1422 are visually indicated using a line trace technique, other techniques may be used, such as a contour technique or histogram technique. The values 1422 may be values detected during a temporal interval, where a plurality of sensors located at different distances along the GI tract of a human.

The landmark location identifiers may include a UES location identifier 1424, a PIP location identifier 1426, an LES location identifier 1428, an LES upper margin identifier 1427 and an LES lower margin identifier 1429.

The plot 1420 also may include anatomical image 1430 which illustrates a pharynx 1432, a stomach 1434, the esophagus 1436, the UES 1433 and the LES 1431.

In an aspect of visually indicating landmark location identifiers to a user, the profile pot 1420 may be part of a GUI that enables a user to manual select and relocate the location of one or more of the landmark location identifiers, for example, by clicking and dragging one or more of the landmark location identifiers using a mouse. This may be helpful for a user that has enough knowledge about the anatomy (e.g., a physician) to make judgments about the proper location of a landmark. Such user can move the landmark location identifier to a spatial position at which the user believes the anatomical landmark represented by the identifier is located based on the user's interpretation of the visual display of the detected values on the profile plot and/or on a temporal plot.

Accordingly, in an aspect of visually indicating landmark location identifiers, the locations of the landmark location identifiers may be determined automatically, as described below in relation to FIGS. 16-21, manually, or a combination thereof. A GUI may provide a user the ability to select between automatic or manual determination of the location of one or more anatomical landmarks and to toggle between the two, post hoc or in real time.

A profile plot that concurrently visually indicates detected values, landmark location identifiers and/or an anatomical image may be visually indicated concurrently with a temporal plot visually indicating at least a subset of the detected values, in real time or post hoc.

Figure 15:
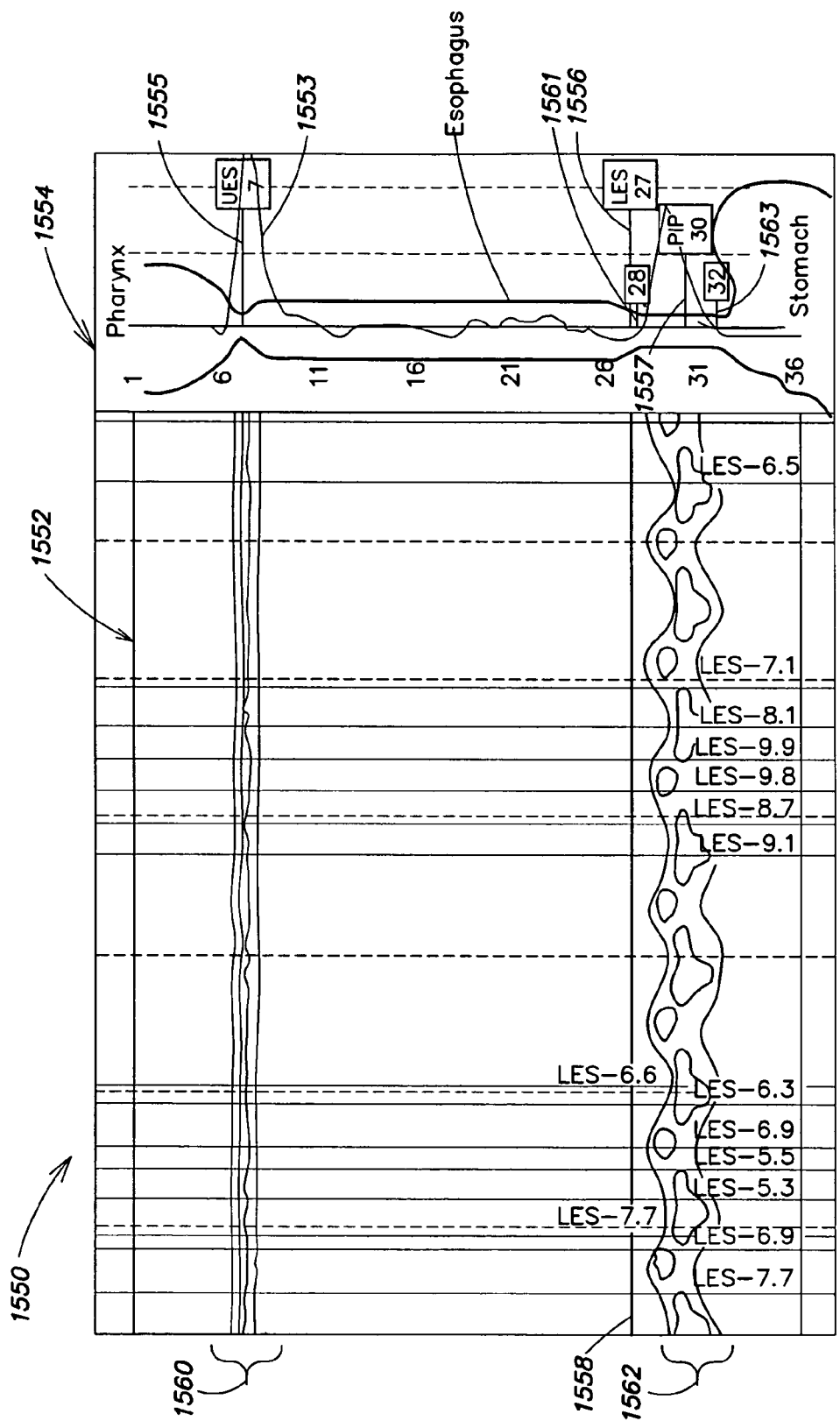
FIG. 15 is an example of a display including a profile plot on which detected values, landmark location identifiers and an anatomical image are visually indicated and a moving contour plot on which a spatial position of one of the landmark location identifiers is visually indicated.

FIG. 15 is an example of a display 1550 including a profile plot 1554 that includes visual indications of detected values, landmark location identifiers and an anatomical image. Display 1550 also includes a moving contour plot 1552 that visually indicates the detected values. Display 1550 may be generated by a plurality of the logical components included in visualization component 106, as will be described in more detail below.

The values visually indicated in moving contour plot 1552 and profile plot 1554 may be values detected over a period of time from a plurality of sensors located along the upper GI tract of a human while the human is at rest (e.g., just breathing regularly, not swallowing, coughing, gagging). As can be seen from the peaks of the line trace 1555 in profile plot 1554 and the brighter tones visually indicated along spatial lengths 1560 and 1562 of the moving contour plot, higher pressure is detected around the UES and the LES.

Accordingly, it may be desirable to determine the location of anatomical landmarks along the upper GI tract by detecting the values over a period of time while the subject (e.g., a human) is at rest. Making the determination at rest may be more desirable because the pressure detected at the UES, LES and along the esophagus do not fluctuate significantly as they do when the subject is swallowing, for example, as illustrated in FIG. 8.

As can be seen in FIG. 8, when a subject is swallowing, a pressure wave descends down the esophagus over time. As will be described in more detail below in relations to FIGS. 16-21, determining the location of anatomical landmarks may depend on determining local maximums of pressure detected along the upper GI tract. Accordingly, these determinations may be skewed if the positions of local maximums change over time as illustrated in FIG. 8.

Thus, after the location of one or more anatomical landmarks has been determined while the subject is at rest, it may be desirable to leave the visual indication of these locations unchanged by disabling the ability to determine the location of one or more anatomical landmarks. Accordingly, when values are then detected for a specific event, such as swallowing or coughing, the determined locations of the one or more anatomical landmarks will not be skewed.

As discussed above, in an aspect of the invention, display 1550 may be part of a GUI that enables a user to click and drag on any of the landmark location identifiers, for example, UES identifier 1555, LES identifier 1556, LES upper margin identifier 1561, LES lower margin identifier 1563 and PIP identifier 1557. Further, the GUI may be configured such that when a user clicks on (and possibly drags) a landmark location identifier, a spatial location identifier of the anatomical landmark may be displayed on the moving contour plot 1552. Alternatively, such spatial location identifier continually may be displayed on the moving contour plot 1552. For example, LES spatial location identifier 1558 may be displayed continually on moving contour plot 1552 or may be displayed in response to a user clicking on and/or dragging LES identifier 1556.

Figure 16:
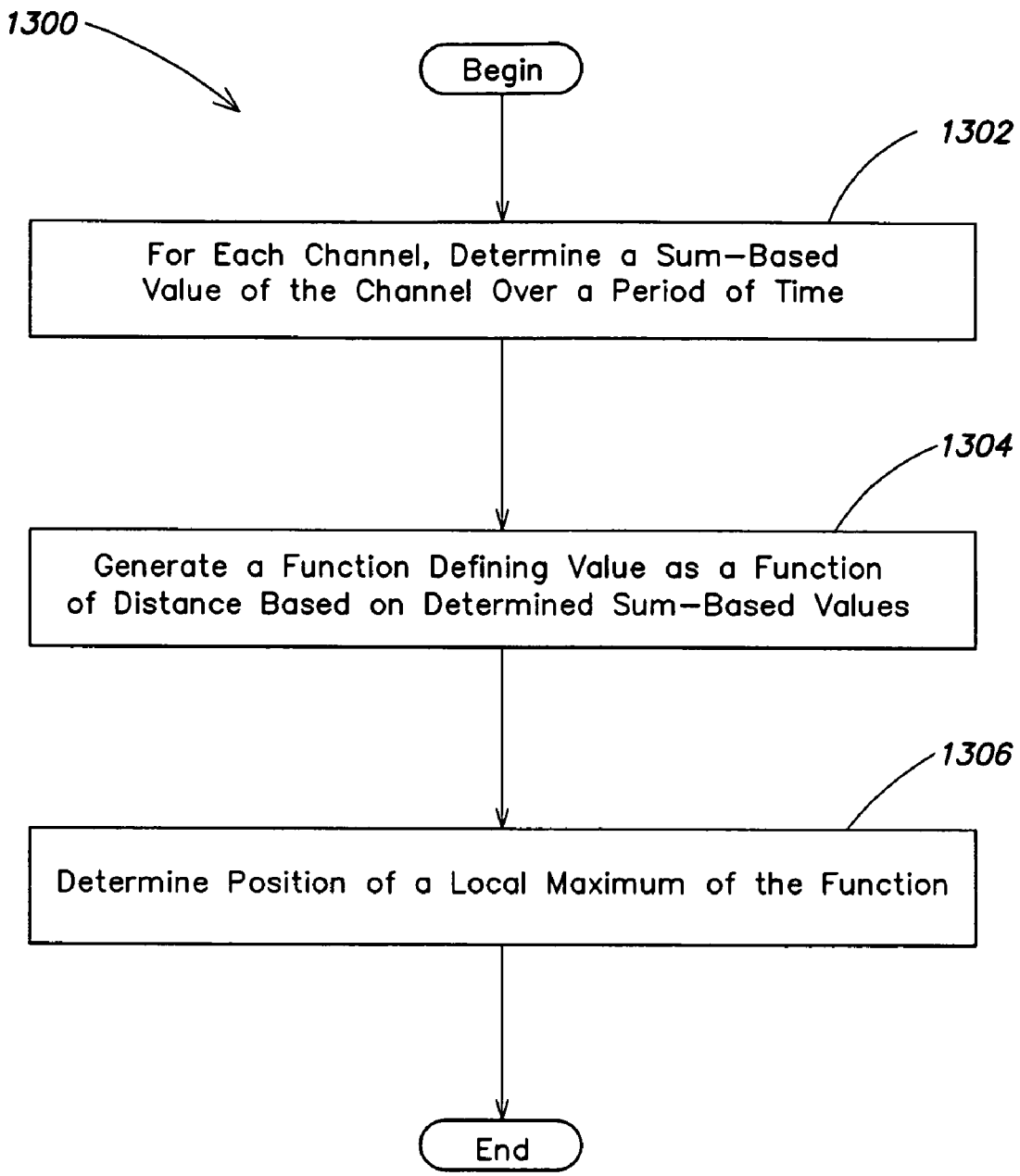
FIG. 16 is a flowchart illustrating an example of a method of determining a location of an anatomical landmark of an organism.

FIG. 16 is a flow chart illustrating an example of a method 1300 of determining the location of an anatomical landmark along a dimension of an organism. For the description of FIGS. 16-22, each "channel" represents a series of values detected at a respective sensor over time.

In Act 1302, for each channel, a sum-based value of the channel for a period of time may be determined. The sum-based value of a channel may be the sum of all values of the channel detected over a period of time, the average value detected on the channel over a period of time (i.e., the sum divided by the number of temporal intervals), or another value derived from the sum, for example, a normalized value. In an example where the sum-based value is an average, the average may be determined based on the following equation:

$$A_{Ci} = \sum_{j=1}^{N} C_{i,j} / N \qquad \text{Equation 1}$$

where $A_{Ci}$ is the average determined for the ith channel, N is the number of values detected for the given channel, and $C_{ij}$ is the jth value of the ith channel.

In a next Act 1304, a function defining values as a function of distance may be generated based on the sum-based values. The function could be generated using any of a variety of techniques, for example, using known curve fitting techniques such as cubic spline interpolation.

As an alternative to performing Acts 1302 and 1304, where sum-based values for each channel are determined and then a function generated based on these sum-based values, these steps may be essentially reversed as follows. For each channel, a function may be generated defining the values of the channel as a function of time, and then an average value may be determined for each channel by integrating the defined function over a period of time. The location of the anatomical landmark then may be determined based on the averages determined for each channel.

In Act 1306, the position of a local maximum of the function (e.g., in a region local to the esophagus) may be determined. For example, the position of the local maximum may be determined by performing a point-by-point comparison of values generated from the function at different spatial positions or by using well-known techniques based on determining the derivative of the function. This determined position may serve as the location of the anatomical landmark along a dimension of an organism.

The determined function may have more than one local maximum. Thus, Act 1306 may include determining a position of a first local maximum within a predefined spatial range. This predefined spatial range may be determined based on knowledge of the portion of the organism from which the values are being detected. For example, the values may be detected from the upper GI tract of a human from a detection system including a catheter and a plurality of sensors embedded therein or attached thereto. Thus, method 1300 may be applied to determine the position of the UES or LES. For the UES, the predefined range may be from five to ten cm from a reference point, and for the LES, the predefined range may be from twenty-five to thirty-five cm from the reference point. The catheter may be inserted at a proximal depth within the upper GI tract based on knowledge of the general position of the UES and LES within the upper GI tract.

As an alternative to Acts 1304 and 1306, the location of the anatomical landmark may be determined by selecting a channel within a spatial range that has the highest determined sum-based value. The spatial range may be predetermined based on knowledge of the portion of the organism from which the values are being detected.

Figure 17:
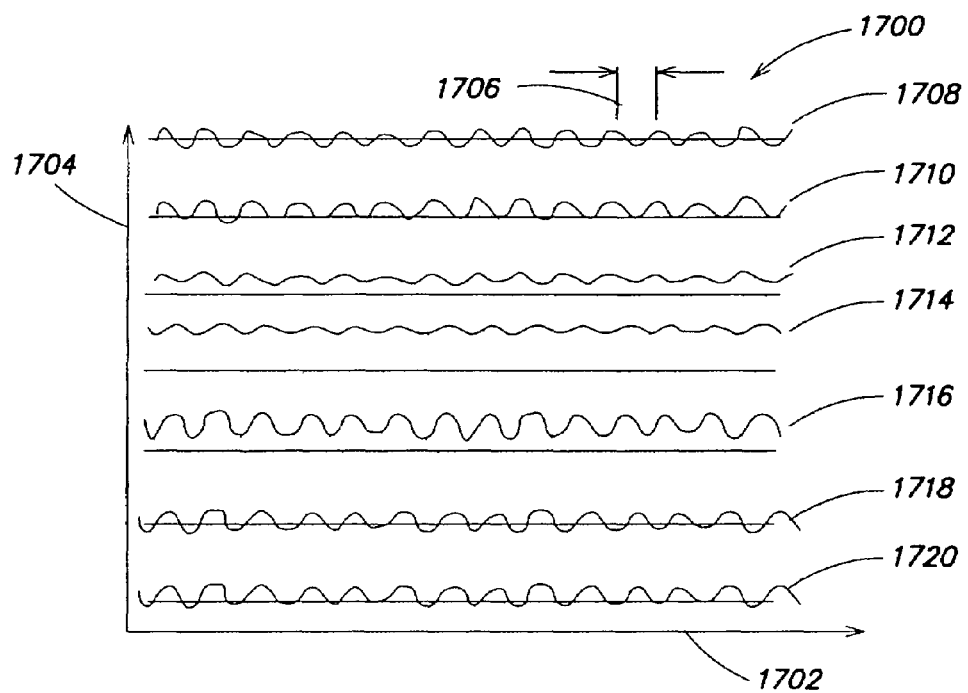
FIG. 17 is an example of a display including visual indications of values detected at a plurality of locations over a period of time.

FIG. 17 is a display 1700 illustrating an example of line trace plots of values detected from a plurality of channels (corresponding to sensors) 1708, 1710, 1712, 1714, 1716, 1718 and 1720 on a temporal plot having a spatial axis 1704 and a temporal axis 1702. The visually indicated values may have been detected along a dimension of an upper GI tract of a subject while the subject was at rest. As can be seen, for each channel, the detected values may be cyclical in nature, having a cycle 1706 corresponding to a respiratory cycle of the subject.

Figure 18:
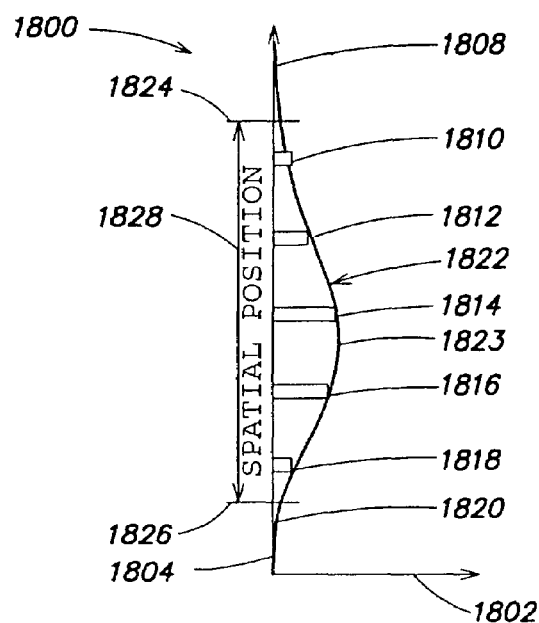
FIG. 18 is an example of a plot of sum-based values determined for values detected at a plurality of locations over a period of time.

FIG. 18 is an example of a sum-based plot 1800 having a spatial axis 1804 and value axis 1802, including visual indications of the determined sum-based values 1808, 1810, 1812, 1814, 1816, 1818 and 1820 determined for channels 1708, 17010, 1712, 1714, 1716, 1718, 1720, respectively. Plot 1800 includes a line trace 1822 of function values produced by applying a function generated based on the sum-based values 1808-1820. The position of the first local maximum of the determined function may be indicated at location 1823. Alternatively, the position of the anatomical landmark may be determined based on the sum-based values themselves, in which case the position of the anatomical landmark may be at the location corresponding to sum-based value 1814.

Figure 19:
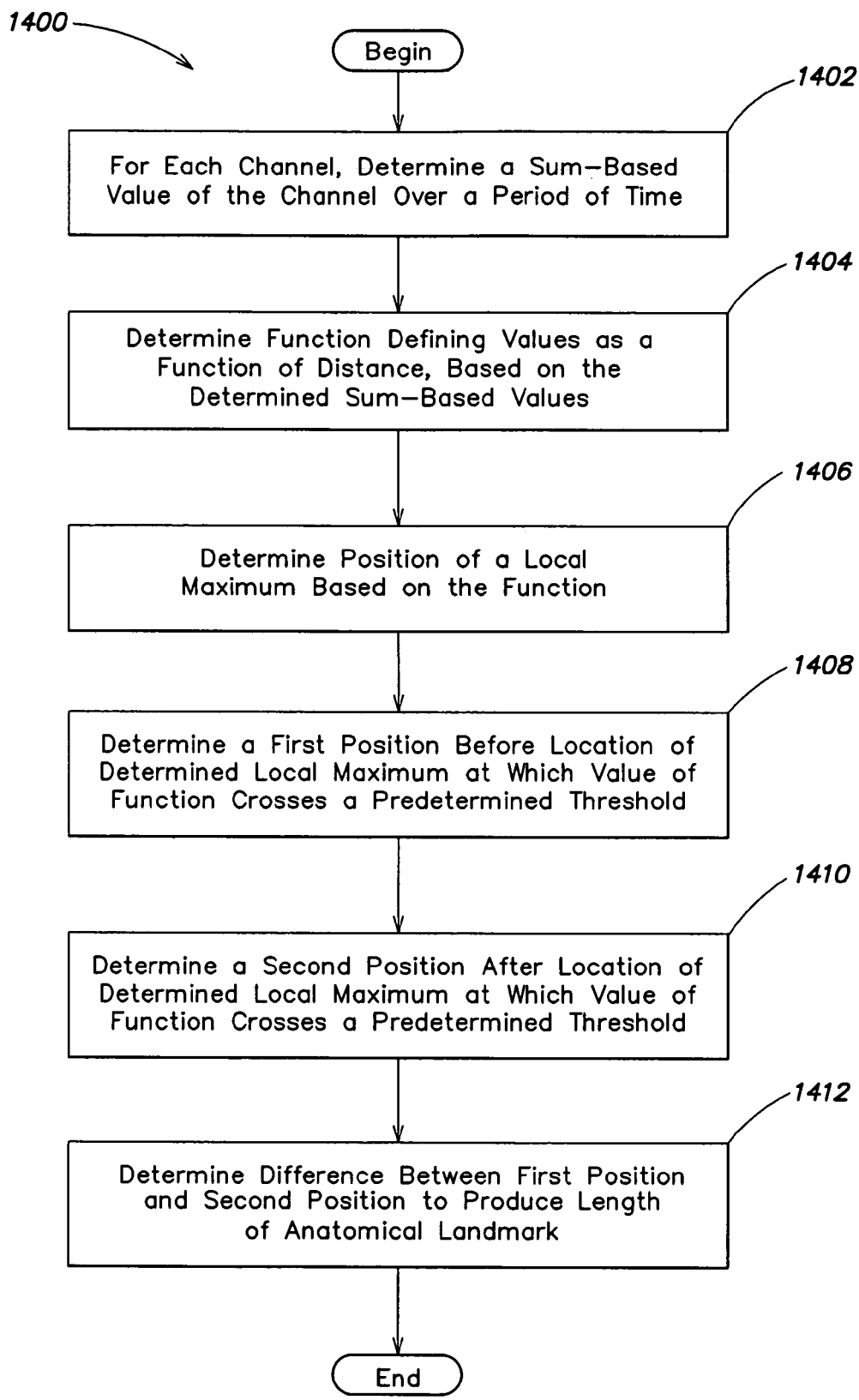
FIG. 19 is a flow chart illustrating an example of determining a location and length of an anatomical landmark within an organism.

FIG. 19 is a flow chart illustrating an example of a method 1400 for determining the spatial position and length of an anatomical landmark of an organism based on values detected over a period of time from an organism. Acts 1402-1406 may be performed as described above for Acts 1302-1306, respectively. In an aspect of method 1400, where the position and length of an LES of a human is being determined, Act 1406 may include determining a position within a predefined spatial range within which it is known the LES resides. Alternatively, the position of the local maximum in Act 1406 may be determined by selecting from a plurality of local maximums determined in Act 1404, a local maximum of the function determined at a furthest distance from a reference point (i.e., the spatially last local maximum), or a local maximum occurring within a certain predefined distance from where a local maximum of the UES is determined.

In Act 1408, a first position, located before (i.e., located closer to a reference point) the location of the determined local maximum, at which a value of the function crosses a predetermined threshold may be determined. For example, a location within a predefined vicinity of the local maximum, at which a function crosses a predefined threshold and has a positive slope, may be determined or, a last (i.e., furthest from a reference point) crossing of the threshold before the determined local maximum may be determined. For example, referring to FIG. 18, where the determined local maximum is located at position 1822, the first position at which function 1822 crosses a predefined threshold may be determined as spatial position 1824.

In Act 1410, a second position, located after (i.e., further from a reference point) than the location of the determined local maximum, at which a value of the function crosses a predetermined threshold may be determined. For example, Act 1410 may include determining a position within the vicinity of the determined local maximum at which the value of the function crosses the predetermined threshold and has a negative slope, or may include determining a last position occurring after the second local maximum at which the value of the function crosses the predetermined threshold.

For example, referring to FIG. 18, it may be determined that the value of the function defined by line trace 1822 crosses the predetermined threshold after location 1822 at spatial position 1826.

In Act 1412, a difference between the first position and the second position may be determined to produce a length of an anatomical landmark, for example, an LES. For example, referring to FIG. 18, the difference between first position 1824 and second position 1826 may be determined to be length 1828, which serves as the length of the anatomical landmark.

Figure 20A:
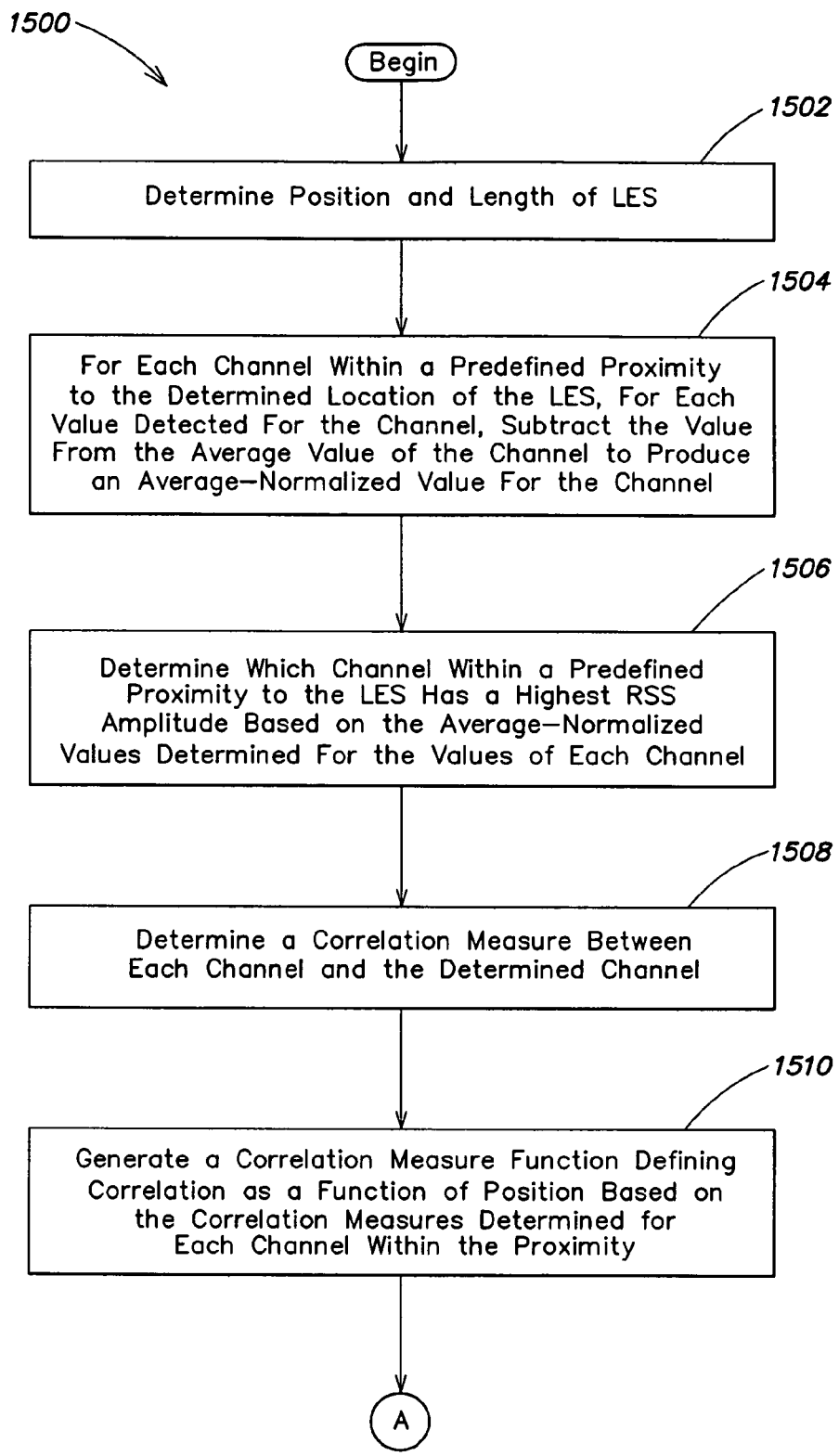
FIGS. 20A-20B comprise a flow chart illustrating an example of a method of determining a position of a pressure inversion point within an upper GI tract.
Figure 20B:
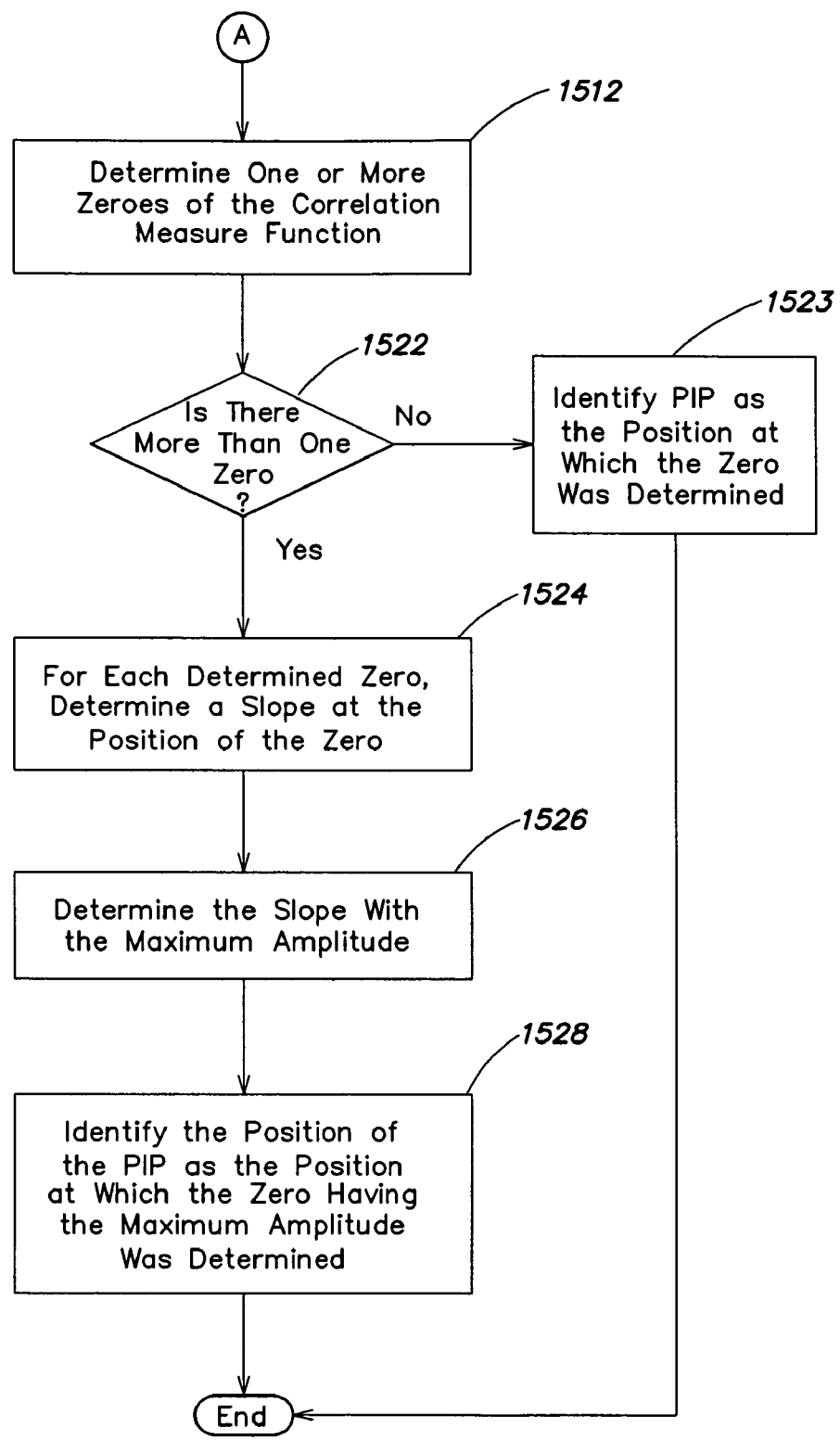

FIGS. 20A and 20B comprise a flow chart illustrating an example of a method 1500 for determining a position of a PIP within the upper GI tract of a human based on values detected along the upper GI tract over a period of time.

In Act 1502, a position and length of the LES are determined, for example, as described in method 1400.

In Act 1504, for each channel within a predefined proximity to the determined location of the LES, for each value detected for the channel, the value may be subtracted from the average value of the channel to produce an average-normalized value for the value. For example, if the average of each channel was determined by application of Equation 1 above, the normalized average of each value of a channel may be determined by application of the following equation:

$$AN_{ij} = C_{ij} - A_{Ci} \quad \text{Equation 2}$$

where $AN_{ij}$ is an average-normalized value determined for the jth value of the ith channel, $C_{ij}$ is the jth value of the ith channel and $A_{Ci}$ is the average value of the ith channel.

In a next Act 1506, it may be determined which channel within a predefined proximity to the LES has a highest root-sum-squared (RSS) amplitude based on the average-normalized values determined for the values of each channel. The RSS of each channel within the proximity may be determined by application the following equation:

$$RSS_i = sqrt\left[\sum_{j=1}^{N}(AN_{i,j})^2\right] \quad \text{Equation 3}$$

where RSSi is the determined RSS of an ith channel, N is the number of values detected for the ith channel, and $AN_{i,j}$ is the average-normalized value for an jth value of the ith channel. The channel with the greatest RSS amplitude may be referred to as the mth channel.

In a next Act 1508, a correlation measure may be determined between each channel and the channel determined in Act 1506. Any of a variety of techniques may be used to determine this correlation measure, for example, application of equation 4:

$$CM_i = \sum_{j=1}^{N} AN_{ij} AN_{mj} \quad \text{Equation 4}$$

where $CM_i$ is the correlation measure of the ith channel, $AN_{ij}$ is an average-normalized value for the jth value of the ith channel and $AN_{mj}$ is an average-normalized value of the mth value of the channel determined in Act 1506.

In Act 1510, a correlation measure function may be generated defining correlation as a function of position based on the correlation measures determined for each channel in Act 1508. For example, known curve-fitting techniques may be employed to generate the function.

In Act 1512, one or more zeros of the correlation measure function may be determined using known techniques for determining zeros of a function.

Next, in Act 1522, it may be determined whether there is more than one zero.

If there is not more than one zero, then in Act 1523, the PIP is identified as the position at which the zero was determined.

If it is determined that there is more than one zero, then in Act 1524, for each determined zero, a slope at the position of the zero is determined, and in Act 1526, the slope with the maximum magnitude may be determined.

In Act 1528, the position of the PIP is identified as the position at which the zero having the slope with the maximum magnitude was determined.

Figure 21:
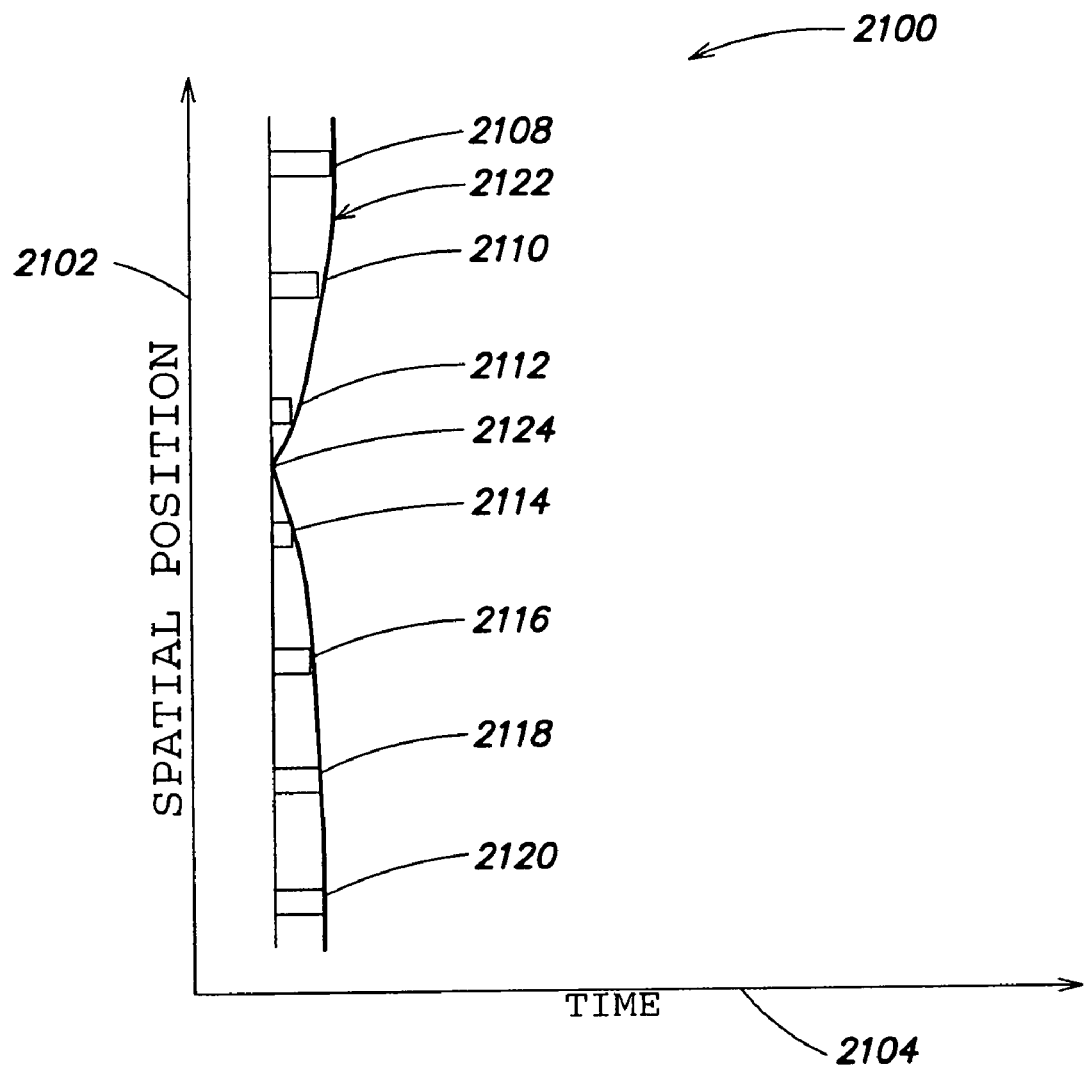
FIG. 21 is an example of a correlation measure plot determined from values detected from different locations over a period of time.

FIG. 21 includes a correlation measure plot 2100 having a spatial axis 2102 and a correlation measure axis 2104. The correlation measures illustrated in FIG. 21: 2108, 2110, 2112, 2114, 2116, 2118 and 2120, may correspond to channels 1708, 1710, 1712, 1714, 1716, 1718 and 1720 of FIG. 17. As illustrated by the line trace 2122 of the correlation measure function, the correlation measure function has a zero at location 2124.

Any of a variety of other techniques may be used to determine the location of a PIP. For example, Fast Fourier Transformations based on a first and second harmonic of the respiratory frequency of the subject being examined may be employed to determine the location of the PIP.

The location of anatomical landmarks may be determined using values detected over a fixed time frame or for a sliding time frame. For example, for a three hundred second period during which values are detected, a fixed time frame may be set at thirty seconds such that the location of one or more anatomical landmarks may be determined at the end of each thirty second interval for the previous thirty seconds of detected values. Alternatively, for a same time period, a sliding time frame may be employed such that the location of one or more anatomical landmarks is determined for overlapping thirty second interval within the three hundred seconds. In other words, the location of one or more anatomical landmarks may be determined for intervals from zero to thirty seconds, one to thirty-one seconds, two to thirty-two seconds, two hundred seventy one to three hundred seconds, etc.

The sliding time frame technique may be preferred if it is desirable to have the determined locations of the anatomical landmarks updated continually. This continual updating may be beneficial if the sensors that are detecting the values are moving over time.

As described above, the plurality of sensors that detect values over time each may be separated from a nearest sensor by a predefined distance, for example one cm. Thus, if the location from which the values are being detected and the location of the one or more sensors remains fixed, then the spacing between the sensors, for example, one cm, defines the spatial resolution of the determined location of one or more anatomical landmarks. To effectively increase the spatial resolution of the determined locations, values may be detected over a first period of time, and then the sensors may be moved a predefined distance that is less than the spacing between the sensors, for example, ½ cm for sensors that are spaced one cm apart. After the sensors have been moved, values may be detected by the sensors over a second period of time. Methods 1300, 1400 and/or 1500 then may be performed on the combined set of values detected during both periods. By applying this technique, the spatial resolution of the determined locations of one or more anatomical landmarks may be increased, resulting in a more accurate determination of the location of the one or more anatomical landmarks.

In an aspect of the invention, the landmark location determination component 632 of visualization component 106 may be configured to determine the location of one or more anatomical landmarks, for example, as described above in relation to FIGS. 16-21. The landmark location determination component 632 may be configured with an input to receive detected values, for example, detected values 602, and with an input to receive user input, for example, user input 604. Based on these inputs, the landmark location determination component may determine the locations of one or more anatomical landmarks and output these determined locations to one or more other logical components of visualization component 106, for example, landmark identification component 622, temporal plot component 608, profile plot component 610, and/or frame display controller 612.

The landmark location determination component may include summing logic to sum the values of a channel detected over a period of time, averaging logic to determine an average value of values detected by a channel over a time, a function generator to generate a function defining values as a function of distance based on determined sum-based values, local maximum logic to determine local maximums based on sum-based values, threshold crossing logic to determine when values generated by a function cross a predetermined threshold, average-normalized value logic to generate average-normalized values as described above, RSS logic to determine a root-sum-squared amplitude of a channel and compare it to the root-sum-squared amplitudes of other channels to determine which channel has a highest root-sum-squared amplitude, correlation measure logic to determine a correlation between channels and to determine a correlation measure function as described above, zero determining logic to determine the zero of a correlation measure function and any of a variety of other logical components.

As described above in relation to FIG. 11, when detected values are visually indicated on a temporal plot using a line tracing technique, it may be desirable to display values detected from only a subset of the sensors. In an embodiment of visually indicating values detected from a subset of sensors on a temporal plot, the sensors for which to display detected values may be determined based on one or more distances defined relative to one or more anatomical landmarks.

Figure 22:
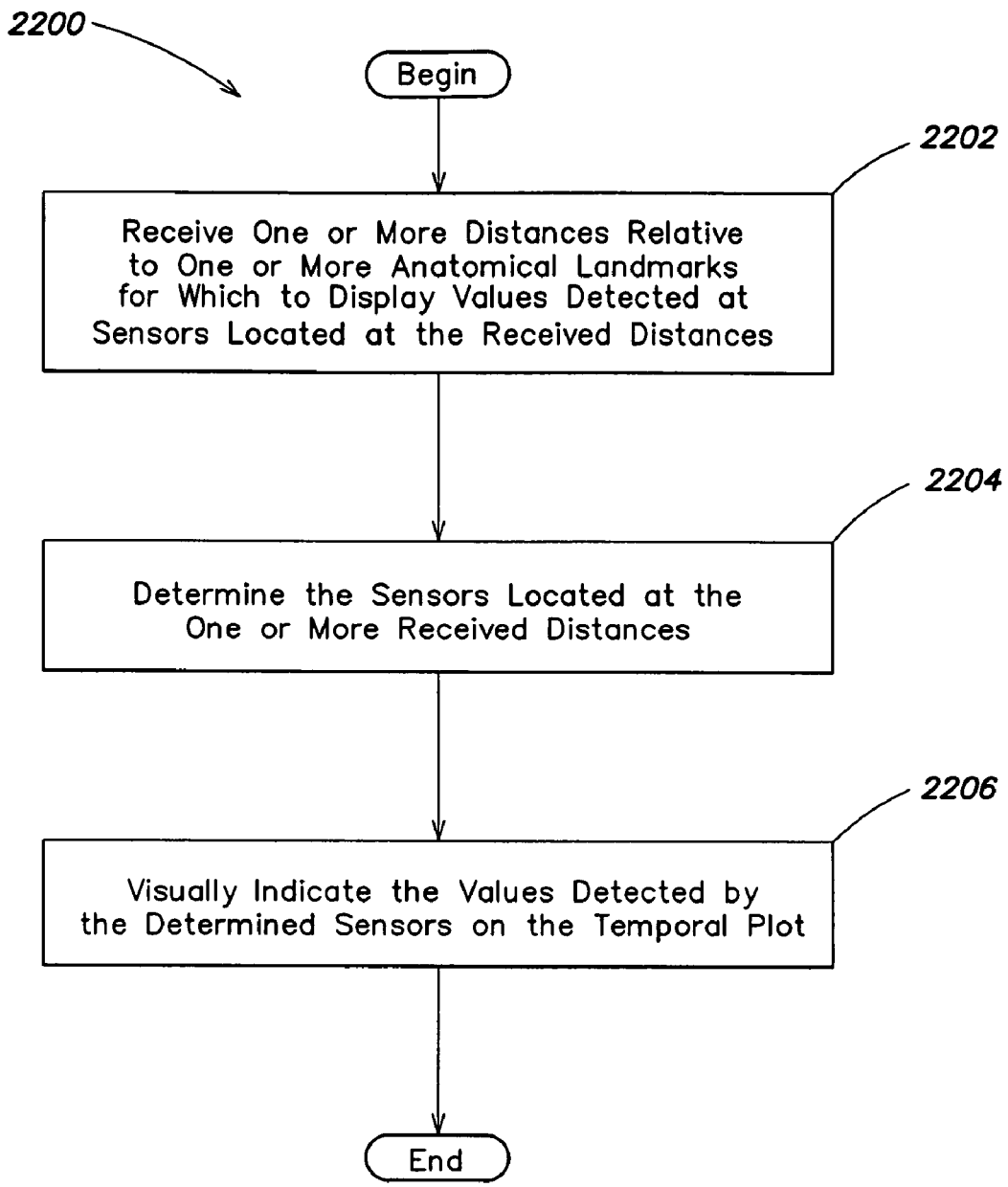
FIG. 22 is an example of a method of visually indicating values detected by a subset of sensors on a temporal plot using a line tracing technique based on one or more distances defined relative to the locations of one or more anatomical landmarks.

FIG. 22 is an example of a method 2200 of visually indicating values detected by a subset of sensors on a temporal plot (e.g., using a line tracing technique) based on one or more distances defined relative to one or more anatomical landmarks. In Act 2202, one or more distances relative to one or more anatomical landmarks are received for which to display values detected at sensors located at the received distances.

In Act 2204, the sensors located at the one or more received distances are determined, and in Act 2206, the values detected by the determined sensors are visually indicated on the temporal plot, for example, using the line tracing technique. Such one or more distances may be received from a user as part of the user input, for example, input entered by a user on a GUI.

Figure 23:
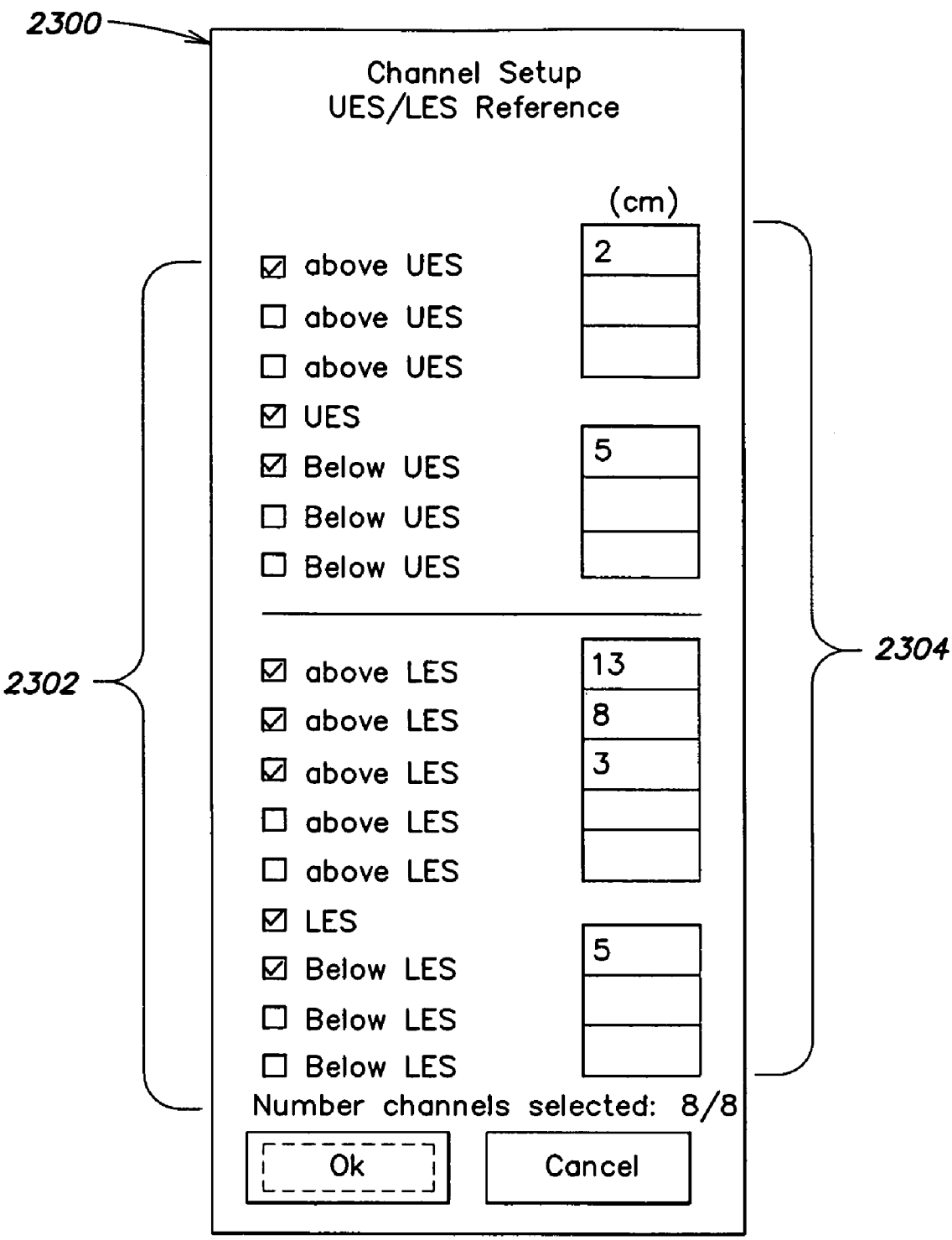
FIG. 23 is an example of a control panel of a GUI through which a user can define one or more distances relative to a UES and/or an LES.

FIG. 23 is an example of a control panel 2300 of a GUI through which a user can define one or more distances relative to a UES and/or an LES. The control panel 2300 may include distance entry boxes 2304 and relative anatomical landmark check boxes 2302. Thus, using the control panel 2300, a user may define one or more distances relative to UES or an LES by checking an anatomical landmark reference in one of check boxes 2302 and entering a distance in one of boxes 2304. In the example of FIG. 23, the user has entered instructions to display values detected at sensors located: two cm above UES, at UES, five cm below LES, thirteen cm above LES, eight cm above LES, three cm above LES, at LES and five cm below LES for a total of eight sensors.

Figure 24:
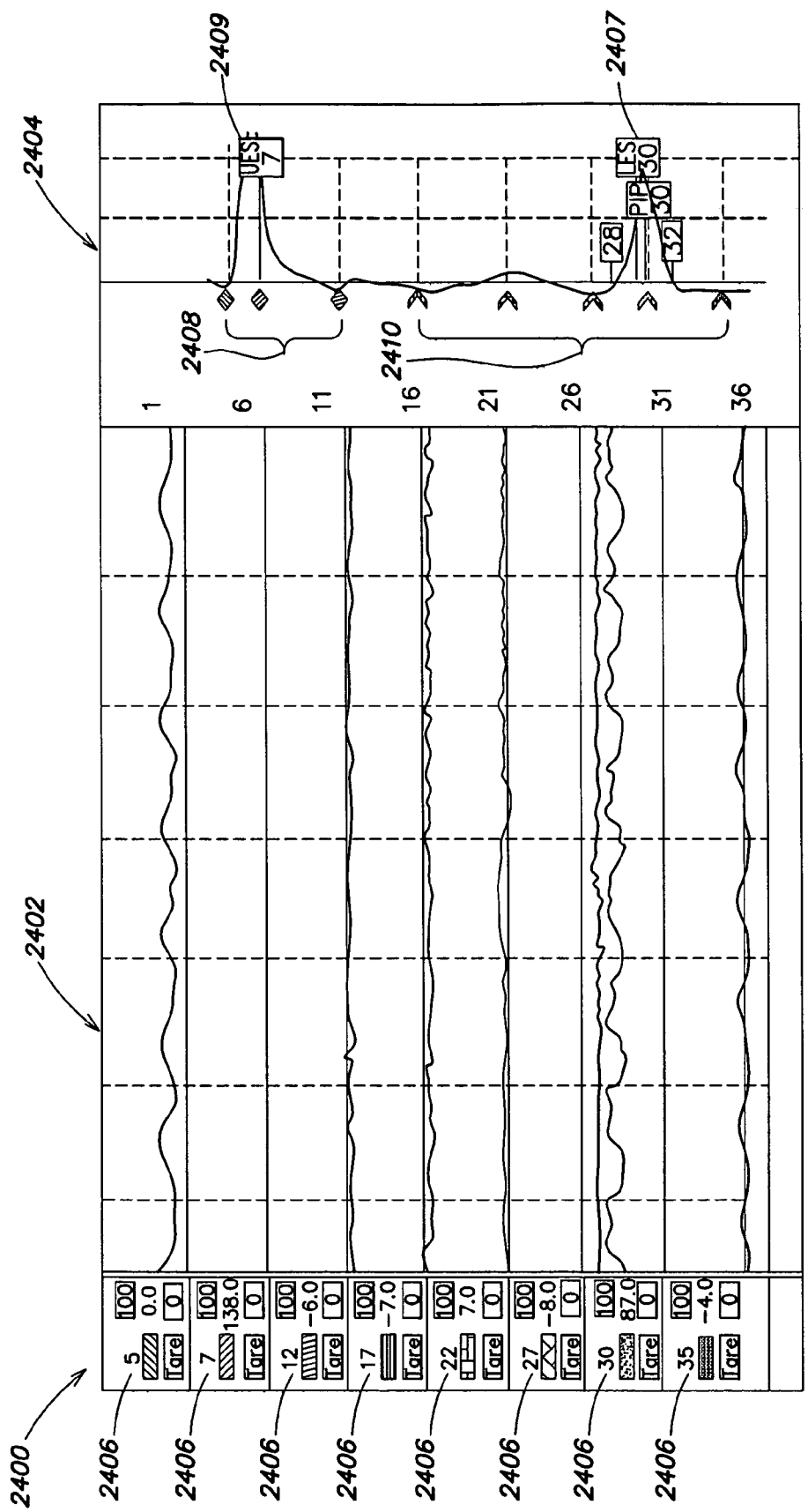
FIG. 24 is an example of a display including a temporal plot and a profile plot on which values detected by a subset of values are visually indicated based on one or more distances defined relative to the locations of one or more anatomical landmarks.

FIG. 24 illustrates an example of a display 2400 including a temporal plot visually indicating value using a line tracing technique and a profile plot 2404 visually indicating values using a line tracing technique. Display 2400 may be generated by a plurality of the components of visualization component 106, as will be described in more detail below.

Display 2400 may result from the user inputs illustrated in control panel 2300. UES location identifier 2409 indicates that the UES is located at the location of sensor "7." LES location identifier 2407 indicates that the LES is located at the location of sensor "30." Accordingly, as indicated by sensor identifiers 2406, values detected at sensors "5", "7", "12", "17", "22", "27", "30" and "35" (two cm above UES, at UES, five cm below LES, thirteen cm above LES, eight cm above LES, three cm above LES, at LES, and one cm below LES, respectively) are visually indicated on temporal plot 2402.

Further, the location along the upper GI tract at which the sensors for which values are being visually indicated are indicated by displayed sensor indicators 2408 and 2410 on profile plot 2404. In an embodiment, as illustrated in FIG. 24, the displayed sensor indicators 2408 for sensors selected due to their distance relative to the UES may be visually indicated with a first symbol (e.g., a diamond) and sensor indicators 2410 for sensors selected due to their distances relative to the LES may be visually indicating using a second symbol (e.g., an arrow). The different symbols used to visually indicate displayed sensor indicators 2408 and displayed sensor indicators 2410 indicate to a user an association with a respective landmark.

In an aspect of the invention, landmark referencing components 634 of visualization component 1036 may be configured to visually indicate values detected by a subset of sensors on a temporal plot based on one or distances to find relative to one or more anatomical landmarks, for example, as described above in relation to FIGS. 22-24. The landmark referencing component 634 may be configured with an input to receive user input, for example, user input 604, that defines one or more distances relative to one or more anatomical landmarks, and may be configured to determine the sensors located at the one or more received distances and to output instructions to one or more other components to visually indicate the values detected by the determined sensors on the temporal plot. A landmark referencing component 634 may be configured to output the instructions to visually indicate the values to any of the logical components of visualization component 106, for example, temporal component 608, profile plot component 610, landmark identification component 622, frame display controller 612, or any of the other logical components of visualization component 106. Landmark referencing component 634 may be configured to control the visual indication of control panel 2300.

As described above, when detected values are visually indicated on a temporal plot and a profile plot concurrently, the values visually indicated on the profile plot typically are from a temporal interval for which values are displayed on the temporal plot at a location closest to a temporal origin of the temporal plot (e.g., a column of pixels closest to the origin of the temporal axis). It may be desirable, however, to be able to display values on the profile plot corresponding to a temporal interval selected by a user.

Accordingly, in an embodiment of visually indicating detected values to a user on a temporal plot and a profile plot, concurrently, a user may be enabled to select a specific temporal interval on the temporal plot to be displayed on the profile plot.

Figure 25:
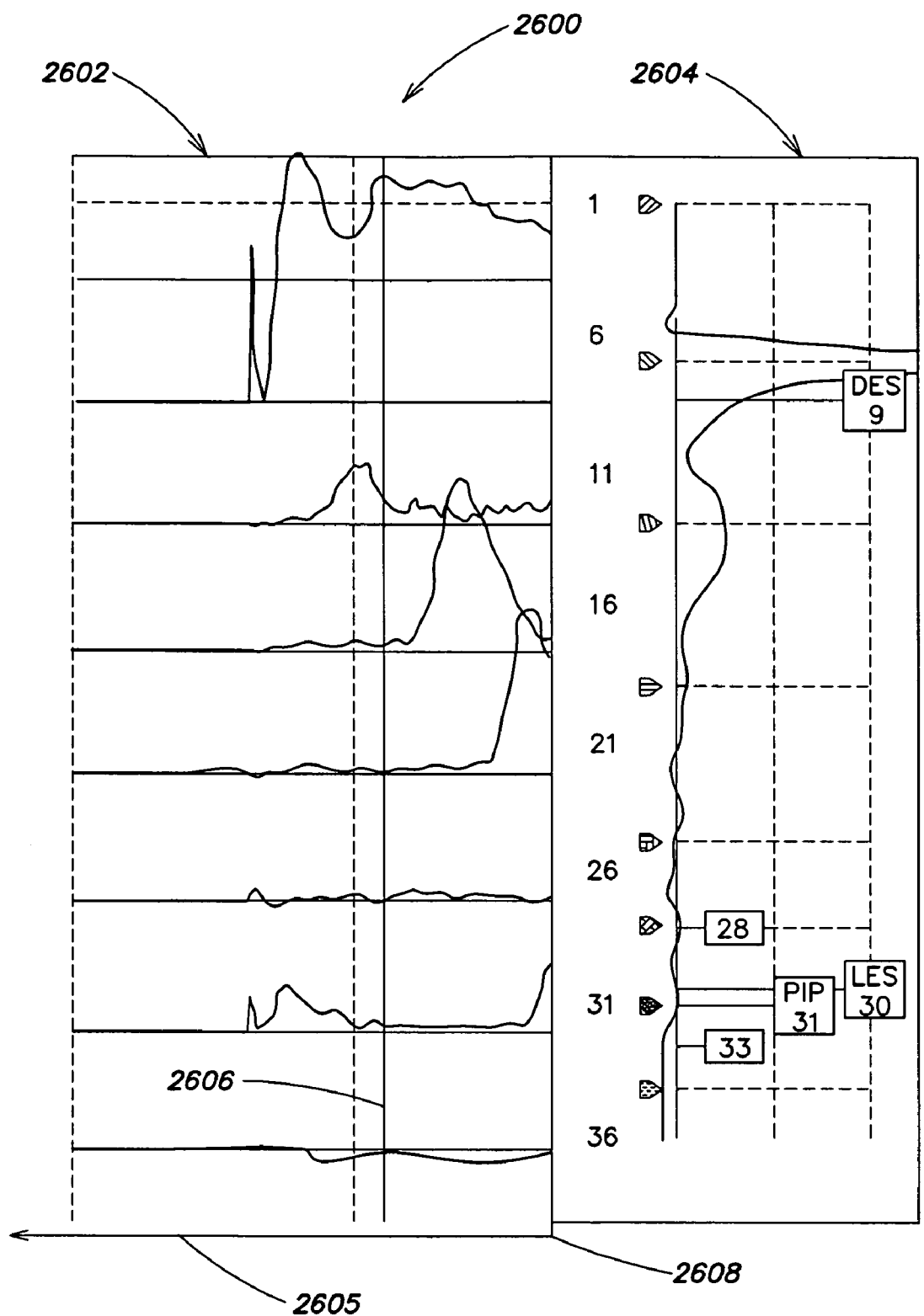
FIG. 25 is a display including a temporal plot and a profile plot where the values visually indicated on the profile plot are determined from a user's selection of a spatial location on the temporal plot.

FIG. 25 is an example of a display 2600, for example, included as part of a GUI, including a temporal plot 2602 and a profile plot 2604 on which detected values are visually indicated to a user. Display 2600 may be generated by logical components of visualization component 106, as will be described in more detail below.

A user may be enabled to click at a specific temporal position along the temporal axis 205 of the temporal plot 2602, in response to which the profile plot 2604 visually indicates values detected during the temporal interval corresponding to the temporal position on the profile plot 2604.

The temporal plot may indicate the spatial position selected by the user with a vertical line, for example, temporal interval indicator 2606. As described above with respect to FIG. 8, values visually indicated on a temporal plot may first be displayed on at or near the origin 2608 of the temporal axis 2605 and may move from right to left over time.

In response to the user selecting a temporal position along the temporal axis 2605, in addition to displaying the temporal position indicator 2606, the profile plot 2604 may visually indicate the values detected during the temporal interval corresponding to the selected temporal position. The profile plot 2604 may continue to display the values detected during the selected temporal interval corresponding to the temporal position, as opposed to being updated with new temporal intervals at the refresh rate of display 2600, until a user indicates that the values corresponding to the temporal position are no longer to be displayed. For example, the user could click on the temporal position indicator 2606. In response to the user de-selecting the spatial position, the profile plot 2604 may return to displaying the value corresponding to the temporal interval nearest the origin 2608 of the temporal plot 2602, which changes over time. A GUI including display 2600 may be configured to enable a user to select and de-select a spatial position for which to visually indicate values using any of a variety of other techniques.

In an aspect of the invention, temporal interval selection component 626 may be configured to enable a user to select a specific temporal interval on a temporal plot and to enable the visual indication of the values detected during the selected temporal interval on the profile plot, for example, as described above in relation to FIG. 25. The temporal interval selection component 626 may receive user inputs specifying a selected interval, and send instructions to one or more logical components of visualization component 106 to display a vertical line corresponding to the selected interval and to visually indicate the values detected during the temporal interval on a profile plot. For example, the temporal interval selection component may send such outputs to the temporal plot component 608, the profile plot component 610, the frame display controller 612 or any of the other logical components of the visualization component 106.

In an embodiment of visually indicating values detected over a period of time, the detected values may be visually indicated on a first temporal plot and a second temporal plot concurrently. For example, a first temporal plot may display values using the first technique (e.g., a contour technique, a line tracing technique or a mesh plot technique) and the second temporal plot may display the same values using a different technique. Optionally, one of the temporal plots may be scaled down such that it can be superimposed on the other temporal plot.

Figure 26:
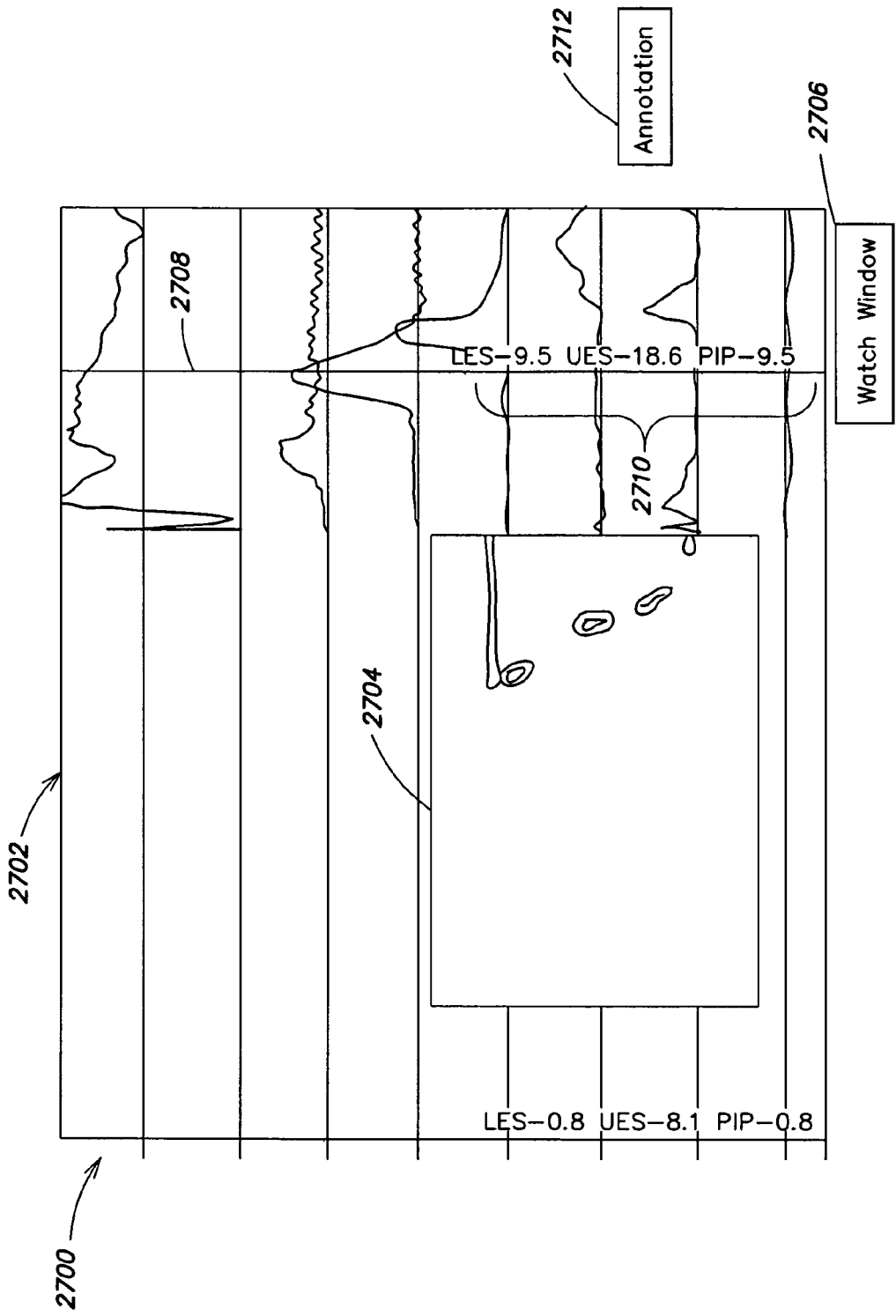
FIG. 26 is an example of a display including a first temporal plot and a second temporal plot on which detected values are visually indicated concurrently.

FIG. 26 is an example of a display 2700 including a first temporal plot 2702 visually indicating values detected over a period of time using a line tracing technique, and a second temporal plot 2704 visually indicating values detected over the period of time using a contour technique. Display 2700 may be generated by components of visualization component 106, as will be described in more detail below.

As illustrated in FIG. 26, the second temporal plot 2704 has been scaled down and superimposed on the first temporal plot 2702. Display 2700 may be part of a GUI that includes a control, for example, control 2706 that enables a user to turn off and turn on the concurrent visual indication of two temporal plots.

Such concurrent visual indication of two temporal plots that each use a different technique for visually indicating values may be beneficial because each technique may convey different information to a user. For example, as described above, the line tracing technique may be superior for visually indicating precise values detected at a sensor over a period of time, whereas the contour technique may be superior for illustrating a finer spatial resolution of values detected over time to a user. It should be appreciated that although FIG. 26 shows a temporal plot using a contour technique 2704 scaled down and superimposed on a temporal plot using a line tracing technique 2702, this aspect of the invention is not limited as such, as the scaled down, superimposed plot 2704 and temporal plot 2702 may each visually indicate values using any of a plurality of techniques.

In an aspect of the invention, the temporal plot component 608 of visualization 106, described above, may be configured to visually indicate values on two temporal plots concurrently, for example, using any of the techniques described above. In another aspect of the invention, annotations may be added to a temporal plot. For example, annotations may indicate when a significant value, for example, the location of an anatomical landmark along a dimension of an organism, has changed further. Other annotations may indicate an event for which the detected values are detected, for example, a cough, breathing, swallowing food, swallowing a liquid. In fact, any information may be added as an annotation to a temporal plot.

If annotating a temporal plot, it may be desirable to indicate a temporal interval to which an annotation applies. Accordingly, in an aspect of the invention, the temporal interval for which an annotation applies is visually indicated on a temporal plot. A GUI on which a temporal plot may be displayed may provide a user controls to select or input an annotation to be added to a temporal plot and may enable a user to select the temporal interval to which the annotation is to be applied.

For example, referring to FIG. 26, temporal plot 2702 may include an annotation 2710, an annotation interval indicator 2708 and one or more annotation components 2712. Thus, annotation 2710 may indicate to a user an annotation for temporal interval corresponding to the temporal position along the temporal axis indicated by annotation interval 2708. Each of the one or more annotation controls may enable a user to specify a different type of annotation. One or more types of these annotations may be predefined and one or more of these annotations may allow a user to customize an annotation to be added to temporal plot 2702.

In an aspect of the invention, the annotation component 624 of the visualization 106 may control a visual indication of annotations on a temporal plot. For example, the annotation component may receive user input, for example, user input 604 input from one or more other components of the visualization component 106, from which the annotation component may determine an annotation to be displayed on a temporal plot and the temporal position along the temporal axis of the temporal plot at which to display the annotation. For example, the annotation component may receive input from the landmark location determination component 632 that indicates that the automatically determined location of an anatomical landmark has changed. Further the anatomical component may receive a user input indicating the location of an anatomical landmark. In response to receiving such output from component 632, annotation component 624 may determine the temporal interval for which to display the changed value of the anatomical landmark location and the new value for the anatomical landmark location. The annotation component 624 may output annotations and locations of annotations to the temporal plot 608 and/or the framed display control 612.

When detecting values over a period of time using sensors along a dimension of an organism, it may occur that one or more of the sensors fail to detect a value during one or more temporal intervals, for example, because one or more sensors malfunctions. Accordingly, it may be desirable to interpolate values for such sensors based on values detected by the remaining sensors during a temporal interval.

Figure 27:
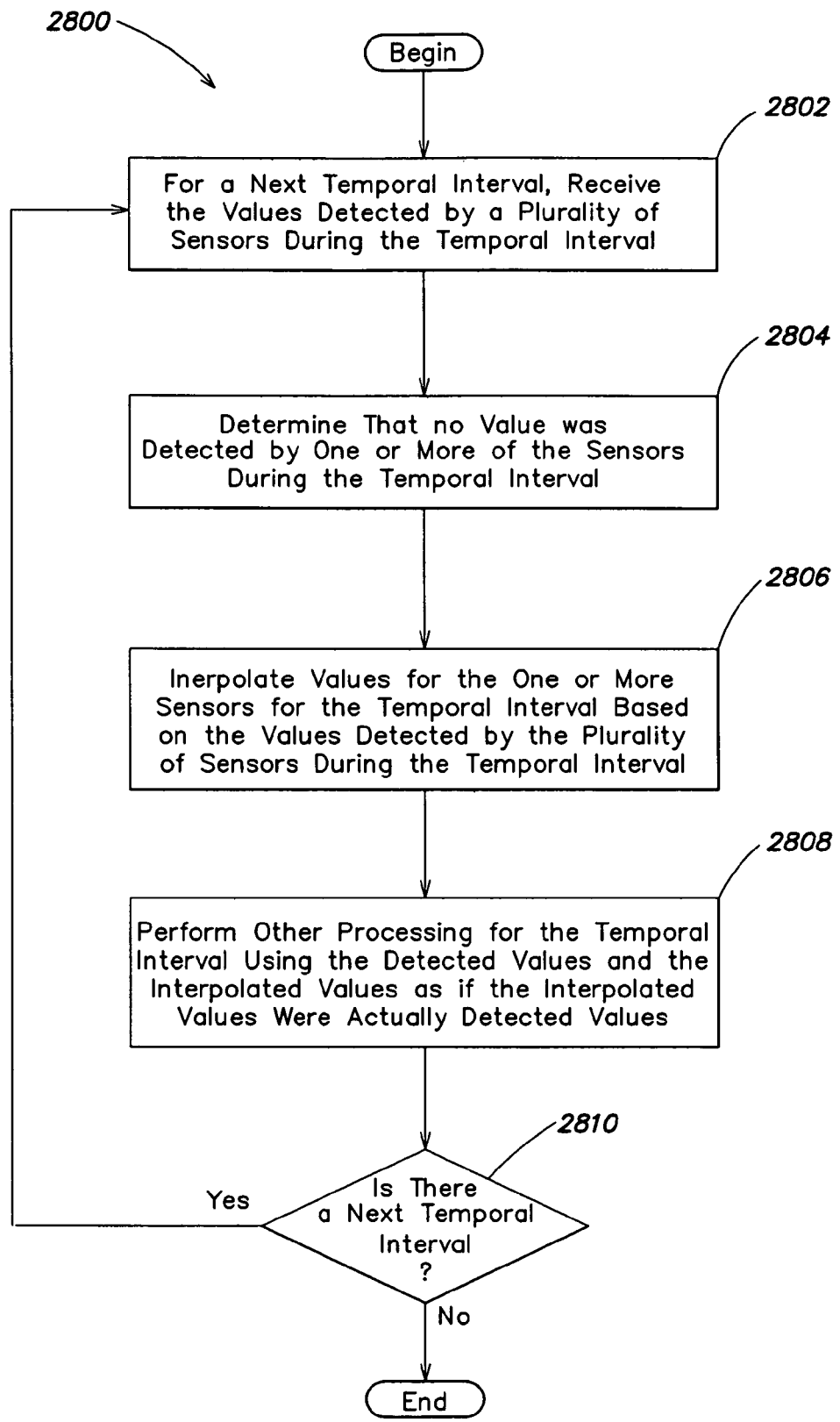
FIG. 27 is a flow chart illustrating an example of a method of interpolating values for one or more sensors for which no values are detected during a temporal interval.

FIG. 27 is a flow chart illustrating an example of a method 2800 for interpolating values for one or more sensors for which no values are detected during a temporal interval. In Act 2802, for a next (e.g., a first) temporal interval, the values detected by a plurality of sensors of an array of sensors during a temporal interval may be received.

In Act 2804, it may be determined that no value is detected by one or more of the sensors of the array of sensors during the temporal interval. Accordingly, in Act 2806, values may be interpolated for the one or more sensors for the temporal interval based on the values detected by the plurality of sensors during the temporal interval. For example, a linear interpolation based on two sensors adjacent to the sensor for which no value was detected may be performed. Alternatively, a non-linear interpolation may be performed, for example, a cubic spline interpolation, based on the plurality of sensors for which values were detected. In an aspect, two or more consecutive sensors may not have detected values. In this case, cubic spline interpolation may be used or a weighted linear interpolation may be applied, in which the determined value for a sensor for which no values were detected is determined based on the two nearest sensors for which values were detected, where for each nearest sensor, its value is weighted depending on its proximity to the sensor for which the value is not detected.

In Act 2808, other processing for the temporal interval may be performed using the detected values and the interpolated values as if the interpolated values were actually detected values. Any of the processing described herein as being performed on detected values also may use the interpolated values as if they were detected values. For example, the processing performed to visually indicate values on a temporal plot or profile plot may use the interpolated values as if they were actually detected values. Further, the determination of the location of one or more anatomical landmarks may use the interpolated values as if they were actually detected values.

In the next Act 2810, it may be determined whether there is a next temporal interval. If there is not a next temporal interval, then method 2800 ends, else the method returns to Act 2802.

In an aspect of the invention, values may be interpolated for sensors for which no values were detected by the virtual sensor interpolator 620 illustrated above in FIG. 6. The virtual sensor interpolator 620 may be configured to implement method 2800. Virtual sensor interpolator 620 may be configured to receive values detected during a temporal interval (e.g., detected value 602, and output values interpolated for sensors for which no values were detected (i.e., virtual sensor values). The virtual sensor interpolator 620 may be configured to send the virtual sensor values to any of a variety of the other logical components of visualization component 106. For example, the virtual sensor interpolator 620 may provide virtual sensor values and detected values to temporal plot component 608 and profile plot component 610 so that these components may visually indicate that the detected values and virtual sensor values, alternatively, or in addition to, the virtual sensor 620 may provide the detected values and virtual sensor values to spatial resolution interpolator 616, which then may process these values and produce additional interpolator values to be passed to temporal component 608 and profile plot component 610, as will be described in more detail below. It should be appreciated that the virtual sensor interpolator 620 can provide values to any of the components of visualization component 106 as is described herein.

In addition to interpolating values for sensors for which no values were detected, values may be interpolated for locations between sensors to increase the spatial resolution of values visually indicated on a temporal plot and/or a profile plot. This interpolation may be applied to values detected during each temporal interval and used to display the values on the temporal plot using any non-line tracing technique, for example, using a contour technique, and may be displayed on a profile plot using any of a variety of non-histogram techniques, for example, a contour technique or a line tracing technique. By interpolating values at locations between locations at which values were detected, the spatial resolution of visually indicated values may be increased to the point where a user perceives the spatial resolution of the data along a spatial axis of a plot as being continuous. It should be appreciated that values interpolated for one or more sensors for which no values were detected may themselves be used to interpolate values for locations between locations of sensors. Consider an example where sensor A is located at one cm, sensor B is located at two cm and sensor C is located at three cm along a dimension of an organism. If sensors A and C detect values but sensor B does not, a value for sensor B may be interpolated from the value detected by sensors A and C and possibly other sensors. Next, values for locations between other sensors, including between sensors A and B and B and C may be interpolated based at least in part on the interpolated value for sensor B.

In another aspect of the invention, spatial resolution interpolator 616 of visualization component 106 may interpolate values for locations between sensors (including virtual sensors that may be determined by virtual sensor interpolator 620), for example, as described above. The spatial resolution interpolator 616 may receive detected values 602 either directly or from virtual sensor interpolator 620 and may receive virtual sensor values from virtual sensor interpolator 620. From these values, the spatial resolution interpolator may determine interpolated values for the locations between sensors and virtual sensors, for example, as described above. The spatial resolution interpolator 616 may be configured to output such interpolated values to the temporal plot component 608, the profile plot component 610, the frame display controller 612, or any of the other logical components of visualization component 106.

In another aspect of visually indicating values detected over a period of time by a plurality of sensors, the values detected by each sensor may be normalized by (e.g., changed by comparison to) another value. This value by which other values are normalized may be referred to as the "normalizing value." The normalizing value may be a predetermined value, a value input by a user, a value detected by a sensor during a particular temporal interval, an average value detected by a sensor over a period of time, or any of a variety of other values.

A user may be enabled to select a sensor ("the baseline sensor") from which to determine the normalizing value (e.g., a value detected during a particular temporal interval by the baseline sensor or an average value detected over a plurality of intervals by the baseline sensor). For example, if the visually indicated values are visually indicated on a GUI, the GUI may enable the user to select a sensor, by example, by typing in the number of the sensor, or a location of the displayed sensor, or by clicking on a sensor identifier or sensor location indicator visually indicated on a temporal plot or profile plot. In response to the selection, the normalizing value may be determined. The values detected by the sensors and values interpolated for the remaining sensors then may be reduced by the normalizing value, and visually indicated to the user, for example, on a temporal plot and/or a profile plot using any of a variety of techniques, including those techniques described herein.

The identity of the baseline sensor and/or the identity of the values detected by the baseline sensor may be visually indicated to the user so that the user knows which of the plurality of sensors is the baseline sensor. Such identity may be visually indicated using any of a variety of techniques, for example, by highlighting an identifier and/or location indicator of the baseline sensor and/or the visual indications of the visual indication of the values detected by the baseline sensor with a predefined tone, or by visually indicating a pointer of other icon. Such indication may assist the user in de-selecting the baseline sensor, for example, by clicking on an identifier or location indicator of the normalized sensor.

Figure 28:
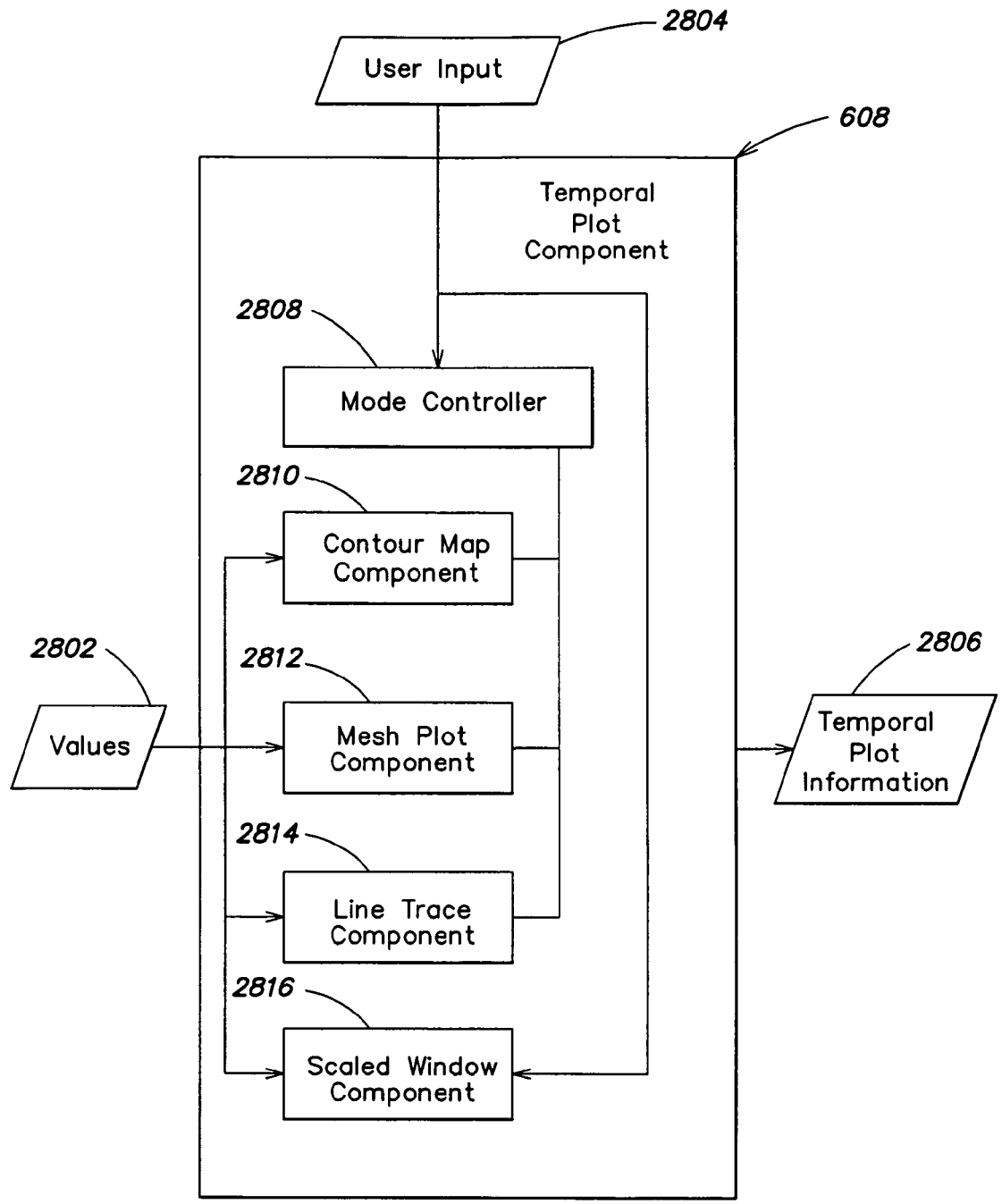
FIG. 28 is a block diagram illustrating an example of a temporal plot component of a visualization component.

FIG. 28 is a block diagram illustrating an example embodiment of a temporal plot component 608 of visualization component 106. Temporal plot component may receive values 2802 and user input 2804 and output temporal plot information 206. Values 2802 may include values detected by a plurality of sensors along a dimension of an organism (e.g., along a length of an upper GI tract) during an interval of time, for example, detected values 602, and may include interpolated values. Interpolated values may be values interpolated for a sensor for which no values were detected during the temporal interval, for example, as may be output by virtual sensor interpolator 620. Further, the interpolated values may include values interpolated for locations along the first dimension between locations at which values were detected, for example, values output by temporal interval selection component 626.

The user input may include any of a variety of the user input described herein for configuring a temporal plot, and may include user input 604. The temporal plot information 2806 may be sent to frame display controller 602, and may be used to configure a frame of display information 606 to be displayed on a GUI, which may be first stored in a frame buffer 618.

The temporal plot component 608 may include a mode controller 2808 that controls the technique to visually indicate values on the temporal plot component 608. The mode controller may receive user input 2804 that controls the technique to be used, and may be configured with a default technique to be used absent any user input. The contour map component 2810 may receive the value 2802 and a control signal from mode controller 2808. If the control signal indicates that the technique to be used to visually indicate the values is the contour technique, then contour map component 2810 may produce the temporal plot information 2806 from the values 2802.

The line tracing map component 2814 may receive the value 2802 and a control signal from mode controller 2808. If the control signal indicates that the technique to be used to visually indicate the values is the line tracing technique, then line tracing map component 2814 may produce the temporal plot information 2806 from the values 2802.

The mesh plot map component 2812 may receive the value 2802 and a control signal from mode controller 2808. If the control signal indicates that the technique to be used to visually indicate the values is the mesh plot technique, then mesh plot map component 2812 may produce the temporal plot information 2806 from the values 2802.

The scaled window component 2816 may be configured to receive values 2802 and user input 2804, and produce a scaled down version of a temporal plot to be superimposed on a larger temporal plot, as described above in relation to FIG. 26.

Figure 29:
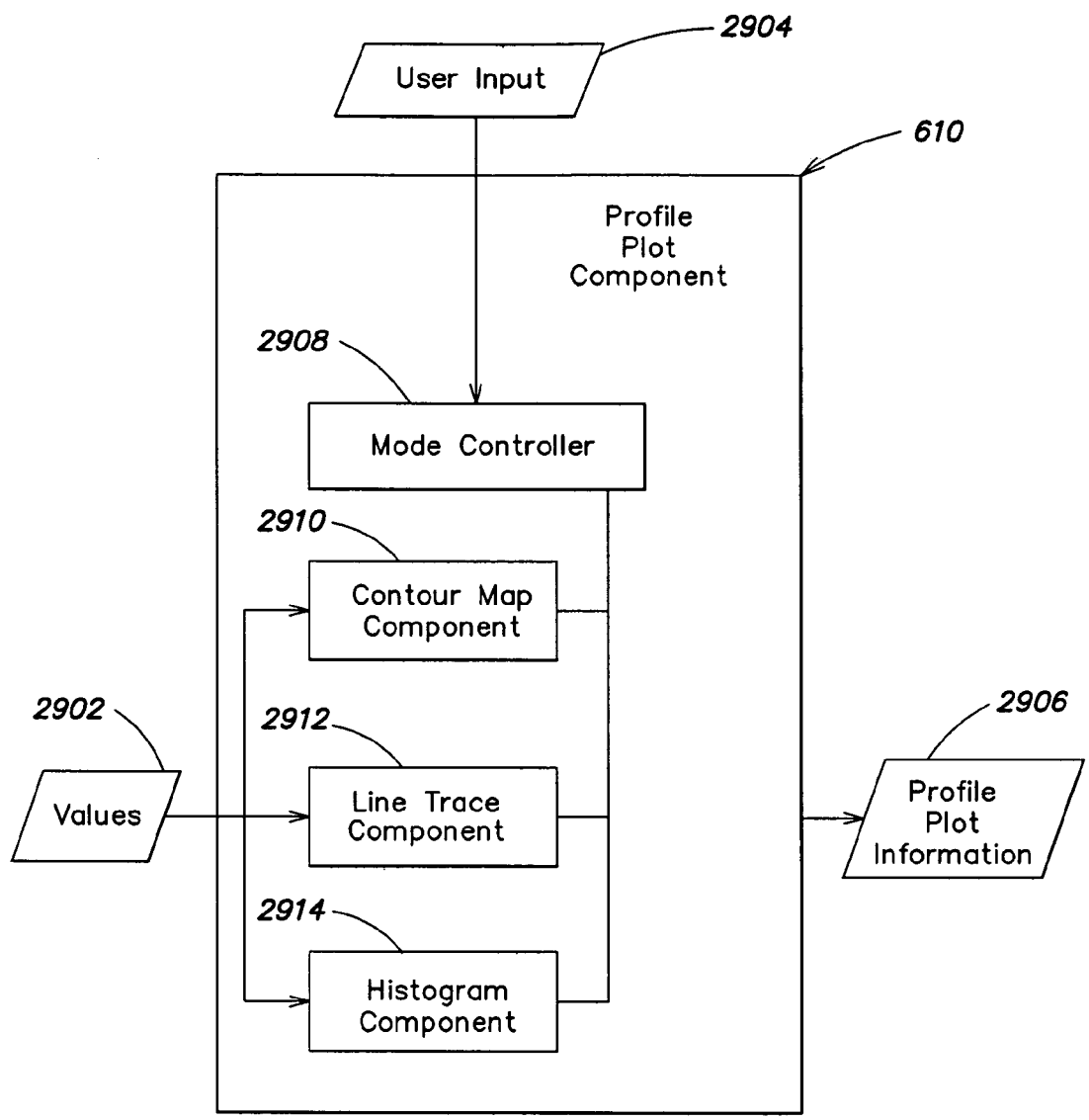
FIG. 29 is a block diagram illustrating an example of a profile plot component of a visualization component.

FIG. 29 is a block diagram illustrating an example embodiment of a profile plot component 610 of visualization component 106. Profile plot component may receive values 2902 and user input 2904 and output profile plot information 206. Values 2902 may include values detected by a plurality of sensors along a dimension of an organism (e.g., along a length of an upper GI tract) during an interval of time, for example, detected values 602 and may include interpolated values. Interpolated values may be values interpolated for a sensor for which no values were detected during the profile interval, for example, as may be output by virtual sensor interpolator 620. Further, the interpolated values may include values interpolated for locations along the first dimension between locations at which values were detected, for example, values output by profile interval selection component 626.

The user input may include any of a variety of the user input described herein for configuring a profile plot, and may include user input 604. The profile plot information 2906 may be sent to frame display controller 602, and may be used to configure a frame 606 to be displayed on a GUI, which may be first stored in a frame buffer 618.

The profile plot component 608 may include a mode controller 2908 that controls the technique to visually indicate values on the profile plot component 608. The mode controller may receive user input 2904 that controls the technique to be used, and may be configured with a default technique to be used absent any user input. The contour map component 2910 may receive the value 2902 and a control signal from mode controller 2908. If the control signal indicates that the technique to be used to visually indicate the values is the contour technique, then contour map component 2910 may produce the profile plot information 2906 from the values 2902.

The line tracing map component 2912 may receive the value 2902 and a control signal from mode controller 2908. If the control signal indicates that the technique to be used to visually indicate the values is the line tracing technique, then line tracing map component 2912 may produce the profile plot information 2906 from the values 2902.

The histogram map component 2914 may receive the value 2902 and a control signal from mode controller 2908. If the control signal indicates that the technique to be used to visually indicate the values is the histogram technique, then histogram map component 2914 may produce the profile plot information 2906 from the values 2902.

Aspects of the invention, including the methods described herein, acts thereof and various embodiments and variations of these methods and acts, individually or in combination, may be defined by computer-readable signals tangibly embodied on a computer-readable medium, for example, a non-volatile recording medium, an integrated circuit memory element, or a combination thereof. Such signals may define instructions, for example, as part of one or more programs, that, as a result of being executed by a computer, instruct the computer to perform one or more of the methods or acts described herein, and/or various embodiments, variations and combinations thereof. Such instructions may be written in any of a plurality of programming languages, for example, Java, Visual Basic, C, C#, or C++, Fortran, Pascal, Eiffel, Basic, COBAL, etc., or any of a variety of combinations thereof. The computer-readable medium on which such instructions are stored may reside on one or more of the components of a system, and may be distributed across one or more of such components.]

The computer-readable medium may be transportable such that the instructions stored thereon can be loaded onto any computer system resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a processor to implement the above-discussed aspects of the present invention.

It should be appreciated that any single component or collection of multiple components of a computer system, for example, the computer system described below in relation to FIGS. 30 and 31, that perform the functions described above with respect to describe or reference the method can be generically considered as one or more controllers that control the above-discussed functions. The one or more controllers can be implemented in numerous ways, such as with dedicated hardware, or using a processor that is programmed using microcode or software to perform the functions recited above.

Various embodiments according to the invention may be implemented on one or more computer systems. These computer systems, may be, for example, general-purpose computers such as those based on Intel PENTIUM-type processor, Motorola PowerPC, Sun UltraSPARC, Hewlett-Packard PA-RISC processors, or any other type of processor. It should be appreciated that one or more of any type computer system may be used to implement any of the systems, system components, methods and acts described above and portions and variations thereof according to various embodiments of the invention. Further, the software design system may be located on a single computer or may be distributed among a plurality of computers attached by a communications network.

A general-purpose computer system according to one embodiment of the invention is configured to perform any of the methods, acts and portions thereof described herein, including any of those described above as being performed by logical components of visualization component 106. It should be appreciated that the system may perform other functions and the invention is not limited to having any particular function or set of functions.

Figure 30:
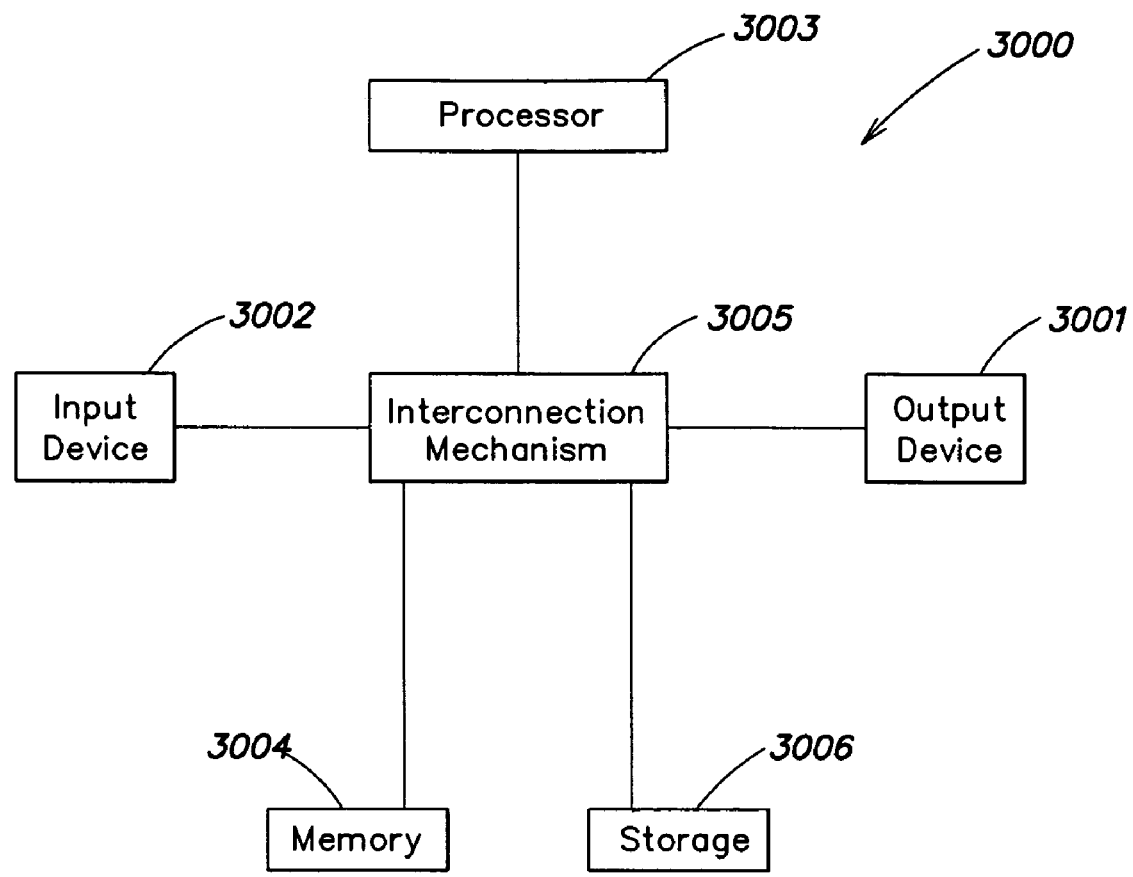

For example, various aspects of the invention may be implemented as specialized software executing in a general-purpose computer system 3000 such as that shown in FIG. 30. The computer system 3000 may include a processor 3003 connected to one or more memory devices 3004, such as a disk drive, memory, or other device for storing data. Memory 3004 is typically used for storing programs and data during operation of the computer system 3000. Components of computer system 3000 may be coupled by an interconnection mechanism 3005, which may include one or more busses (e.g., between components that are integrated within a same machine) and/or a network (e.g., between components that reside on separate discrete machines). The interconnection mechanism 3005 enables communications (e.g., data, instructions) to be exchanged between system components of system 3000. Computer system 3000 also includes one or more input devices 3002, for example, a keyboard, mouse, trackball, microphone, touch screen, and one or more output devices 3001, for example, a printing device, display screen, speaker. In addition, computer system 3000 may contain one or more interfaces (not shown) that connect computer system 3000 to a communication network (in addition or as an alternative to the interconnection mechanism 3005.

Figure 31:
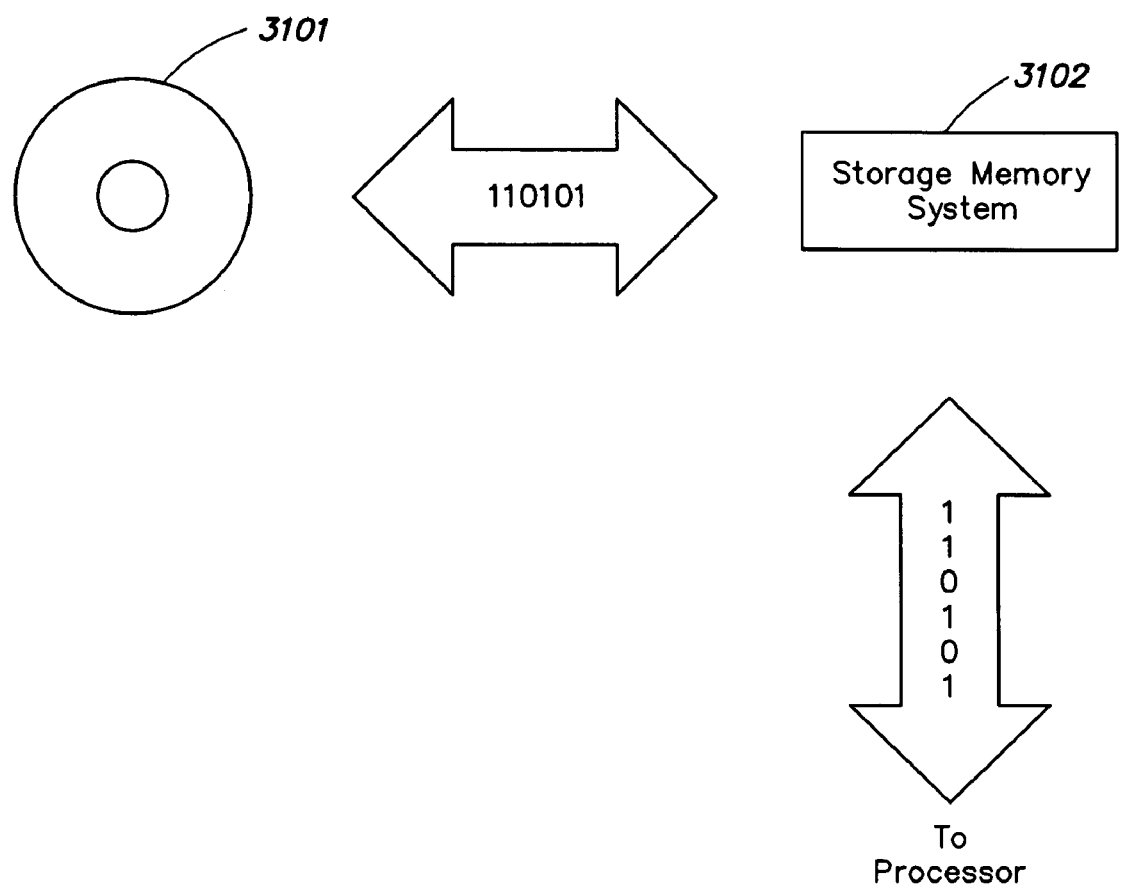
FIG. 31 is block diagram illustrating an example of a memory system of a computer system.

The storage system 3006, shown in greater detail in FIG. 31, typically includes a computer readable and writeable nonvolatile recording medium 3101 in which signals are stored that define a program to be executed by the processor or information stored on or in the medium 3101 to be processed by the program. The medium may, for example, be a disk or flash memory. Typically, in operation, the processor causes data to be read from the nonvolatile recording medium 3101 into another memory 3102 that allows for faster access to the information by the processor than does the medium 3101. This memory 3102 is typically a volatile, random access memory such as a dynamic random access memory (DRAM) or static memory (SRAM). It may be located in storage system 3006, as shown, or in memory system 3004, not shown. The processor 3003 generally manipulates the data within the integrated circuit memory 3004, 3102 and then copies the data to the medium 3101 after processing is completed. A variety of mechanisms are known for managing data movement between the medium 3101 and the integrated circuit memory element 3004, 3102, and the invention is not limited thereto. The invention is not limited to a particular memory system 3004 or storage system 3006.

The computer system may include specially-programmed, special-purpose hardware, for example, an application-specific integrated circuit (ASIC). Aspects of the invention may be implemented in software, hardware or firmware, or any combination thereof. Further, such methods, acts, systems, system elements and components thereof may be implemented as part of the computer system described above or as an independent component.

Although computer system 3000 is shown by way of example as one type of computer system upon which various aspects of the invention may be practiced, it should be appreciated that aspects of the invention are not limited to being implemented on the computer system as shown in FIG. 30. Various aspects of the invention may be practiced on one or more computers having a different architecture or components that that shown in FIG. 30.

Computer system 3000 may be a general-purpose computer system that is programmable using a high-level computer programming language. Computer system 3000 may be also implemented using specially programmed, special purpose hardware. In computer system 3000, processor 3003 is typically a commercially available processor such as the well-known Pentium class processor available from the Intel Corporation. Many other processors are available. Such a processor usually executes an operating system which may be, for example, the Windows 95, Windows 98, Windows NT, Windows 2000 (Windows ME) or Windows XP operating systems available from the Microsoft Corporation, MAC OS System X available from Apple Computer, the Solaris Operating System available from Sun Microsystems, or UNIX available from various sources. Many other operating systems may be used.

The processor and operating system together define a computer platform for which application programs in high-level programming languages are written. It should be understood that the invention is not limited to a particular computer system platform, processor, operating system, or network. Also, it should be apparent to those skilled in the art that the present invention is not limited to a specific programming language or computer system. Further, it should be appreciated that other appropriate programming languages and other appropriate computer systems could also be used.

One or more portions of the computer system may be distributed across one or more computer systems (not shown) coupled to a communications network. These computer systems also may be general-purpose computer systems. For example, various aspects of the invention may be distributed among one or more computer systems configured to provide a service (e.g., servers) to one or more client computers, or to perform an overall task as part of a distributed system. For example, various aspects of the invention may be performed on a client-server system that includes components distributed among one or more server systems that perform various functions according to various embodiments of the invention. These components may be executable, intermediate (e.g., IL) or interpreted (e.g., Java) code which communicate over a communication network (e.g., the Internet) using a communication protocol (e.g., TCP/IP).

It should be appreciated that the invention is not limited to executing on any particular system or group of systems. Also, it should be appreciated that the invention is not limited to any particular distributed architecture, network, or communication protocol.

Various embodiments of the present invention may be programmed using an object-oriented programming language, such as SmallTalk, Java, C++, Ada, or C# (C-Sharp). Other object-oriented programming languages may also be used. Alternatively, functional, scripting, and/or logical programming languages may be used. Various aspects of the invention may be implemented in a non-programmed environment (e.g., documents created in HTML, XML or other format that, when viewed in a window of a browser program, render aspects of a graphical-user interface (GUI) or perform other functions). Various aspects of the invention may be implemented as programmed or non-programmed elements, or any combination thereof.

Having now described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any means, known now or later developed, for performing the recited function.

As used herein, "plurality" means two or more.

As used herein, a "set" of items may include one or more of such items.

As used herein, whether in the written description or the claims, the terms "comprising", "including", "carrying", "having", "containing", "involving", and the like are to be understood to be open-ended, i.e., to mean including but not limited to. Only the transitional phrases "consisting of" and "consisting essentially of", respectively, shall be closed or semi-closed transitional phrases, as set forth, with respect to claims, in the United States Patent Office Manual of Patent Examining Procedures (Original Eighth Edition, August 2001), Section 2111.03

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method of visually indicating to a user values of a physical property detected over a period of time by a plurality of sensors located along a segment of an organism, wherein the period of time includes a plurality of temporal intervals, the method comprising acts of:

(A) for a first of the plurality of temporal intervals, with a computing device operative to provide a display and coupled to receive data from the plurality of the sensors:
      i) determining in real time, based on outputs of the plurality of sensors, a plurality of values of the physical property during the temporal interval, each of the plurality of values corresponding to a coordinate of a temporal plot having a temporal axis representing time and a spatial axis, oriented orthogonally to the temporal axis, representing a spatial dimension of the segment, each coordinate having a spatial position relative to the spatial axis that corresponds to a location on the segment having the value of the physical property, and each coordinate having a temporal position relative to the temporal axis that corresponds to the temporal interval; and
      ii) displaying the temporal plot, the displaying comprising visually indicating the plurality of values using, for each of the plurality of values, a tone corresponding to the value at a coordinate of the temporal plot corresponding to the value;
   (B) repeating act (A) for a next one or more of the plurality of temporal intervals in sequence, including concurrently visually indicating to the user on the temporal plot a plurality of values determined during the one or more next temporal intervals and the plurality of values determined during the first temporal interval, the tones displayed for the plurality of values determined during the temporal interval and the one or more next temporal intervals being displayed at positions relative to the temporal axis such that the temporal plot indicates changes in the physical property; and
   (C) concurrently with the acts (A) and (B), displaying an image of at least one anatomical feature of the segment aligned along the spatial axis with values of the plurality of values representing the property as measured with the sensors at the anatomical feature.

2. The method of claim 1, wherein the physical property is pressure along a lumen of the organism.

3. The method of claim 1, further comprising:
   (D) prior to each performance of act (B), shifting, in a first direction along the temporal axis, the temporal position at which the plurality of values determined for each previous temporal interval is visually indicated by an amount corresponding to a duration of each temporal interval, such that the repeated performances of acts (A) and (B) result in a user perceiving the visual indications of the values moving in the first direction along the temporal axis on the temporal plot.

4. The method of claim 1, wherein act (B) is performed at a predefined rate that results in a human perceiving the repeated performances of act (A) as being temporally continuous.

5. The method of claim 1, wherein the segment comprises at least part of an esophagus of the organism and the act (C) comprises displaying a graphical depiction of the esophagus.

6. The method of claim 1, wherein the segment comprises at least part of a stomach of the organism.

7. The method of claim 1, wherein the segment comprises at least part of any one or more of the following: a duodenum, Sphincter of Oddi, small bowel, bile duct, colon, anus or rectum.

8. The method of claim 1, further comprising:
(D) prior to each performance of act (A), for the value detected by each sensor, assigning a tone to the value.

9. The method of claim 1, wherein act (A) includes visually indicating the plurality of values at positions along the spatial axis such that the visual indication of the values is perceived by a human as being spatially continuous along the spatial axis.

10. The method of claim 1, wherein for each temporal interval for which values are displayed in act (A), the values detected during the temporal interval are visually indicated at a predefined proximity to values detected during other temporal intervals relative to the temporal axis such that the visual indication of values detected during consecutive temporal intervals is perceived by a human as being spatially continuous along the temporal axis.

11. The method of claim 1, wherein each sensor of the plurality of sensors is spaced approximately 1.0 centimeters apart from a closest sensor.

12. The method of claim 1, wherein the plurality of sensors are attached to or embedded within a catheter that is located within the organism.

13. The method of claim 12, wherein each sensor of the plurality of sensors is a solid state sensor.

14. The method of claim 13, wherein the plurality of sensors comprises at least twenty-two sensors.

15. The method of claim 14, wherein the plurality of sensors comprises at least thirty-six sensors.

16. The method of claim 1, wherein the temporal plot comprises a contour plot depicting values of the physical property at a plurality of times and the act (C) comprises visually indicating an anatomical landmark of the organism at a spatial position relative to values depicted on the contour plot indicative of a position within the organism at which the landmark is located.

17. The method of claim 16, further comprising acts of:
(D) receiving a user input specifying a distance relative to an anatomical landmark along the spatial dimension; and
(E) determining a value of the physical property at the relative distance and visually indicating the value on the temporal plot at a position along the spatial axis derived from the relative position.

18. The method of claim 16, wherein each performance of acts (A) and (B) includes visually indicating the plurality of values with a short enough delay from the temporal interval during which the values were detected so that the user perceives the visual indication as being concurrent to the detection of the values by the plurality of sensors.

19. The method of claim 18, wherein the anatomical landmark is an upper esophageal sphincter of the organism.

20. The method of claim 18, wherein the anatomical landmark is a lower esophageal sphincter of the organism.

21. The method of claim 18, wherein the anatomical landmark is a pressure inversion point within a lower esophageal sphincter of the organism.

22. The method of claim 18, wherein the physical property is pressure.

23. The method of claim 18, wherein the plurality of sensors are attached to or embedded within a catheter that is located within the organism, the method further comprising acts of:
(D) for at least one of the plurality of temporal intervals, comparing the spatial position of the visual identification of the anatomical landmark on the plot to the spatial position of the visual indications of the physical property; and
(E) adjusting the location of the catheter within the organism based on results of act (C).

24. The method of claim 16, wherein the act (C) comprises aligning
the image of the at least one anatomical feature and the anatomical landmark.

25. The method of claim 1, further comprising acts of:
(D) for each performance of act (A), visually indicating sensor identifiers to the user along the spatial axis of the temporal plot, each sensor identifier identifying a position along the segment for which data has been recorded.

26. The method of claim 25, further comprising acts of:
(E) enabling the user to select and reposition at least one of the sensor identifiers at another position along the spatial axis;
(F) receiving user input indicative of a repositioning of the at least one of the identifiers from a first position to a second position along the spatial axis; and
(G) in response to the user input, altering the display to replace data representing the physical property at a first position along the segment of the organism corresponding to the first position along the spatial axis with data representing the physical property at a second position along the segment of the organism corresponding to the second position along the spatial axis.

27. The method of claim 25, wherein the physical property is pressure.

28. The method of claim 1, wherein:
determining a plurality of values comprises, for a pair of adjacent sensors of a plurality of the sensors, interpolating a value of the physical property at a distance from the reference point between the pair of sensors based at least on the values of the physical property detected by the pair of sensors during the temporal interval.

29. The method of claim 28, wherein the physical property is pressure.

30. The method of claim 28, wherein each performance of acts (A) and (B) includes interpolating the value and visually indicating the interpolated value and the values detected by the plurality of the sensors, respectively, with a short enough delay from the temporal interval during which the values were detected so that the user perceives the visual indication as being concurrent to the detection of the values by the sensors.

31. The method of claim 1, wherein displaying the temporal plot comprises displaying the temporal plot with the temporal axis horizontally.

32. The method of claim 31, wherein displaying the temporal plot comprises displaying the temporal axis with time values further in the past on the left of the display.

33. The method of claim 32, wherein the plurality of sensors are attached to a probe inserted into the organism from an insertion point and displaying the temporal plot comprises displaying the spatial axis with positions closer to the insertion point at the top of the display.

34. The method of claim 1, wherein:
the plurality of sensors comprises sensors positioned on a probe, the probe having at least one additional sensor, the additional sensor being disposed between a first sensor and a second sensor of the plurality of sensors; and
determining a plurality of values based on the outputs of the plurality of sensors comprises determining a value at a position along the organism corresponding to a position adjacent the additional sensor by interpolating a value based at least on the values of the physical property detected by the first sensor and the second sensor during the temporal interval.

35. A method of visually indicating to a user values of a physical property detected over a period of time by a plurality of sensors located along a segment of an organism, wherein the period of time includes a plurality of temporal intervals, the method comprising acts of:
(A) for a first of the plurality of temporal intervals, with a computing device operative to provide a display and coupled to receive data from the plurality of the sensors:
  i) determining in real time, based on outputs of the plurality of sensors, a plurality of values of the physical property during the temporal interval, each of the plurality of values corresponding to a coordinate of a temporal plot having a temporal axis representing time and a spatial axis, oriented orthogonally to the temporal axis, representing a spatial dimension of the segment, each coordinate having a spatial position relative to the spatial axis that corresponds to a location on the segment having the value of the physical property, and each coordinate having a temporal position relative to the temporal axis that corresponds to the temporal interval; and
  ii) displaying the temporal plot, the displaying comprising visually indicating the plurality of values using, for each of the plurality of values, a tone corresponding to the value at a coordinate of the temporal plot corresponding to the value; and
(B) repeating act (A) for a next one or more of the plurality of temporal intervals in sequence, including concurrently visually indicating to the user on the temporal plot a plurality of values determined during the one or more next temporal intervals and the plurality of values determined during the first temporal interval, the tones displayed for the plurality of values determined during the temporal interval and the one or more next temporal intervals being displayed at positions relative to the temporal axis such that the temporal plot indicates changes in the physical property;
(C) concurrently to performing act (A), displaying to the user a profile plot having a spatial axis, the displaying including visually indicating the plurality of values of the physical property determined for the first temporal interval coordinates of the profile plot at positions along the spatial axis that correspond to positions along the segment represented by the values; and
(D) concurrently to performing act (B), repeating act (C) for the next one or more temporal intervals, including, for each performance of act (D), replacing the visual indication of the plurality of values for a temporal interval with the visual indication of the value determined during a next temporal interval.

36. The method of claim 35, further comprising:
receiving an indication of an anatomical landmark relative to the temporal plot; and
configuring an image of an anatomical feature based at least in part on the position within the organism of the anatomical landmark.

37. The method of claim 35, further comprising acts of:
(E) for each performance of act (A), visually indicating an image of at least a portion of the organism concurrently to visually indicating the plurality of values.

38. The method of claim 37, wherein the physical property is pressure.

39. The method of claim 37, wherein the plurality of sensors are attached to or embedded within a catheter that is located within the organism, the method further comprising acts of:
(F) for at least one of the plurality of temporal intervals, comparing the spatial position of the visual identification of the anatomical landmark on the temporal plot to the spatial position of the visual indications of the physical property; and
(G) adjusting the location of the catheter within the organism based on results of act (E).

40. A method of visually indicating to a user values of a physical property detected over a period of time by a plurality of sensors located along a segment of an organism, wherein the period of time includes a plurality of temporal intervals, the method comprising acts of:
(A) for a first of the plurality of temporal intervals, with a computing device operative to provide a display and coupled to receive data from the plurality of the sensors:
  i) determining, based on outputs of the plurality of sensors, a plurality of values of the physical property during the temporal interval, each of the plurality of values representing the value of the physical property at a location along the segment; and
  ii) displaying a temporal plot to the user, the temporal plot being displayed with a temporal axis representing time, the displaying comprising visually indicating at least a subset of the values, each of the values being indicated at a coordinate having a temporal position relative to the temporal axis that corresponds to the temporal interval and a position along a spatial axis representing a position along the segment having the physical property represented by the value; and
(B) concurrently to performing act (A), displaying to the user a profile plot having a spatial axis, the displaying including visually indicating each of the plurality of values at a coordinate of the profile plot at a position along the spatial axis representing a position along the segment having the physical property represented by the value; and
(C) repeating act (A) for a next one or more of the plurality of temporal intervals in sequence, including concurrently visually indicating to the user on the temporal plot the at least the subset of the plurality of values determined during the one or more next temporal intervals and the values at each of the at least the subset of the plurality of values determined during the first temporal interval,
(D) concurrently to performing act (C), repeating act (B) for the next one or more temporal intervals, including, for each performance of act (D), replacing the visual indication of the plurality of values determined for a temporal interval with the visual indication of the value detected by the sensor during a next temporal interval; and
(E) visually indicating at least one anatomical feature of the segment,
wherein the temporal plot, the profile plot and the visual indication of the anatomical feature are positioned to visually indicate a correspondence between the spatial axis of the temporal plot and the spatial axis of the profile plot and the anatomical feature.

41. The method of claim 40, wherein the physical property is pressure along a lumen of the organism.

42. The method of claim 40, wherein the plurality of sensors are attached to or embedded within a catheter that is located within the organism.

43. The method of claim 40, wherein each performance of acts (A) and (B) includes visually indicating the plurality of values with a short enough delay from the temporal interval during which the values were detected so that the user perceives the visual indication as being concurrent to the detection of the values by the sensors.

44. The method of claim 40, wherein the profile plot has a value axis, oriented orthogonally to the spatial axis, and for each performance of act (B), the coordinate at which each value of the plurality of values is displayed has a value position relative to the value axis that corresponds to the value.

45. The method of claim 44, further comprising an act of:
(F) prior to performing act (B) for each temporal interval, for at least one pair of adjacent sensors of the plurality of the sensors, interpolating one or more values of the physical property at one or more locations between the pair of sensors based at least on the values of the physical property detected by the pair of sensors during the temporal interval,
wherein each performance of act (B) further includes visually indicating the interpolated values on the profile plot, wherein each interpolated value is displayed at a coordinate having a spatial position relative to the spatial axis that corresponds to a position between the positions of sensors of the pair, and
wherein, for each performance of act (B), displaying both the values detected by the sensors and the interpolated values results in the user perceiving the visually indications of the detected values and interpolated values as a continuous line.

46. The method of claim 40, wherein displaying the temporal plot comprises displaying the temporal axis horizontally.

47. The method of claim 46, wherein displaying the temporal plot comprises, for each of the next one or more temporal intervals, visually indicating the at least the subset of the plurality of values determined during the temporal interval, to the right of the at least the subset of the plurality of values determined during a prior temporal interval.

48. The method of claim 47, wherein the plurality of sensors are attached to a probe inserted into the organism from an insertion point and displaying the temporal plot comprises displaying the spatial axis with positions closer to the insertion point at the top of the display.

49. The method of claim 40, wherein:
the plurality of sensors comprises sensors positioned on a probe, the probe having at least one additional sensor, the additional sensor being disposed between a first sensor and a second sensor of the plurality of sensors; and
determining a plurality of values based on the outputs of the plurality of sensors comprises determining a value at a position along the organism corresponding to a position adjacent the additional sensor by interpolating a value based at least on the values of the physical property detected by the first sensor and the second sensor during the temporal interval.

50. The method of claim 40, wherein the temporal plot comprises a contour plot depicting values of the physical property at a plurality of times and the method further acts of:

(F) visually indicating an anatomical landmark of the organism at a spatial position relative to values depicted on the contour plot indicative of a position within the organism at which the landmark is located.

51. The method of claim 50, further comprising acts of:
(G) receiving a user input specifying a distance relative to an anatomical landmark along the spatial dimension; and
(H) determining a value of the physical property at the relative distance and visually indicating the value on the temporal plot at a position along the spatial axis derived from the relative position.

52. The method of claim 50, wherein each performance of acts (A) and (C) includes visually indicating the plurality of values with a short enough delay from the temporal interval during which the values were detected so that the user perceives the visual indication as being concurrent to the detection of the values by the plurality of sensors.

53. The method of claim 52, wherein the anatomical landmark is an upper esophageal sphincter of the organism.

54. The method of claim 52, wherein the anatomical landmark is a lower esophageal sphincter of the organism.

55. The method of claim 52, wherein the anatomical landmark is a pressure inversion point within a lower esophageal sphincter of the organism.

56. The method of claim 52, wherein the physical property is pressure.

57. The method of claim 52, wherein the plurality of sensors are attached to or embedded within a catheter that is located within the organism, the method further comprising acts of:
(G) identifying in a displayed plot a pattern characteristic of an anatomical landmark; and
(H) adjusting the location of the catheter within the organism based on the position of the pattern within the displayed plot.

58. The method of claim 50, further comprising:
(G) for each performance of act (A), visually indicating an image of at least a portion of the organism on the plot concurrently to visually indicating the values and the anatomical landmark.

59. The method of claim 58, wherein act (G) further comprises:
configuring the image based at least in part on the position within the organism of the anatomical landmark.

60. The method of claim 40, further comprising acts of:
(F) for each performance of act (A), visually indicating an image of at least a portion of the organism concurrently to visually indicating the plurality of values.

61. The method of claim 60, wherein the physical property is pressure.

62. The method of claim 60, wherein the plurality of sensors are attached to or embedded within a catheter that is located within the organism, the method further comprising acts of:
(G) identifying in a displayed plot a pattern characteristic of an anatomical landmark; and
(H) adjusting the location of the catheter within the organism based on the position of the pattern within the displayed plot.

63. The method of claim 40, further comprising acts of:
(F) for each performance of act (A), visually indicating sensor identifiers to the user along the spatial axis of the temporal plot, each sensor identifier identifying a position along the segment for which data has been recorded.

64. The method of claim 63, further comprising acts of:
(G) enabling the user to select and reposition at least one of the sensor identifiers at another position along the spatial axis;
(H) receiving user input indicative of a repositioning of the at least one of the identifiers from a first position to a second position along the spatial axis; and
(I) in response to the user input, altering the display to replace data representing the physical property at a first position along the segment of the organism corresponding to the first position along the spatial axis with data representing the physical property at a second position along the segment of the organism corresponding to the second position along the spatial axis.

65. The method of claim 63, wherein the physical property is pressure.

66. the method of claim 40, wherein:
determining a plurality of values comprises, for a pair of adjacent sensors of a plurality of the sensors, interpolating a value of the physical property at a distance from the reference point between the pair of sensors based at least on the values of the physical property detected by the pair of sensors during the temporal interval.

67. The method of claim 66, wherein the physical property is pressure.

68. The method of claim 66, wherein each performance of acts (A) and (C) includes interpolating the value and visually indicating the interpolated value and the values detected by the plurality of the sensors, respectively, with a short enough delay from the temporal interval during which the values were detected so that the user perceives the visual indication as being concurrent to the detection of the values by the sensors.

69. The method of claim 40, wherein:
the computing device comprises a recording medium; and
determining, based on outputs of the plurality of sensors, a plurality of values of the physical property during the temporal interval, comprises determining the values post hoc by reading the values from the recording medium.

70. A method of visually indicating to a user values of a physical property detected over a period of time by a plurality of sensors located along a segment of an organism, wherein the period of time includes a plurality of temporal intervals, the method comprising, with a computing device operative to provide a display, acts of:
for each of a plurality of temporal intervals during the period:
i) determining, based on outputs of the plurality of sensors, a plurality of values of the physical property during the temporal interval, each of the plurality of values representing the value of the physical property at a location along the segment; and
ii) displaying to the user the plurality of values on a temporal plot, the temporal plot being displayed with a temporal axis representing time and a spatial axis representing a position along the segment, the displaying comprising visually indicating each of the plurality of values at a coordinate having a position relative to the temporal axis that corresponds to the temporal interval and a position relative to the spatial axis representing a position along the segment having the physical property represented by the value; and
concurrent with displaying the temporal plot, displaying to the user a profile plot having a spatial axis, the profile plot comprising visual indications of a plurality of values associated with a position along the temporal axis of the temporal plot, each of the plurality of values being displayed at a coordinate of the spatial axis of the profile plot representing a position along the segment having the physical property represented by the value during a temporal interval represented by the position along the temporal axis; and
visually indicating at least one anatomical feature of the segment,
wherein the temporal plot, the profile plot and the visual indication of the anatomical feature are positioned to visually indicate a correspondence between the spatial axis of the temporal plot and the spatial axis of the profile plot and the anatomical feature.

71. The method of claim 70, wherein displaying to the user the plurality of values on a temporal plot comprises displaying the plurality of values in real time.

72. The method of claim 70, wherein displaying to the user the plurality of values on a temporal plot comprises displaying the plurality of values post hoc.

73. The method of claim 70, wherein displaying to the user the plurality of values on a temporal plot comprises displaying the values with the temporal axis oriented horizontally and the spatial axis oriented vertically.

74. The method of claim 73, wherein:
displaying the profile plot comprises displaying the profile plot to the right of the temporal plot; and
displaying the plurality of values on the temporal plot comprises displaying the values in accordance with a color map.

75. The method of claim 74, wherein displaying the at least on anatomical feature comprises displaying the anatomical feature overlaid on the profile plot.

76. The method of claim 75, wherein the at least on anatomical feature comprises an image of a portion of a gastrointestinal tract.

77. The method of claim 74, wherein:
displaying to the user the plurality of values on a temporal plot comprises displaying the plurality of values in real time by shifting, for each of the plurality of temporal intervals, values on the temporal plot to the left.

* * * * *

UNITED STATES PATENT AND TRADEMARK OFFICE
CERTIFICATE OF CORRECTION

PATENT NO. : 7,476,204 B2
APPLICATION NO. : 10/281068
DATED : January 13, 2009
INVENTOR(S) : Thomas R. Parks et al.

Page 1 of 1

It is certified that error appears in the above-identified patent and that said Letters Patent is hereby corrected as shown below:

Col. 1, Lines 24 and 25, should read:

vided for by the terms of Contract/Grant No. 1 R43 DK56539-01 awarded by
National Institutes of Health.

Signed and Sealed this
Twelfth Day of June, 2012

David J. Kappos
*Director of the United States Patent and Trademark Office*